US012749570B2

(12) United States Patent
Ronen et al.

(10) Patent No.: US 12,749,570 B2
(45) Date of Patent: Sep. 29, 2026

(54) INFORMATION MANAGEMENT SYSTEM AND METHOD

(71) Applicant: CalmWave, Inc., Seattle, WA (US)

(72) Inventors: Ophir Ronen, Seattle, WA (US); Justin Kearns, Lexington, KY (US); Keith Boudreau, Durham, NC (US); Christian Bauer, Frisco, TX (US); Michael Gruzynski, Seattle, WA (US); David Garner, Bothell, WA (US); Thomas Dziedzic, Elmwood Park, IL (US)

(73) Assignee: CALMWAVE, INC., Seattle, WA (US)

( * ) Notice: Subject to any disclaimer, the term of this patent is extended or adjusted under 35 U.S.C. 154(b) by 126 days.

(21) Appl. No.: 18/348,608

(22) Filed: Jul. 7, 2023

(65) Prior Publication Data

US 2024/0192839 A1 Jun. 13, 2024

Related U.S. Application Data

(60) Provisional application No. 63/492,117, filed on Mar. 24, 2023, provisional application No. 63/492,145,
(Continued)

(51) Int. Cl.
*G16H 40/40* (2018.01)
*A61B 5/00* (2006.01)
(Continued)

(52) U.S. Cl.
CPC .......... *G16H 40/40* (2018.01); *A61B 5/0002* (2013.01); *A61B 5/7221* (2013.01);
(Continued)

(58) Field of Classification Search
None
See application file for complete search history.

(56) References Cited

U.S. PATENT DOCUMENTS 5,331,549 A 7/1994 Crawford, Jr.
5,706,013 A 1/1998 Melvin et al.
(Continued)

FOREIGN PATENT DOCUMENTS

EP 3327727 A2 5/2018
EP 3951796 A1 2/2022
(Continued)

OTHER PUBLICATIONS

Non-Final Office Action issued in related U.S. Appl. No. 18/348,867 on Aug. 20, 2024.
(Continued)

*Primary Examiner* — Toan H Vu
(74) *Attorney, Agent, or Firm* — Brian J. Colandreo; Jeffrey T. Placker; Holland & Knight LLP

(57) ABSTRACT

A computer-implemented method, computer program product and computing system for: gathering information from a datasource concerning one or more thresholds within one or more medical institutions, thus defining gathered information; enabling a user to select a viewing lens from a plurality of available viewing lenses through which to display the gathered information, thus defining a selected viewing lens; and rendering at least a portion of the gathered information based, at least in part, upon the selected viewing lens.

15 Claims, 27 Drawing Sheets

10

Related U.S. Application Data filed on Mar. 24, 2023, provisional application No. 63/492,137, filed on Mar. 24, 2023, provisional application No. 63/359,129, filed on Jul. 7, 2022.

(51) Int. Cl.

| | |
|---|---|
| ***G06F 3/04842*** | (2022.01) |
| ***G06F 11/30*** | (2006.01) |
| ***G06F 11/32*** | (2006.01) |
| ***G06Q 10/063*** | (2023.01) |
| ***G06Q 10/0631*** | (2023.01) |
| ***G06Q 10/105*** | (2023.01) |
| ***G08B 7/06*** | (2006.01) |
| ***G08B 29/02*** | (2006.01) |
| ***G16H 10/60*** | (2018.01) |
| ***G16H 15/00*** | (2018.01) |
| ***G16H 40/20*** | (2018.01) |
| ***G16H 40/63*** | (2018.01) |
| ***G16H 40/67*** | (2018.01) |
| ***H04L 41/022*** | (2022.01) |

(52) U.S. Cl.

CPC ............ *A61B 5/7267* (2013.01); *A61B 5/746* (2013.01); *G06F 3/04842* (2013.01); *G06F 11/3072* (2013.01); *G06F 11/327* (2013.01); *G06Q 10/063* (2013.01); *G06Q 10/06315* (2013.01); *G06Q 10/105* (2013.01); *G08B 7/06* (2013.01); *G08B 29/02* (2013.01); *G16H 10/60* (2018.01); *G16H 15/00* (2018.01); *G16H 40/20* (2018.01); *G16H 40/63* (2018.01); *G16H 40/67* (2018.01); *H04L 41/022* (2013.01)

(56) References Cited

U.S. PATENT DOCUMENTS

| | | | | |
|---|---|---|---|---|
| 7,567,844 | B2 | 7/2009 | Thomas et al. | |
| 10,264,968 | B2 | 4/2019 | Gross | |
| 10,311,696 | B2 | 6/2019 | Jenssen | |
| 10,410,134 | B1 | 9/2019 | Cozby et al. | |
| 10,470,971 | B2 | 11/2019 | Choudhury et al. | |
| 10,744,060 | B2 | 8/2020 | Choudhury et al. | |
| 10,970,150 | B1 | 4/2021 | Hunter et al. | |
| 11,024,070 | B2 * | 6/2021 | Nam | G06F 3/0481 |
| 11,127,413 | B2 | 9/2021 | Karimian et al. | |
| 11,183,275 | B1 * | 11/2021 | Chan | G16H 50/30 |
| 11,195,616 | B1 | 12/2021 | Seemakurty et al. | |
| 11,257,587 | B1 | 2/2022 | D'Angelo et al. | |
| 11,380,186 | B1 | 7/2022 | Neubauer | |
| 11,394,629 | B1 | 7/2022 | Grilli et al. | |
| 11,610,403 | B2 | 3/2023 | Hodges et al. | |
| 11,623,564 | B2 | 4/2023 | Switalski et al. | |
| 11,992,657 | B2 | 5/2024 | Campbell | |
| 2003/0063010 | A1 | 4/2003 | Smith et al. | |
| 2003/0135382 | A1 | 7/2003 | Marejka et al. | |
| 2004/0249673 | A1 | 12/2004 | Smith | |
| 2005/0187796 | A1 | 8/2005 | Rosenfeld et al. | |
| 2006/0017561 | A1 | 1/2006 | Albert | |
| 2008/0040151 | A1 | 2/2008 | Moore | |
| 2008/0183054 | A1 | 7/2008 | Kroeger et al. | |
| 2009/0002492 | A1 | 1/2009 | Velipasalar et al. | |
| 2009/0054743 | A1 | 2/2009 | Stewart | |
| 2010/0100427 | A1 | 4/2010 | McKeown et al. | |
| 2011/0001605 | A1 | 1/2011 | Kiani et al. | |
| 2011/0179361 | A1 | 7/2011 | Cardarelli et al. | |
| 2011/0213212 | A1 | 9/2011 | Al-Ali | |
| 2013/0245389 | A1 | 9/2013 | Schultz et al. | |
| 2014/0121989 | A1 | 5/2014 | Kamath et al. | |
| 2014/0253313 | A1 | 9/2014 | Schoenberg | |
| 2014/0365389 | A1 | 12/2014 | Cheek et al. | |
| 2015/0058028 | A1 | 2/2015 | Su et al. | |
| 2015/0081487 | A1 | 3/2015 | Porter et al. | |
| 2015/0137968 | A1 | 5/2015 | Rusin et al. | |
| 2015/0164438 | A1 * | 6/2015 | Halperin | G16H 20/10 340/573.1 |
| 2015/0186608 | A1 | 7/2015 | Fuller et al. | |
| 2015/0187036 | A1 | 7/2015 | Wang et al. | |
| 2015/0195165 | A1 | 7/2015 | Boger | |
| 2015/0213202 | A1 * | 7/2015 | Amarasingham | G16Z 99/00 705/2 |
| 2015/0270915 | A1 | 9/2015 | Perron | |
| 2015/0364022 | A1 | 12/2015 | Dyell et al. | |
| 2016/0022218 | A1 | 1/2016 | Hayes et al. | |
| 2016/0092641 | A1 | 3/2016 | Delaney et al. | |
| 2016/0093205 | A1 | 3/2016 | Boyer | |
| 2016/0132215 | A1 | 5/2016 | Zhang et al. | |
| 2016/0155309 | A1 | 6/2016 | Watson et al. | |
| 2016/0171865 | A1 | 6/2016 | Fuller et al. | |
| 2016/0224920 | A1 | 8/2016 | Doms | |
| 2016/0239611 | A1 * | 8/2016 | Heldt | G16H 70/60 |
| 2016/0283681 | A1 | 9/2016 | Falck et al. | |
| 2016/0287207 | A1 | 10/2016 | Xue | |
| 2017/0046499 | A1 | 2/2017 | Hu et al. | |
| 2017/0098358 | A1 | 4/2017 | Bechtel et al. | |
| 2017/0116552 | A1 | 4/2017 | Deodhar et al. | |
| 2017/0212136 | A1 | 7/2017 | Purvis et al. | |
| 2017/0231537 | A1 | 8/2017 | Al-Ali | |
| 2017/0235910 | A1 | 8/2017 | Cantillon et al. | |
| 2017/0357765 | A1 | 12/2017 | Fauss et al. | |
| 2018/0078219 | A1 | 3/2018 | Selvaraj | |
| 2018/0096110 | A1 * | 4/2018 | Treacy | A61B 5/0205 |
| 2018/0096590 | A1 | 4/2018 | Grubis | |
| 2018/0174680 | A1 | 6/2018 | Sampath et al. | |
| 2018/0208113 | A1 | 7/2018 | Haupts et al. | |
| 2018/0217900 | A1 | 8/2018 | Prahlad et al. | |
| 2018/0243163 | A1 | 8/2018 | Choudhury et al. | |
| 2018/0247023 | A1 | 8/2018 | Divine et al. | |
| 2018/0315285 | A1 | 11/2018 | Janssen | |
| 2018/0351783 | A1 | 12/2018 | Patrick et al. | |
| 2019/0110763 | A1 | 4/2019 | Brasch et al. | |
| 2019/0180592 | A1 | 6/2019 | Woodward | |
| 2019/0206087 | A1 * | 7/2019 | Noll | G06F 3/04897 |
| 2019/0228628 | A1 | 7/2019 | Drscher et al. | |
| 2019/0295696 | A1 | 9/2019 | Yang et al. | |
| 2019/0335308 | A1 | 10/2019 | Patton et al. | |
| 2020/0019911 | A1 | 1/2020 | Powers et al. | |
| 2020/0065925 | A1 | 2/2020 | Nolte et al. | |
| 2020/0078260 | A1 | 3/2020 | Choudhury et al. | |
| 2020/0143655 | A1 | 5/2020 | Gray et al. | |
| 2020/0160993 | A1 | 5/2020 | Xie et al. | |
| 2020/0178903 | A1 | 6/2020 | Chaudhuri et al. | |
| 2020/0281521 | A1 | 9/2020 | Cail | |
| 2020/0337648 | A1 | 10/2020 | Saripalli et al. | |
| 2020/0379823 | A1 | 12/2020 | Lehmann | |
| 2021/0000347 | A1 | 1/2021 | Stump | |
| 2021/0012788 | A1 | 1/2021 | Karimian et al. | |
| 2021/0020274 | A1 | 1/2021 | Liu et al. | |
| 2021/0026019 | A1 | 1/2021 | Gahagan et al. | |
| 2021/0077035 | A1 | 3/2021 | Kayser | |
| 2021/0165476 | A1 | 6/2021 | Menzel et al. | |
| 2021/0366268 | A1 | 11/2021 | Jain et al. | |
| 2022/0019935 | A1 | 1/2022 | Ghatage et al. | |
| 2022/0066998 | A1 | 3/2022 | Jha et al. | |
| 2022/0139204 | A1 | 5/2022 | Millican | |
| 2022/0239563 | A1 | 7/2022 | Yanagihashi et al. | |
| 2022/0241502 | A1 | 8/2022 | Campbell | |
| 2022/0287565 | A1 | 9/2022 | Yeung | |
| 2022/0301677 | A1 | 9/2022 | Chung et al. | |
| 2022/0327691 | A1 * | 10/2022 | Pelissier | G16H 40/67 |
| 2022/0382245 | A1 | 12/2022 | Nalala et al. | |
| 2023/0049981 | A1 | 2/2023 | Vasist et al. | |
| 2023/0098165 | A1 | 3/2023 | Shi et al. | |
| 2023/0218820 | A1 | 7/2023 | Sims et al. | |
| 2023/0263483 | A1 | 8/2023 | Gerder et al. | |
| 2023/0282091 | A1 | 9/2023 | Padani et al. | |
| 2024/0008823 | A1 | 1/2024 | Ronen et al. | |
| 2024/0008824 | A1 | 1/2024 | Ronen et al. | |
| 2024/0012732 | A1 | 1/2024 | Ronen et al. | |
| 2024/0013107 | A1 | 1/2024 | Ronen et al. | |
| 2024/0013638 | A1 | 1/2024 | Ronen et al. | |
| 2024/0013650 | A1 | 1/2024 | Ronen et al. | |

(56) References Cited

U.S. PATENT DOCUMENTS

| | | | |
|---|---|---|---|
| 2024/0013651 A1 | 1/2024 | Ronen et al. |
| 2024/0013896 A1 | 1/2024 | Ronen et al. |
| 2024/0013897 A1 | 1/2024 | Ronen et al. |
| 2024/0013902 A1 | 1/2024 | Ronen et al. |
| 2024/0132075 A1 | 4/2024 | Hata et al. |
| 2024/0221487 A1 | 7/2024 | Arnao |
| 2024/0252752 A1 | 8/2024 | Campbell |
| 2024/0374136 A1 | 11/2024 | Sørensen et al. |
| 2025/0310175 A1 | 10/2025 | Ronen et al. |

FOREIGN PATENT DOCUMENTS

| | | |
|---|---|---|
| WO | 2021/056537 A1 | 4/2021 |
| WO | 2021234037 A1 | 11/2021 |

OTHER PUBLICATIONS

Non-Final Office Action issued in related U.S. Appl. No. 18/348,997 on Aug. 16, 2024.
Notice of Allowance issued in related U.S. Appl. No. 18/348,955 on Jul. 25, 2024.
Notice of Allowance issued in related U.S. Appl. No. 18/349,011 on Aug. 7, 2024.
Notice of Allowance issued in related U.S. Appl. No. 18/349,011 on Aug. 28, 2024.
Final Office Action issued in related U.S. Appl. No. 18/348,867 on Dec. 16, 2024.
Final Office Action issued in related U.S. Appl. No. 18/348,987 on Oct. 15, 2024.
Final Office Action issued in related U.S. Appl. No. 18/349,022 on Dec. 4, 2024.
Non-Final Office Action issued in related U.S. Appl. No. 18/348,848 on Dec. 18, 2024.
Non-Final Office Action issued in related U.S. Appl. No. 18/348,978 on Oct. 1, 2024.
Non-Final Office Action issued in related U.S. Appl. No. 18/348,997 on Dec. 10, 2024.
Notice of Allowance issued in related U.S. Appl. No. 18/348,955 on Oct. 7, 2024.
Notice of Allowance issued in related U.S. Appl. No. 18/348,955 on Oct. 22, 2024.
Non Final Office Action issued in related U.S. Appl. No. 18/348,920 on Sep. 7, 2023.
Non Final Office Action issued in related U.S. Appl. No. 18/348,867 on Sep. 13, 2023.
Martens, M. L. H. (2007). The relationship between perceived stress factors and perceived . . . of nurses working in home and inpatient hospice (Order No. 3259719). Available from ProQuest Dissertations and Theses Professional. (304715697). Retrieved from https://dialog.proquest.com/pr (Year: 2007).
Non-Final Office Action issued in related U.S. Appl. No. 18/348,920 on May 21, 2024.
Non-Final Office Action issued in related U.S. Appl. No. 18/348,987 on issue DATE; Apr. 23, 2024.
Notice of Allowance issued in related U.S. Appl. No. 18/349,011 on issue DATE; Apr. 26, 2024.
Notice of Allowance issued in related U.S. Appl. No. 18/349,011 on issue DATE; May 8, 2024.
Final Office Action issued in related U.S. Appl. No. 18/348,987 on Jan. 9, 2024.
Final Office Action issued in related U.S. Appl. No. 18/349,022 on issue DATE; Feb. 2, 2024.
International Search Report and Written Opinion issued in related Application Serial No. PCT/US2023/027068 on Sep. 25, 2023.
International Search Report and Written Opinion issued in related Application Serial No. PCT/US2023/027127 on Oct. 2, 2023.
International Search Report and Written Opinion issued in related Application Serial No. PCT/US2023/027096 on Oct. 2, 2023.
International Search Report and Written Opinion issued in related Application Serial No. PCT/US2023/027078 on Oct. 4, 2023.
International Search Report and Written Opinion issued in related Application Serial No. PCT/US2023/027123 on Sep. 27, 2023.
International Search Report and Written Opinion issued in related Application Serial No. PCT/US2023/027073 on Sep. 29, 2023.
International Search Report and Written Opinion issued in related Application Serial No. PCT/US2023/027132 on Oct. 10, 2023.
International Search Report and Written Opinion issued in related Application Serial No. PCT/US2023/027136 on Oct. 10, 2023.
Final Office Action issued in related U.S. Appl. No. 18/348,920 on Dec. 26, 2023.
Final Office Action issued in related U.S. Appl. No. 18/348,997 on Jan. 8, 2024.
Final Office Action issued in related U.S. Appl. No. 18/349,011 on Dec. 29, 2023.
Final Office Action issued in related U.S. Appl. No. 18/348,867 on Dec. 28, 2023.
Non Final Office Action issued in related U.S. Appl. No. 15/348,955 on Nov. 22, 2023.
Non-Final Office Action issued in related U.S. Appl. No. 18/349,022 on Jun. 21, 2024.
Notice of Allowance issued in related U.S. Appl. No. 18/348,955 on Jun. 28, 2024.
Notice of Allowance issued in related U.S. Appl. No. 18/349,011 on Jun. 7, 2024.
Non-Final Office Action issued in related U.S. Appl. No. 18/349,022 on Sep. 14, 2023.
Non Final Office Action issued in related U.S. Appl. No. 18/349,011 on Sep. 15, 2023.
Non Final Office Action issued in related U.S. Appl. No. 18/348,997 on Sep. 15, 2023.
Final Office Action issued in related U.S. Appl. No. 18/348,920 on Dec. 30, 2024.
Non-Final Office Action issued in related U.S. Appl. No. 18/348,597 on Jan. 21, 2025.
Non-Final Office Action issued in related U.S. Appl. No. 18/348,614 on Jan. 17, 2025.
Notice of Allowance issued in related U.S. Appl. No. 18/348,978 on Feb. 13, 2025.
Notice of Allowance issued in related U.S. Appl. No. 18/348,978 on Mar. 12, 2025.
Final Office Action issued in related U.S. Appl. No. 18/348,597 on Jun. 5, 2025.
Non-Final Office Action issued in related U.S. Appl. No. 18/348,867 on May 23, 2025.
Non-Final Office Action issued in related U.S. Appl. No. 18/348,920 on Apr. 22, 2025.
Non-Final Office Action issued in related U.S. Appl. No. 18/348,987 on Jun. 2, 2025.
Non-Final Office Action issued in related U.S. Appl. No. 18/348,997 on Apr. 10, 2025.
Non-Final Office Action issued in related U.S. Appl. No. 18/349,022 on Apr. 23, 2025.
Notice of Allowance issued in related U.S. Appl. No. 18/348,978 on Apr. 25, 2025.
Notice of Allowance issued in related U.S. Appl. No. 18/348,978 on Jun. 25, 2025.
Notice of Allowance issued in related U.S. Appl. No. 18/348,978 on Mar. 31, 2025.
Notice of Allowance issued in related U.S. Appl. No. 18/348,978 on May 14, 2025.
Final Office Action issued in related U.S. Appl. No. 18/348,614 on Jul. 2, 2025.
Final Office Action issued in related U.S. Appl. No. 18/348,848 on Jul. 30, 2025.
Final Office Action issued in related U.S. Appl. No. 18/348,987 on Sep. 17, 2025.
Final Office Action issued in related U.S. Appl. No. 18/348,997 on Jul. 28, 2025.
Non Final Office Action issued in related U.S. Appl. No. 18/348,828 on Jul. 25, 2025.

(56) References Cited

OTHER PUBLICATIONS

Notice of Allowance issued in related U.S. Appl. No. 18/348,807 on Aug. 15, 2025.
Notice of Allowance issued in related U.S. Appl. No. 18/348,807 on Sep. 9, 2025.
Notice of Allowance issued in related U.S. Appl. No. 18/348,978 on Aug. 27, 2025.
Final Office Action issued in related U.S. Appl. No. 18/348,920 on Sep. 23, 2025.
Final Office Action issued in related U.S. Appl. No. 18/349,022 on Oct. 22, 2025.
Non Final Office Action issued in related U.S. Appl. No. 18/348,597 on Oct. 1, 2025.
Non-Final Office Action issued in related U.S. Appl. No. 18/348,997 on Nov. 10, 2025.
Notice of Allowance issued in related U.S. Appl. No. 18/348,978 on Oct. 22, 2025.
Final Office Action issued in related U.S. Appl. No. 18/348,867 on Nov. 19, 2025.
Non-Final Office Action issued in related U.S. Appl. No. 18/348,614 on Nov. 25, 2025.
Notice of Allowance issued in U.S. Appl. No. 18/348,807 on Nov. 18, 2025.
Final Office Action issued in related U.S. Appl. No. 19/269,765 on Jan. 8, 2026.

* cited by examiner

FIG. 13B
Hospital - Operations Health
Health Score
87
Benchmark
78
Change
Risk
Overview
Units with elevated risk of staff attrition
Unit Health Scores

FIG. 13C
Health Score
75
Benchmark
65
Change
Risk
10/50
Overview
Nurse responders in unit at elevated risk of attrition
Nurse Responder Individual Health Scores
50
75

FIG. 13D
Health Score
42
Benchmark
70
Change
Risk
High
Overview
Trend & Recommendations
Individual's Scores
50
75

FIG. 15B
CalmWave
Unit · Threshold Manager
CCU 01 Unit
Current Patients Outside CWO
8/20
CalmWave Optimized™ (CWO)
25428
35%

10

INFORMATION MANAGEMENT SYSTEM AND METHOD

RELATED APPLICATION(S)

This application claims the benefit of the following U.S. Provisional Application No. 63/492,117 filed on 24 Mar. 2023; 63/492,137 filed on 24 Mar. 2023; 63/492,145 filed on 24 Mar. 2023; and 63/359,129 filed on 7 Jul. 2022; the entire contents of which are incorporated herein by reference.

TECHNICAL FIELD

This disclosure relates to information systems and methods and, more particularly, to information systems and methods that enable a plurality of devices to communicate and/or be managed.

BACKGROUND

The lack of communication between medical devices can lead to significant problems in managing alarms on those devices. Alarms play a critical role in patient care, alerting healthcare providers to changes in a patient's condition or potential issues with medical devices. However, when devices are not able to communicate effectively with each other, several challenges arise in managing alarms:

Lack of Context and Situational Awareness: Without communication between devices, alarms may lack important context and situational information. For example, a patient's vital signs monitored by one device may trigger an alarm, but this alarm may not be synchronized with alarms from other devices, such as infusion pumps or ventilators. This lack of context can make it challenging for healthcare providers to assess the urgency and priority of each alarm.

Alarm Fatigue and Desensitization: Healthcare providers are frequently exposed to a large number of alarms from various devices. When alarms are not coordinated or synchronized, it can result in an overwhelming number of alarms, leading to alarm fatigue. Alarm fatigue occurs when healthcare providers become desensitized to alarms due to their frequency, leading to delayed or missed responses to critical alarms.

Inefficient Alarm Prioritization and Response: When alarms from different devices are not communicated or integrated, it becomes difficult to prioritize and respond to alarms effectively. Without a centralized system for managing alarms, healthcare providers may need to manually assess and prioritize each alarm separately, potentially leading to delays in responding to critical situations.

Increased Risk of Missed or Delayed Alarms: When devices do not communicate, there is an increased risk of missed or delayed alarms. For example, if a patient's oxygen saturation level is dropping, an alarm from a pulse oximeter may not trigger an alarm on other devices, such as a bedside monitor or nurse call system, potentially delaying the necessary intervention.

The consequences of these problems can be severe, including compromised patient safety, adverse events, and suboptimal clinical outcomes. Moreover, the lack of communication between medical devices adds complexity to healthcare provider workflows and can lead to increased stress and burden on the clinical staff.

Summary of Disclosure

Threshold Manager UX:

In one implementation, a computer-implemented method is executed on a computing device and includes: gathering information from a datasource concerning one or more thresholds within one or more medical institutions, thus defining gathered information; enabling a user to select a viewing lens from a plurality of available viewing lenses through which to display the gathered information, thus defining a selected viewing lens; and rendering at least a portion of the gathered information based, at least in part, upon the selected viewing lens.

One or more of the following features may be included. The plurality of available viewing lenses may include one or more of: a macro level viewing lens; a facility level viewing lens; a unit level viewing lens; a cohort level viewing lens; and an individual level viewing lens. The gathered information may concern, at least in part, one or more thresholds of one or more devices within the one or more medical institutions. A user may be enabled to adjust the one or more thresholds the of one or more devices within the one or more medical institutions. Rendering at least a portion of the gathered information based, at least in part, upon the selected viewing lens may include: graphically locating at least a portion of the one or more thresholds within at least a portion of the one or more medical institutions. The one or more thresholds may be defined, at least in part, within the one or more devices within the one or more medical institutions. The thresholds of a particular patient within the one or more medical institutions may be reviewable via an individual level viewing lens.

In another implementation, a computer program product resides on a computer readable medium and has a plurality of instructions stored on it. When executed by a processor, the instructions cause the processor to perform operations including: gathering information from a datasource concerning one or more thresholds within one or more medical institutions, thus defining gathered information; enabling a user to select a viewing lens from a plurality of available viewing lenses through which to display the gathered information, thus defining a selected viewing lens; and rendering at least a portion of the gathered information based, at least in part, upon the selected viewing lens.

One or more of the following features may be included. The plurality of available viewing lenses may include one or more of: a macro level viewing lens; a facility level viewing lens; a unit level viewing lens; a cohort level viewing lens; and an individual level viewing lens. The gathered information may concern, at least in part, one or more thresholds of one or more devices within the one or more medical institutions. A user may be enabled to adjust the one or more thresholds the of one or more devices within the one or more medical institutions. Rendering at least a portion of the gathered information based, at least in part, upon the selected viewing lens may include: graphically locating at least a portion of the one or more thresholds within at least a portion of the one or more medical institutions. The one or more thresholds may be defined, at least in part, within the one or more devices within the one or more medical institutions. The thresholds of a particular patient within the one or more medical institutions may be reviewable via an individual level viewing lens.

In another implementation, a computing system includes a processor and a memory system configured to perform operations including: gathering information from a datasource concerning one or more thresholds within one or more medical institutions, thus defining gathered information; enabling a user to select a viewing lens from a plurality of available viewing lenses through which to display the gathered information, thus defining a selected viewing lens; and rendering at least a portion of the gathered information based, at least in part, upon the selected viewing lens.

One or more of the following features may be included. The plurality of available viewing lenses may include one or more of: a macro level viewing lens; a facility level viewing lens; a unit level viewing lens; a cohort level viewing lens; and an individual level viewing lens. The gathered information may concern, at least in part, one or more thresholds of one or more devices within the one or more medical institutions. A user may be enabled to adjust the one or more thresholds the of one or more devices within the one or more medical institutions. Rendering at least a portion of the gathered information based, at least in part, upon the selected viewing lens may include: graphically locating at least a portion of the one or more thresholds within at least a portion of the one or more medical institutions. The one or more thresholds may be defined, at least in part, within the one or more devices within the one or more medical institutions. The thresholds of a particular patient within the one or more medical institutions may be reviewable via an individual level viewing lens.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
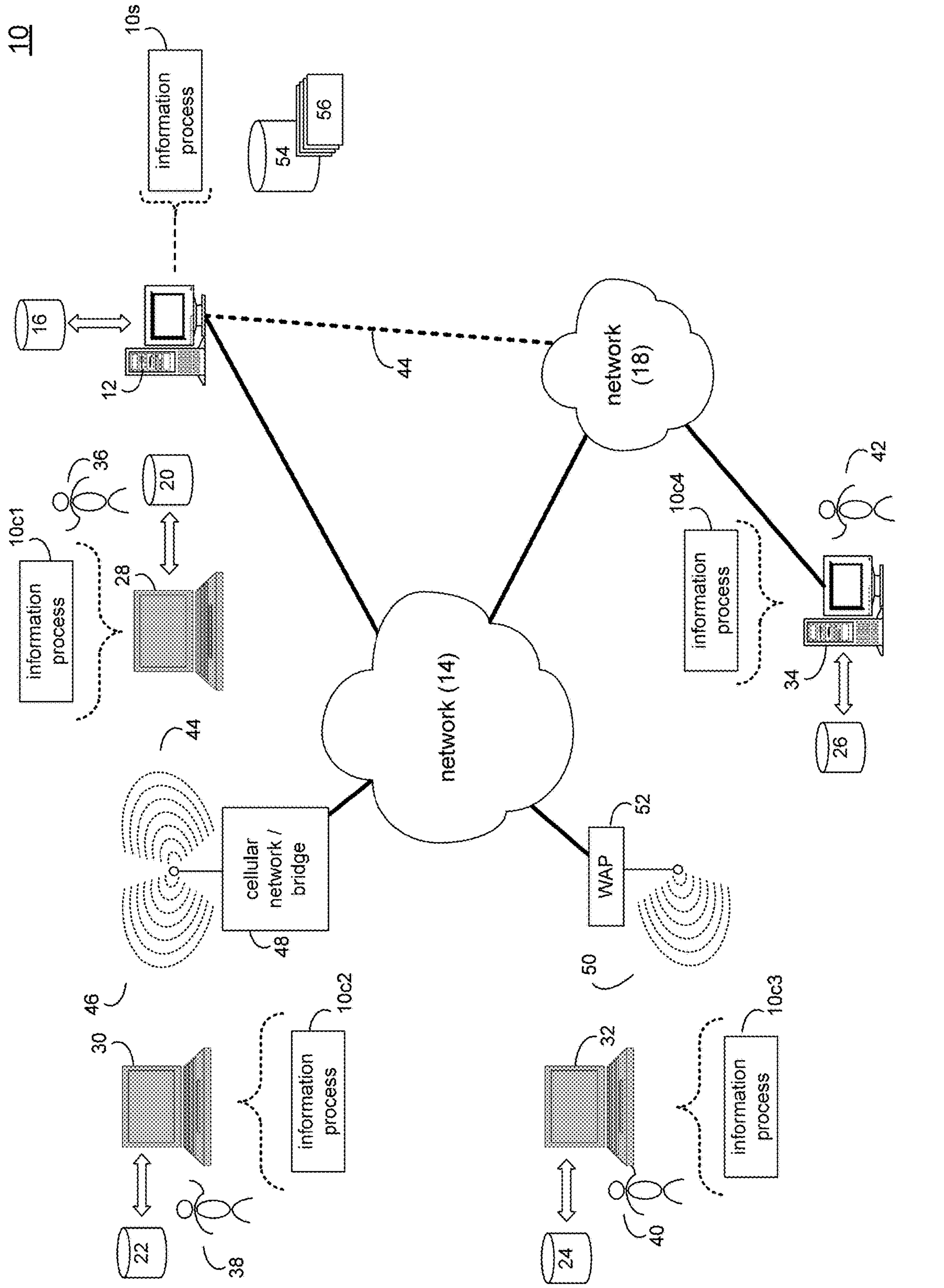
FIG. 1 is a diagrammatic view of a distributed computing network including a computing device that executes an information process according to an embodiment of the present disclosure.

Referring to FIG. 1, there is shown information process 10. Information process 10 may be implemented as a server-side process, a client-side process, or a hybrid server-side/client-side process. For example, information process 10 may be implemented as a purely server-side process via information process 10*s*. Alternatively, information process 10 may be implemented as a purely client-side process via one or more of information process 10*cl*, information process 10*c*2, information process 10*c*3, and information process 10*c*4. Alternatively still, information process 10 may be implemented as a hybrid server-side/client-side process via information process 10*s* in combination with one or more of information process 10*c*1, information process 10*c*2, information process 10*c*3, and information process 10*c*4. Accordingly, information process 10 as used in this disclosure may include any combination of information process 10*s*, information process 10*c*1, information process 10*c*2, information process 10*c*3, and information process 10*c*4.

Information process 10*s* may be a server application and may reside on and may be executed by computing device 12, which may be connected to network 14 (e.g., the Internet or a local area network). Examples of computing device 12 may include, but are not limited to: a personal computer, a server computer, a series of server computers, a mini computer, a mainframe computer, or a cloud-based computing platform.

The instruction sets and subroutines of information process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of information processes 10c1, 10c2, 10c3, 10c4 may include but are not limited to a web browser, a game console user interface, a mobile device user interface, or a specialized application (e.g., an application running on e.g., the Android™ platform, the iOS™ platform, the Windows™ platform, the Linux™ platform or the UNIX™ platform). The instruction sets and subroutines of information processes 10c1, 10c2, 10c3, 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: hard disk drives; RAID devices; random access memories (RAM); read-only memories (ROM), and all forms of flash memory storage devices.

Examples of client electronic devices 28, 30, 32, 34 may include, but are not limited to, a smartphone (not shown), a personal digital assistant (not shown), a tablet computer (not shown), laptop computers 28, 30, 32, personal computer 34, a notebook computer (not shown), a server computer (not shown), a gaming console (not shown), and a dedicated network device (not shown). Client electronic devices 28, 30, 32, 34 may each execute an operating system, examples of which may include but are not limited to Microsoft Windows™, Android™, iOS™, Linux™, or a custom operating system.

Users 36, 38, 40, 42 may access information process 10 directly through network 14 or through secondary network 18. Further, information process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, laptop computer 28 and laptop computer 30 are shown wirelessly coupled to network 14 via wireless communication channels 44, 46 (respectively) established between laptop computers 28, 30 (respectively) and cellular network/bridge 48, which is shown directly coupled to network 14. Further, laptop computer 32 is shown wirelessly coupled to network 14 via wireless communication channel 50 established between laptop computer 32 and wireless access point (i.e., WAP) 52, which is shown directly coupled to network 14. Additionally, personal computer 34 is shown directly coupled to network 18 via a hardwired network connection.

WAP 52 may be, for example, an IEEE 802.11a, 802.11b, 802.11g, 802.11n, Wi-Fi, and/or Bluetooth device that is capable of establishing wireless communication channel 50 between laptop computer 32 and WAP 52. As is known in the art, IEEE 802.11x specifications may use Ethernet protocol and carrier sense multiple access with collision avoidance (i.e., CSMA/CA) for path sharing. As is known in the art, Bluetooth is a telecommunications industry specification that allows e.g., mobile phones, computers, and personal digital assistants to be interconnected using a short-range wireless connection.

Information Process Overview

As will be discussed below in greater detail, information process 10 may be configured enable the analysis of working environments so that the working conditions within these working environments may be ascertained and defined . . . with specific attention being provided to minimizing worker attrition and maximizing worker wellbeing.

While many of the discussions below concern utilizing information process 10 on medical devices within a medical environments, this is for illustrative purposes only and is not intended to be a limitation of this disclosure, as other configurations are possible and are considered to be within the scope of this disclosure. For example, information process 10 may be equally applicable to process control devices, networking devices, computing devices, manufacturing devices, agricultural devices, energy/refining devices, aerospace devices, forestry devices, and defense devices.

Cross-Vendor Middleware:

The following discussion concerns the manner in which information process 10 may be utilized to function as an intermediary between devices that are offered by multiple vendors. As is often the case, individual vendors tend to produce devices that that can communicate amongst themselves but often have difficulties communicating with devices provided by other vendors. Accordingly and as will be discussed below, information process 10 may be configured to effectuate communication between devices produced by different vendors.

Figure 2:
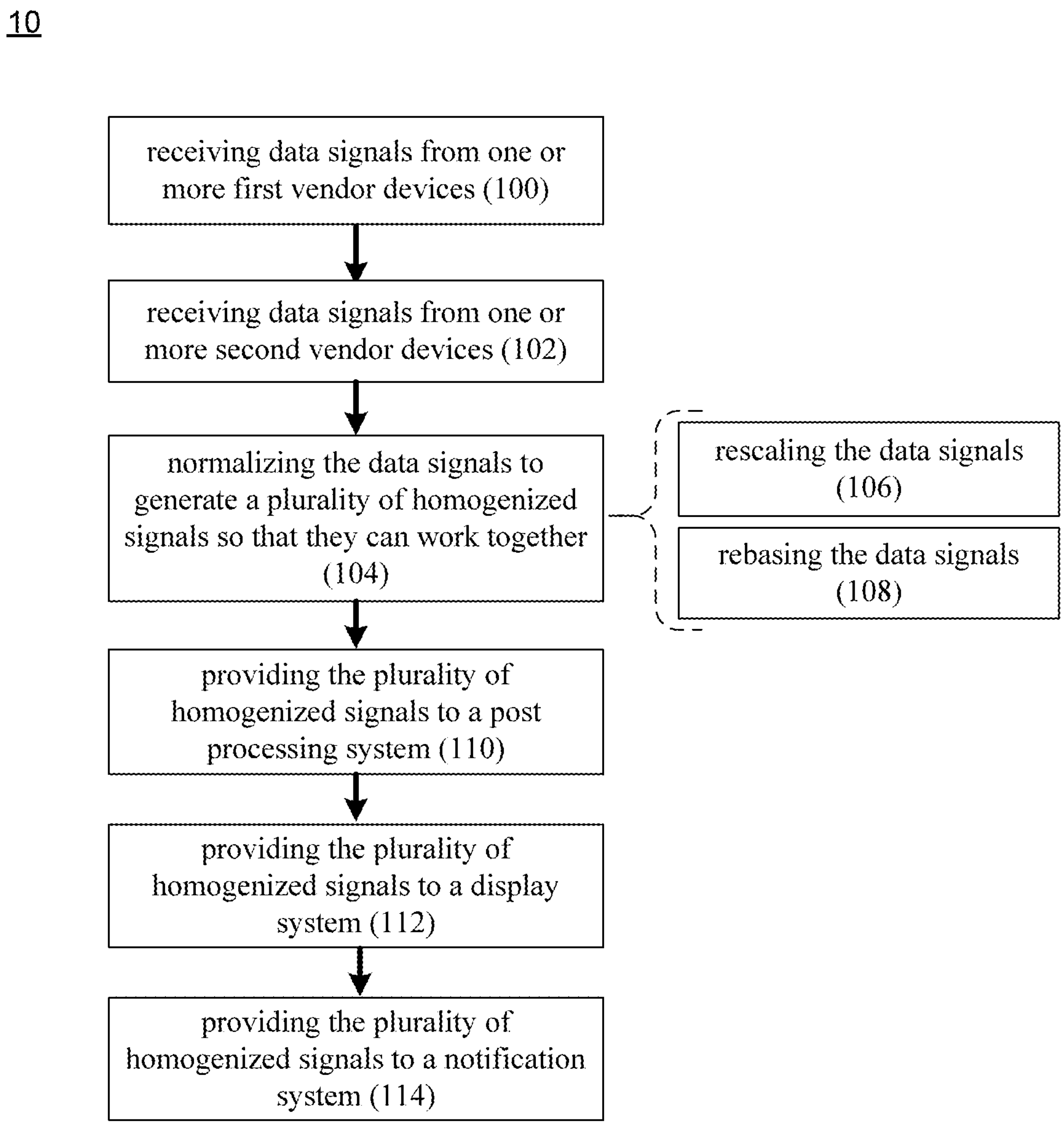
FIG. 2 is a flowchart of the information process of FIG. 1 according to an embodiment of the present disclosure.
Figure 3:
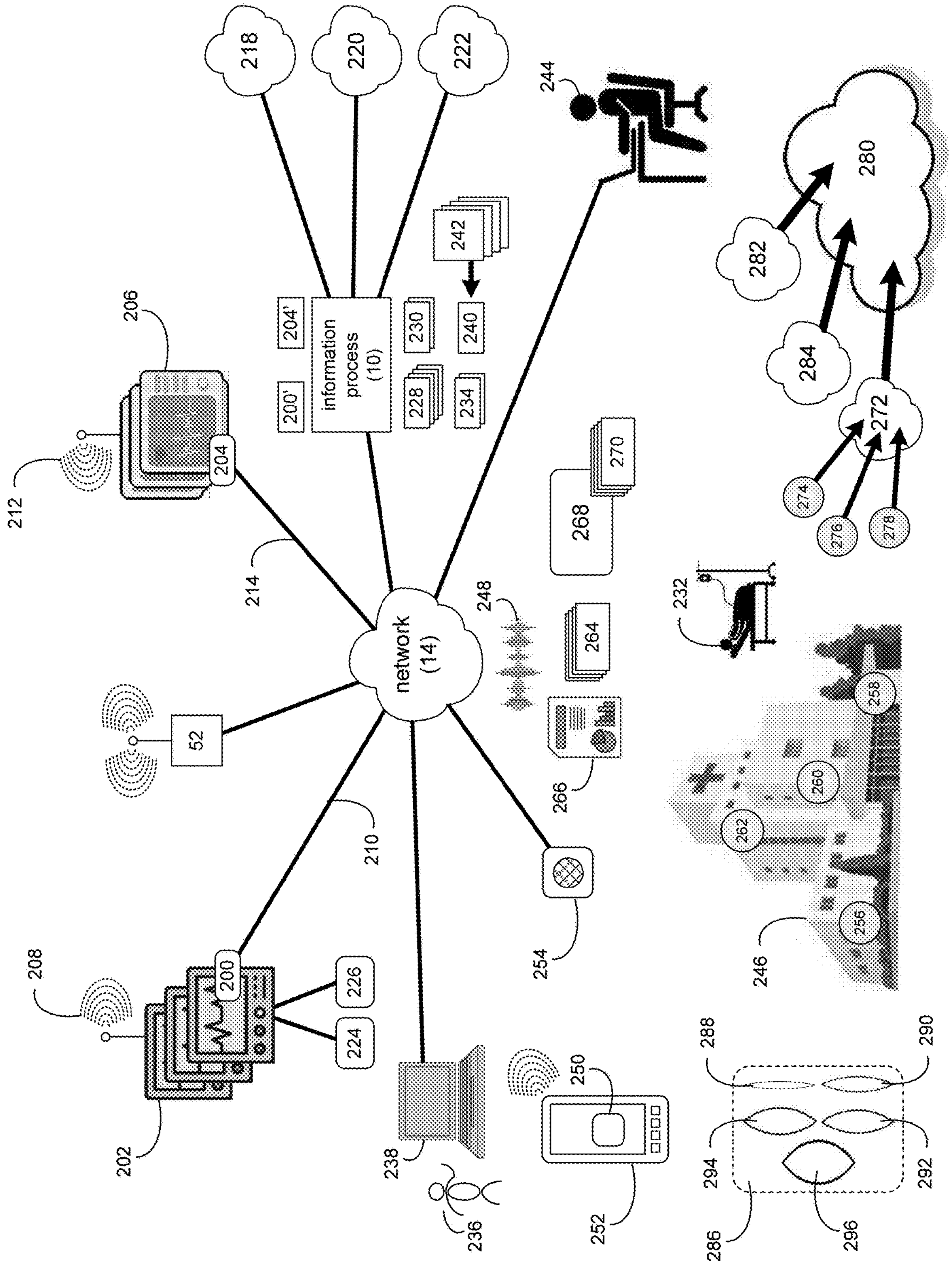
FIG. 3 is a diagrammatic view of multiple devices coupled to the information process of FIG. 1 according to an embodiment of the present disclosure.

Referring also to FIGS. 2-3, information process 10 may receive 100 data signals (e.g., data signals 200) from one or more first vendor devices (e.g., first vendor devices 202) and may receive 102 data signals (e.g., data signals 204) from one or more second vendor devices (e.g., second vendor devices 206). Generally speaking, the data signals (e.g., data signals 200, 204) may concern one or more details of the one or more first vendor devices (e.g., first vendor devices 202) and/or the one or more second vendor devices (e.g., second vendor devices 206). Additionally/alternatively, the data signals (e.g., data signals 200, 204) may concern one or more uses of the one or more first vendor devices (e.g., first vendor devices 202) and/or the one or more second vendor devices (e.g., second vendor devices 206).

The one or more first vendor devices (e.g., first vendor devices 202) may be coupled to information process 10 via e.g., wireless communication channel 208 established between the one or more first vendor devices (e.g., first vendor devices 202) and e.g., wireless access point (i.e., WAP) 52. Additionally/alternatively, the one or more first vendor devices (e.g., first vendor devices 202) may be coupled to information process 10 via e.g., wired connection 210 established between the one or more first vendor devices (e.g., first vendor devices 202) and e.g., network 14.

The one or more second vendor devices (e.g., second vendor devices 206) may be coupled to information process 10 via e.g., wireless communication channel 212 established between the one or more second vendor devices (e.g., second vendor devices 206) and e.g., wireless access point (i.e., WAP) 52. Additionally/alternatively, the one or more second vendor devices (e.g., second vendor devices 206) may be coupled to information process 10 via e.g., wired connection 214 established between the one or more second vendor devices (e.g., second vendor devices 206) and e.g., network 14.

The one or more first vendor devices (e.g., first vendor devices 202) and/or the one or more second vendor devices (e.g., second vendor devices 206) may include one or more of: a medical device, a process control device, a networking device, a computing device, a manufacturing device, an agricultural device, an energy/refining device, an aerospace device, a forestry device, and a defense device. Generally speaking, these vendor devices (e.g., first vendor devices 202 and/or second vendor devices 206) may be electrically coupled to information process 10 so that these vendor devices (e.g., first vendor devices 202 and/or second vendor devices 206) may provide the data signals (e.g., data signals 200 and/or data signals 204) to information process 10.

Examples of MEDICAL DEVICES may include but are not limited to instruments, apparatuses, machines, implants, or any other similar items used in the diagnosis, prevention, monitoring, treatment, or alleviation of diseases, injuries, or disabilities in humans. These devices are specifically designed to serve medical purposes and are regulated by health authorities to ensure their safety and effectiveness.

Medical devices can range from simple tools such as thermometers and stethoscopes to more complex equipment like magnetic resonance imaging (MRI) machines, artificial organs, or robotic surgical systems. They are used by healthcare professionals, patients, or caregivers in various healthcare settings, including hospitals, clinics, laboratories, and even at home.

Examples of medical devices may include but are not limited to:

- Diagnostic Devices: These devices are used to identify diseases or medical conditions. Examples include X-ray machines, ultrasound scanners, blood pressure monitors, and glucose meters.
- Therapeutic Devices: These devices are used to treat or manage medical conditions. Examples include pacemakers, insulin pumps, dialysis machines, and prosthetic limbs.
- Surgical Instruments: These devices are used during surgical procedures to perform specific tasks. Examples include scalpels, forceps, surgical lasers, and laparoscopic instruments.
- Implants: These devices are surgically placed in the body to support or replace a specific function. Examples include artificial joints, dental implants, cardiac stents, and cochlear implants.
- Assistive Devices: These devices help individuals with disabilities or limitations to improve their mobility or perform daily activities. Examples include wheelchairs, hearing aids, walkers, and canes.
- Monitoring Devices: These devices are used to track and monitor vital signs or specific health parameters. Examples include electrocardiograms (ECGs), pulse oximeters, sleep apnea monitors, and continuous glucose monitors.

It's important to note that the classification and regulation of medical devices may vary by country or region. Regulatory agencies, such as the U.S. Food and Drug Administration (FDA) in the United States, oversee the approval, safety, and quality of medical devices to ensure they meet the necessary standards for patient care.

Examples of PROCESS CONTROL DEVICES (also known as industrial control devices) may include but are not limited to instruments or equipment used to monitor and regulate industrial processes to achieve desired outcomes such as efficiency, quality, safety, and consistency. These devices are commonly employed in manufacturing, chemical processing, power generation, oil and gas refining, and other industrial sectors. They help automate and optimize processes, ensuring they operate within defined parameters and maintain desired conditions.

Examples of process control devices may include but are not limited to:

- Programmable Logic Controllers (PLCs): PLCs are versatile digital computers that automate and control electromechanical processes. They receive input signals from sensors, make decisions based on pre-programmed logic, and send output signals to actuators to control machinery or equipment.
- Distributed Control Systems (DCS): DCSs are comprehensive control systems used in large-scale industrial processes. They consist of multiple control units interconnected with sensors, actuators, and other devices. DCSs enable centralized monitoring and control of various process variables across a plant or facility.
- Human-Machine Interface (HMI): HMIs provide a graphical interface for operators to interact with process control systems. They display real-time data, process status, alarms, and allow operators to input commands or adjust parameters. HMIs can be touchscreens, keypads, or other user-friendly interfaces.
- Sensors and Transmitters: These devices are used to measure physical or chemical variables such as temperature, pressure, flow rate, level, pH, conductivity, and more. They convert these measurements into electrical signals that can be interpreted and used for control purposes.
- Actuators: Actuators are devices responsible for converting control signals into physical action. They control valves, motors, pumps, and other equipment to adjust flow rates, pressures, positions, or other process parameters based on control system inputs.
- Data Acquisition Systems: These systems collect and record data from sensors, devices, and instruments at various points in the process. They store this data for analysis, monitoring, and historical reference to optimize process performance and troubleshoot issues.
- Control Valves: Control valves regulate fluid flow or pressure in a process. They receive signals from the control system and adjust their position or aperture to achieve the desired setpoint.
- Analytical Instruments: These instruments measure and analyze chemical properties or composition in a process. Examples include pH meters, gas analyzers, spectrometers, and chromatographs.

Process control devices work together to enable real-time monitoring, analysis, and adjustment of industrial processes. They help improve efficiency, reduce errors, enhance safety, and ensure consistent product quality in a wide range of industries.

Examples of NETWORKING DEVICES may include but are not limited to hardware or software components that facilitate communication and connectivity within a computer network. These devices enable the transmission, routing, and management of data across networks, allowing devices to communicate and share resources effectively. Networking devices play a crucial role in establishing and maintaining network infrastructure and connectivity.

Examples of networking devices may include but are not limited to:

- Routers: Routers are essential devices that connect multiple networks and facilitate the transfer of data between them. They determine the optimal path for data packets to reach their destination based on network addressing and routing protocols.

Switches: Switches are used to connect devices within a local area network (LAN). They receive data packets and forward them to the appropriate destination device based on the device's MAC (Media Access Control) address. Switches help improve network performance by enabling efficient data transfer between connected devices.

Hubs: Hubs are simple network devices that operate at the physical layer of a network. They receive incoming data packets and broadcast them to all connected devices. However, unlike switches, hubs do not have the capability to selectively forward data to specific devices.

Modems: Modems are used to connect a network to an external network or the Internet. They convert digital data from a computer into analog signals suitable for transmission over telephone lines (in the case of dial-up modems) or digital signals for broadband connections.

Network Interface Cards (NICs): NICs are hardware components installed in computers or devices to connect them to a network. They provide the necessary interface for devices to transmit and receive data over the network.

Wireless Access Points (WAPs): WAPs enable wireless connectivity within a network. They serve as a central hub for wireless devices to connect to a wired network, providing wireless access and facilitating communication between wireless devices and the network.

Firewalls: Firewalls are security devices that monitor and control incoming and outgoing network traffic based on predetermined security rules. They help protect networks from unauthorized access, threats, and malicious activities.

Network Bridges: Bridges connect two or more LANs or network segments and facilitate communication between them. They operate at the data link layer of the network and can help extend network coverage or segment networks to improve performance and security.

Network Load Balancers: Load balancers distribute network traffic across multiple servers or network links to optimize resource usage, improve performance, and ensure high availability of network services.

Network Print Servers: Print servers enable network printers to be shared and accessed by multiple users within a network. They manage print jobs, print queues, and provide print services to network-connected devices.

These are just a few examples of networking devices commonly used in computer networks. The combination and configuration of these devices depend on the specific requirements of the network and the desired functionality.

Examples of COMPUTING DEVICES may include but are not limited to electronic devices that process and manipulate data using computational capabilities. These devices are designed to perform various tasks, ranging from basic calculations to complex computations and data processing. Computing devices come in different forms and sizes, each tailored for specific purposes and user needs.

Examples of computing devices may include but are not limited to:

Personal Computers (PCs): Personal computers are general-purpose computing devices designed for individual use. They consist of a central processing unit (CPU), memory, storage devices, input/output peripherals (keyboard, mouse, display), and an operating system. PCs are versatile devices used for tasks such as browsing the web, word processing, gaming, multimedia, and more.

Laptops: Laptops are portable computing devices that provide the same functionality as personal computers. They incorporate a keyboard, display, and a built-in battery, allowing users to work or perform tasks on the go.

Tablets: Tablets are lightweight, portable devices with touchscreens and simplified user interfaces. They offer functionality similar to laptops but with a more compact and intuitive design. Tablets are commonly used for web browsing, media consumption, e-books, and mobile applications.

Smartphones: Smartphones are mobile computing devices that combine telephony capabilities with computing features. They offer advanced functionality, including internet access, email, multimedia, applications, and various sensors. Smartphones have become an essential part of modern life, providing communication, entertainment, and productivity features.

Servers: Servers are powerful computing devices designed to manage and process vast amounts of data and provide services to other devices or users. They are typically used in network environments to store and deliver data, host websites and applications, handle database management, and perform complex computations.

Workstations: Workstations are high-performance computing devices optimized for specialized tasks such as computer-aided design (CAD), video editing. 3D rendering, scientific simulations, and engineering. They typically have advanced processing power, enhanced graphics capabilities, and extensive memory capacity.

Embedded Systems: Embedded systems are specialized computing devices embedded within other systems or products. They are designed to perform specific functions and are often found in automobiles, appliances, medical equipment, industrial machinery, and other devices that require computing capabilities.

Wearable Devices: Wearable devices are computing devices worn on the body or integrated into clothing or accessories. Examples include smartwatches, fitness trackers, augmented reality glasses, and medical monitoring devices. These devices offer features such as health tracking, notifications, communication, and interaction with other devices.

Gaming Consoles: Gaming consoles are computing devices specifically designed for playing video games. They provide dedicated hardware and software platforms optimized for gaming, often with advanced graphics processing capabilities.

Internet of Things (IOT) Devices: IoT devices are computing devices embedded in everyday objects, connected to the internet, and capable of collecting and exchanging data. Examples include smart home devices, environmental sensors, industrial sensors, and connected appliances.

These are just a few examples of computing devices, each serving different purposes and catering to various computing needs. The computing landscape is continually evolving, with new devices and technologies being developed to meet changing user requirements.

Examples of MANUFACTURING DEVICES (also known as industrial manufacturing equipment) may include but are not limited to specialized machines, tools, and systems used in the production and manufacturing processes across various industries. These devices are designed to automate, optimize, and facilitate the manufacturing of products with efficiency, precision, and consistency. Manufacturing devices are employed in sectors such as automotive, electronics, pharmaceuticals, food processing, textiles, and more.

Examples of manufacturing devices may include but are not limited to:

CNC Machines: Computer Numerical Control (CNC) machines are automated machining tools that follow pre-programmed instructions to shape and cut materials with high precision. Examples include CNC milling machines, lathes, routers, and laser cutting machines.

Robotics and Automation Systems: Robotic devices and automation systems are used to automate repetitive tasks, assembly processes, material handling, and packaging. Industrial robots are programmable machines that perform tasks with speed, accuracy, and consistency, improving productivity and reducing human error.

Assembly Machines: These devices are specifically designed to automate assembly processes by joining and fastening components together. Examples include robotic arms, pick-and-place machines, and specialized assembly line systems.

3D Printers: Also known as additive manufacturing machines, 3D printers build three-dimensional objects by layering materials based on digital models. They enable the rapid prototyping, customization, and small-scale production of components or products.

Industrial Sewing Machines: These machines are used in textile and garment manufacturing to stitch fabrics and create finished products such as clothing, upholstery, and accessories. Industrial sewing machines offer enhanced speed, durability, and specialized stitching capabilities.

Injection Molding Machines: Injection molding machines melt and inject molten materials, typically plastics, into molds to produce a wide range of products and components. They are used in industries such as automotive, packaging, consumer goods, and medical devices.

Packaging Machines: Packaging machines automate the process of packaging products for distribution and sale. They can handle tasks like filling, sealing, labeling, and palletizing. Examples include form-fill-seal machines, blister packaging machines, and cartoning machines.

Inspection and Quality Control Devices: These devices are used to inspect and ensure the quality of manufactured products. They include tools like coordinate measuring machines (CMM), vision inspection systems, gauges, and sensors to detect defects, measure dimensions, and verify product specifications.

Material Handling Equipment: Material handling devices such as conveyor systems, automated guided vehicles (AGVs), forklifts, and robotic arms facilitate the movement, storage, and transportation of materials within the manufacturing facility.

Testing and Measurement Devices: Testing and measurement devices are used to assess the performance, functionality, and quality of manufactured products. Examples include hardness testers, spectrometers, oscilloscopes, and gauges.

These are just a few examples of manufacturing devices, and the specific devices used depend on the industry, production processes, and product requirements. Manufacturing devices help streamline production, increase efficiency, improve product quality, and reduce costs, contributing to the overall success and competitiveness of manufacturing operations.

Examples of AGRICULTURAL DEVICES (also known as farm equipment or agricultural machinery) may include but are not limited to specialized tools, machines, and equipment designed to assist in various tasks related to agricultural practices. These devices are used by farmers and agricultural workers to automate, enhance efficiency, and improve productivity in agricultural activities. Agricultural devices are utilized across different stages of farming, including land preparation, planting, cultivation, irrigation, harvesting, and post-harvest processing.

Examples of agricultural devices may include but are not limited to:

Tractors: Tractors are versatile vehicles used for multiple farming tasks. They are equipped with powerful engines and provide the necessary power and traction to perform tasks like plowing, tilling, planting, hauling, and spraying. Tractors can also be combined with various attachments and implements to carry out specific tasks.

Harvesters: Harvesters are machines designed to efficiently harvest crops such as grains, fruits, vegetables, and oilseeds. Different types of harvesters exist for specific crops, including combine harvesters for cereal crops, potato harvesters, grape harvesters, and cotton pickers.

Planters and Seeders: Planters and seeders are devices used to sow seeds in a controlled and efficient manner. They distribute seeds evenly at precise depths and spacing, ensuring optimal plant growth and yield. Planters and seeders can be manual, animal-drawn, or tractor-mounted, depending on the scale of farming operations.

Irrigation Systems: Irrigation devices are used to deliver water to crops in a controlled manner, ensuring proper moisture levels for growth. These systems include sprinklers, drip irrigation systems, center pivot irrigation systems, and furrow irrigation systems. They help conserve water, improve crop yield, and reduce labor requirements.

Sprayers: Sprayers are used to apply fertilizers, pesticides, herbicides, and other agricultural chemicals to crops. They can be handheld, backpack-mounted, or tractor-mounted, equipped with spray nozzles and tanks to evenly distribute the substances and protect crops from pests, diseases, and weeds.

Plows and Tillage Equipment: Plows and tillage equipment are used for primary tillage and land preparation. Plows break up and turn over the soil, while tillage equipment further cultivates the soil, preparing it for planting. Implements like moldboard plows, disc harrows, and cultivators fall under this category.

Livestock Equipment: Livestock equipment includes devices used in animal husbandry and management. Examples include feeding equipment, milking machines, animal handling systems, and barn ventilation systems. These devices contribute to the care, health, and productivity of livestock.

Grain Handling and Storage Equipment: Grain handling devices such as grain elevators, grain dryers, and silos are used to safely store, transport, and process harvested grains. They facilitate efficient storage, drying, and handling of grains to preserve their quality and prevent spoilage.

Hay and Forage Equipment: Hay and forage devices are used to harvest, process, and store animal feed. They include equipment such as hay balers, forage choppers, hay rakes, and bale wrappers.

Post-Harvest Processing Equipment: Post-harvest processing devices are used to clean, sort, grade, and process harvested agricultural products. Examples include threshers, sorters, graders, grain mills, and fruit and vegetable processing equipment.

These are just a few examples of agricultural devices. The specific devices used may vary depending on factors such as the type of crop, farming practices, scale of operations, and regional variations. Agricultural devices play a crucial role in modern farming, improving efficiency, productivity, and sustainability in the agricultural industry.

Examples of ENERGY/REFINING DEVICES may include but are not limited to specialized equipment and systems used in the energy industry, particularly in the refining and processing of various energy sources. These devices are crucial for extracting, converting, refining, and distributing energy resources in different forms, such as oil, natural gas, coal, and renewable energy sources. They are utilized in power plants, refineries, and other energy production and distribution facilities.

Examples of energy and refining devices may include but are not limited to:

Refining Equipment: Refining devices are used in oil refineries to process crude oil into various refined products such as gasoline, diesel, jet fuel, lubricants, and other petroleum-based products. Examples include distillation towers, catalytic converters, hydrotreaters, and fluid catalytic cracking units (FCCUs).

Boilers and Furnaces: Boilers and furnaces are devices used in power plants and industrial facilities to generate steam or heat. They burn fossil fuels or use other energy sources to produce high-pressure steam that drives turbines and generates electricity.

Turbines and Generators: Turbines, such as steam turbines, gas turbines, and wind turbines, convert the kinetic energy of a fluid or gas into mechanical energy. They are coupled with generators to produce electrical energy. Turbines and generators are key components in power generation systems.

Solar Panels: Solar panels, also known as photovoltaic panels, convert sunlight into electrical energy. They consist of interconnected solar cells that generate direct current (DC) electricity when exposed to sunlight. Solar panels are used in solar power systems to produce renewable energy.

Wind Turbines: Wind turbines capture the kinetic energy of the wind and convert it into electrical energy. They consist of large rotor blades that spin a generator when the wind blows. Wind turbines are used in wind farms and off-grid applications to generate clean and renewable energy.

Natural Gas Processing Equipment: Natural gas processing devices are used to extract and process natural gas from its sources. They include equipment such as compressors, separators, dehydrators, and gas sweetening units. These devices remove impurities and separate valuable components like methane, ethane, propane, and butane.

Power Distribution Equipment: Power distribution devices include transformers, switchgear, circuit breakers, and distribution panels. They are used to control and distribute electrical energy from power plants to various end-users, such as homes, businesses, and industrial facilities.

Energy Storage Systems: Energy storage devices store excess energy generated during periods of low demand and release it during peak demand or when renewable energy sources are unavailable. Examples include battery storage systems, pumped storage hydropower, and compressed air energy storage (CAES) systems.

Heat Exchangers: Heat exchangers transfer thermal energy between two or more fluids at different temperatures. They are used in various energy and refining processes to recover waste heat, facilitate heat exchange, and improve energy efficiency.

Pipelines and Storage Tanks: Pipelines and storage tanks are essential for transporting and storing energy resources like oil, natural gas, and petroleum products. Pipelines transport these resources over long distances, while storage tanks provide temporary storage and distribution hubs.

These are just a few examples of energy and refining devices. The energy industry is diverse, with a wide range of technologies and equipment used to produce, refine, and distribute different forms of energy. Advances in technology and the growing focus on renewable energy sources continue to drive innovation in this field.

Examples of AEROSPACE DEVICES may include but are not limited to specialized equipment, systems, and vehicles used in the aerospace industry, which encompasses the design, development, production, and operation of aircraft and spacecraft. These devices are designed to enable flight, exploration of space, and various aerospace-related activities. They include a wide range of components, instruments, and systems that are critical for aerospace operations.

Examples of aerospace devices may include but are not limited to:

Aircraft: Aircraft are vehicles designed to fly within the Earth's atmosphere. They include various types such as airplanes, helicopters, gliders, and unmanned aerial vehicles (UAVs). Aircraft devices encompass airframes, engines, avionics systems, landing gear, control surfaces, and onboard instruments necessary for navigation, control, and communication.

Spacecraft: Spacecraft are vehicles designed for space exploration and satellite deployment. They include crewed spacecraft, such as capsules and space shuttles, as well as robotic spacecraft, such as satellites, probes, and rovers. Spacecraft devices include propulsion systems, life support systems, communication systems, scientific instruments, solar panels, and heat shields.

Rocket Engines: Rocket engines are used to propel spacecraft and launch vehicles into space. They operate on the principle of expelling high-speed exhaust gases to generate thrust. Rocket engines include components such as combustion chambers, nozzles, propellant tanks, and turbopumps.

Avionics Systems: Avionics systems refer to the electronic systems used in aircraft for navigation, communication, flight control, and monitoring. They include devices such as flight computers, navigation systems (GPS), radar systems, communication systems, autopilots, and cockpit displays.

Aircraft Engines: Aircraft engines provide the necessary thrust to propel aircraft through the air. They include various types such as turbojet engines, turboprop engines, turbofan engines, and turboshaft engines. Aircraft engines are complex devices comprising components such as combustion chambers, turbines, compressors, and fuel systems.

Control Systems: Aerospace control systems are crucial for maneuvering, stability, and control of aircraft and spacecraft. They include flight control surfaces, such as ailerons, elevators, and rudders, as well as systems like fly-by-wire, autopilots, and attitude control thrusters for spacecraft.

Satellite Systems: Satellite systems consist of components and devices used for communication, navigation, remote sensing, and scientific research. They include satellite buses (platforms), payloads (instruments), antennas, solar panels, attitude control systems, and telemetry systems.

Parachutes: Parachutes are devices used for deceleration and landing of aircraft, spacecraft, or payloads. They are crucial for safe re-entry and recovery of crewed spacecraft, as well as for cargo or personnel airdrops.

Ground Support Equipment: Ground support equipment refers to the devices used on the ground to support aerospace operations. Examples include aircraft ground handling equipment, such as tugs, loaders, and fueling systems, as well as launch pad equipment for spacecraft, such as umbilical towers, gantries, and fueling systems.

Flight Simulators: Flight simulators are devices used for pilot training, aircraft system testing, and research. They provide a simulated environment that replicates the experience of flying an aircraft, including the cockpit controls, instruments, and visual displays.

These are just a few examples of aerospace devices, and the aerospace industry encompasses a vast array of technologies and equipment. The development and utilization of these devices enable advancements in aviation, space exploration, satellite communication, and scientific research.

Examples of FORESTRY DEVICES may include but are not limited to specialized tools, equipment, and machinery used in the field of forestry for various tasks related to the management, harvesting, and processing of trees and forests. These devices are designed to improve efficiency, safety, and productivity in forestry operations. They are used by foresters, loggers, and other professionals involved in forest management and timber production.

Examples of forestry devices may include but are not limited to:

Chainsaws: Chainsaws are portable mechanical saws powered by either electricity, gasoline, or battery. They are used for felling trees, limbing, bucking (cutting felled trees into logs), and other tree-cutting operations in the forest.

Harvesters: Harvesters are specialized forestry machines designed for felling, delimbing, and processing trees in a single operation. They can fell, strip branches, and cut trees into logs, significantly reducing manual labor and increasing productivity.

Forwarders: Forwarders are purpose-built vehicles used to transport logs and other forest products from the cutting site to a central location, typically a log landing or a roadside collection point. They have a loading area and a crane for lifting and loading logs onto the vehicle.

Skidders: Skidders are heavy-duty machines used to extract logs from the forest and drag them to a landing or a loading area. They have large grapple arms or winches to grip and lift logs for transportation.

Logging Trucks: Logging trucks are specialized trucks used to transport logs from the forest to sawmills or other processing facilities. They are designed with trailers and secure load-holding structures to transport logs safely and efficiently.

Mulchers: Mulchers are machines used to clear vegetation, shrubs, and small trees in forestry operations. They are equipped with rotating blades or hammers that shred vegetation, enabling land clearing and site preparation.

Portable Sawmills: Portable sawmills are compact and transportable machines used for on-site processing of logs into lumber. They allow for immediate sawing of felled trees, reducing transportation costs and time to the sawmill.

Chippers: Chippers are devices used to process tree branches, limbs, and other forestry residues into wood chips. Wood chips are used for various purposes, including fuel, landscaping, and the production of pulp and paper.

Tree Planters: Tree planters are devices used for efficient tree planting in reforestation and afforestation projects. They can dig holes, place seedlings, and cover them with soil, improving the speed and accuracy of tree planting operations.

Forest Firefighting Equipment: Forest firefighting equipment includes devices like fire pumps, hoses, and fire suppression tools used to combat and control forest fires. They are crucial for protecting forests and minimizing the damage caused by wildfires.

These are just a few examples of forestry devices, and the specific devices used may vary depending on factors such as the type of forestry operation, terrain, tree species, and regional practices. Forestry devices play a vital role in sustainable forest management, timber production, and environmental conservation.

Examples of DEFENSE DEVICES (also known as military devices or weapons systems) may include but are not limited to specialized equipment, technologies, and systems designed and utilized by military forces for defense and security purposes. These devices are designed to protect a country's interests, deter potential threats, and ensure the safety of military personnel and civilians. Defense devices encompass a wide range of technologies and equipment used for various defense applications.

Examples of defense devices may include but are not limited to:

Firearms: Firearms include various handheld weapons designed to launch projectiles using the force of expanding high-pressure gases. They encompass rifles, pistols, machine guns, and shotguns, which are used by military personnel for individual combat or close-quarters engagements.

Artillery: Artillery devices are heavy guns or cannons used for long-range indirect fire support. They can fire explosive projectiles or provide suppressive fire. Examples include howitzers, mortars, and rocket launchers.

Missiles: Missiles are self-propelled weapons that can be guided to specific targets. They can be launched from ground-based systems, ships, submarines, aircraft, or launched from portable platforms. Missiles include surface-to-air missiles (SAMs), surface-to-surface missiles (SSMs), anti-ship missiles, and air-to-air missiles (AAMs).

Tanks: Tanks are heavily armored tracked vehicles equipped with powerful cannons. They are used for ground combat and provide offensive and defensive capabilities on the battlefield. Tanks combine firepower, mobility, and protection.

- Fighter Aircraft: Fighter aircraft are high-performance military aircraft designed for air-to-air combat and ground attack missions. They are equipped with advanced avionics, radar systems, missiles, and guns for air superiority and tactical strikes.
- Warships: Warships include naval vessels designed for combat operations at sea. They range from aircraft carriers, destroyers, and frigates to submarines and patrol boats. Warships are equipped with various weapon systems, including missiles, naval guns, torpedoes, and anti-aircraft systems.
- Unmanned Aerial Vehicles (UAVs): UAVs, also known as drones, are remotely piloted or autonomous aircraft used for reconnaissance, surveillance, and targeted strikes. They provide real-time intelligence and can be armed with missiles or bombs.
- Electronic Warfare Systems: Electronic warfare devices encompass a range of systems used to detect, deceive, disrupt, and counter enemy electronic systems. They include radar jammers, signal intelligence equipment, electronic countermeasures, and defensive systems to protect against cyber threats.
- Ballistic Missile Defense Systems: Ballistic missile defense devices are designed to detect, track, and intercept incoming ballistic missiles. These systems employ sensors, radars, interceptor missiles, and command and control systems to protect against missile threats.
- Protective Gear: Protective gear includes devices such as body armor, helmets, gas masks, and protective clothing worn by military personnel to provide protection against physical, ballistic, and chemical threats in combat situations.

These are just a few examples of defense devices. The defense industry is highly advanced and continuously evolving, driven by technological advancements and strategic needs. It encompasses a vast array of devices and systems tailored to meet the specific requirements of modern military forces.

Information process 10 may normalize 104 the data signals (e.g., data signals 200 and/or data signals 204) to generate a plurality of homogenized signals (e.g., data signals 200' and/or data signals 204') so that the data signals (e.g., data signals 200 and/or data signals 204) can work together.

For example and when normalizing data, information process 10 may transform data into a standardized format or range, which may involve adjusting the values of a dataset to a common scale, typically between 0 and 1 or −1 and 1, wherein the goal of data normalization is to eliminate the effects of varying scales, units, or distributions within the data, allowing for fairer comparisons and more accurate analysis.

Normalization is particularly useful when working with datasets that have different measurement units or widely varying ranges. By bringing all the data to a common scale, normalization enables meaningful comparisons and helps algorithms or models to better interpret and process the data, as it may prevent certain features from dominating the analysis or introducing bias due to their larger magnitude.

Examples of methods of normalizing data may include but are not limited to:

- Min-Max Normalization (also known as feature scaling): This method scales the data linearly to a specific range, often between 0 and 1. It involves subtracting the minimum value of the feature and then dividing by the range (i.e., the difference between the maximum and minimum values). The formula for Min-Max normalization is: normalized_value=(x−min(x))/(max(x)−min(x))
- Z-Score Normalization (also known as standardization): This method transforms the data to have a mean of 0 and a standard deviation of 1. It involves subtracting the mean value of the feature and dividing by the standard deviation. The formula for Z-Score normalization is: normalized_value=(x−mean(x))/standard_deviation(x)
- Decimal Scaling: In this method, the data is scaled by shifting the decimal point of each value. The number of decimal places to shift is determined based on the maximum absolute value in the dataset.

For example and when normalizing 104 the data signals (e.g., data signals 200 and/or data signals 204) to generate a plurality of homogenized signals (e.g., data signals 200' and/or data signals 204') so that the data signals (e.g., data signals 200 and/or data signals 204) can work together, information process 10 may: rescale 106 the data signals (e.g., data signals 200 and/or data signals 204); and/or rebase 108 the data signals (e.g., data signals 200 and/or data signals 204).

Rescaling data refers to the process of changing the scale or range of values in a dataset without necessarily transforming them into a specific standardized format. Unlike normalization, which typically aims to bring the data into a common scale, rescaling allows for adjustments that can be tailored to specific requirements or preferences. The goal of rescaling data is to manipulate the values in a way that preserves the relationships and distribution of the original data while fitting them into a desired range or scale. This can be useful for various reasons, such as enhancing visualization, improving algorithm performance, or accommodating specific constraints or preferences.

Examples of rescaling methods may include but are not limited to:

- Min-Max Rescaling: Similar to min-max normalization, min-max rescaling scales the data to a specific range, often between 0 and 1 or any other desired minimum and maximum values. It involves subtracting the minimum value of the feature and then dividing by the range (i.e., the difference between the maximum and minimum values). The formula for min-max rescaling is the same as in normalization: rescaled_value=(x−min(x))/(max(x)−min(x))
- Feature Scaling: Feature scaling rescales each feature (column) in a dataset independently, without considering the range of the entire dataset. It can be done using various methods, such as standardization (Z-score normalization), range scaling, or decimal scaling.
- Logarithmic Rescaling: Logarithmic rescaling involves applying a logarithmic function to the data values. This transformation can compress the scale of large values while expanding the scale of small values. Logarithmic rescaling is often useful when dealing with data that spans several orders of magnitude or has a skewed distribution.
- Power Rescaling: Power rescaling applies a power function to the data values. It can be useful for adjusting the scale of values that are disproportionately large or small. By raising the values to a power, such as squaring or taking the square root, the scale can be modified accordingly.

Rescaling data allows for flexible adjustments to meet specific needs or preferences. However, it's important to note that rescaling does not necessarily eliminate the differences in distribution or units of measurement among features. The choice of rescaling method should be based on the characteristics of the data and the objectives of the analysis or modeling task.

Rebasing data refers to the process of recalculating or adjusting the values of a dataset with respect to a new base or reference point. It involves shifting the entire dataset by a certain amount or percentage to establish a different baseline or starting point for the data. The purpose of rebasing data is often to facilitate comparisons, identify trends, or analyze changes relative to a specific reference point. By rebasing the data, you can normalize it with respect to a chosen base and evaluate the relative changes or growth rates in the values.

The rebasing process may involve the following steps:

Selecting a Base Period: Choose a specific time period or reference point that will serve as the new base or starting point for the data. This period is often set to a specific date, such as the beginning of a year or a particular milestone.

Calculating the Rebased Values: Subtract or adjust the original values of the dataset by the difference between the chosen base period and the original base period. This adjustment aligns the data with the new base period and establishes the rebased values.

Expressing Rebased Values: Express the rebased values as indices or ratios relative to the base period. For example, if the base period has a rebased value of 100, other periods' values will be expressed relative to that base (e.g., 105 means a 5% increase from the base).

Rebasing can be useful in various scenarios, such as financial analysis, economic indicators, or market indices. It allows for a clearer understanding of relative changes over time and facilitates comparisons across different periods or entities.

As discussed above, information process 10 may be utilized to function as an intermediary between devices that are offered by multiple vendors, wherein information process 10 may be configured to effectuate communication between devices produced by different vendors. Accordingly and by performing the operations discussed above (e.g., normalizing, rescaling, rebasing), the various devices can now exchange information. Accordingly, information in the form of homogenized signals (e.g., data signals 200' and/or data signals 204') may be exchanged: between devices (e.g., first vendor devices 202 and/or second vendor devices 206), from devices (e.g., first vendor devices 202 and/or second vendor devices 206) to information process 10, and from information process 10 to devices (e.g., first vendor devices 202 and/or second vendor devices 206); thus enabling the free exchange of information/data, the remote control of such devices (e.g., first vendor devices 202 and/or second vendor devices 206), the remote adjustment of such devices (e.g., first vendor devices 202 and/or second vendor devices 206), and the remote configuration of such devices (e.g., first vendor devices 202 and/or second vendor devices 206).

Information process 10 may provide 110 the plurality of homogenized signals (e.g., data signals 200' and/or data signals 204') to a post processing system (e.g., post processing system 218).

A post-processing system (e.g., post processing system 218) refers to a set of activities, tools, or techniques that are applied to data or output after an initial process or operation has taken place. It involves analyzing, refining, and enhancing the data or results obtained from a primary process to derive additional insights or improve the quality and usability of the output.

Post-processing systems (e.g., post processing system 218) are commonly used in various fields, including scientific research, engineering, computer graphics, data analysis, and more. They are designed to perform tasks such as data filtering, noise reduction, data visualization, data integration, feature extraction, data transformation, and result interpretation.

Examples of post-processing systems may include but are not limited to:

Image and Video Processing: In image and video processing, post-processing systems are employed to enhance the quality, remove noise or artifacts, adjust brightness or contrast, apply filters or effects, and perform image or video stabilization. These systems help to improve visual perception, extract meaningful information, or prepare the data for further analysis or presentation.

Signal Processing: Post-processing systems in signal processing deal with analyzing and modifying signals obtained from various sources. They can involve techniques like noise filtering, frequency analysis, feature extraction, signal denoising, signal reconstruction, or signal normalization. These systems help to improve the accuracy, reliability, or interpretability of signals.

Computational Modeling and Simulation: Post-processing systems are used to analyze and interpret the results obtained from computational models and simulations. They involve tasks like data visualization, data analysis, statistical analysis, identifying trends or patterns, and extracting meaningful insights from the simulation outputs. These systems aid in understanding the behavior, performance, or impact of the modeled system or phenomenon.

Data Analysis and Machine Learning: In data analysis and machine learning, post-processing systems are employed to refine and interpret the results obtained from data mining, statistical analysis, or machine learning algorithms. They can involve tasks such as data visualization, outlier detection, error correction, feature selection, result validation, or model interpretation. These systems help to extract valuable knowledge, validate the findings, or make the results more understandable and actionable.

Natural Language Processing: Post-processing systems in natural language processing deal with refining and improving the output generated by language processing algorithms. They can involve tasks like grammatical error correction, language translation, sentiment analysis, information extraction, or summarization. These systems aim to enhance the accuracy, fluency, or coherence of the processed text.

Overall, post-processing systems (e.g., post processing system 218) play a crucial role in refining, enhancing, and interpreting the results obtained from various processes or algorithms. They contribute to improving the quality, usability, and understanding of the data or output, leading to more meaningful insights and informed decision-making.

Information process 10 may provide 112 the plurality of homogenized signals (e.g., data signals 200' and/or data signals 204') to a display system (e.g., display system 220).

A display system (e.g., display system 220) refers to a combination of hardware and software components designed to present visual information or output to users. It encompasses various devices and technologies used to display images, text, graphics, videos, or other visual content for human perception.

Display systems (e.g., display system 220) are widely used in a variety of applications, including computer systems, consumer electronics, entertainment, information display, medical imaging, advertising, and more. They provide a means to visually communicate information, enhance user experience, and facilitate interaction with digital content.

Examples of display systems may include but are not limited to:

- Monitors: Monitors are the most common type of display system used in computers, laptops, and other electronic devices. They typically use liquid crystal display (LCD), light-emitting diode (LED), or organic light-emitting diode (OLED) technologies to present visual content on a flat screen.
- Projectors: Projectors are display systems that project images or video onto a large screen or surface. They use light sources and optical systems to enlarge and project the content onto a surface for viewing by a larger audience. Projectors are commonly used in classrooms, conference rooms, theaters, and home entertainment systems.
- Televisions: Televisions (TVs) are display systems specifically designed for broadcasting television programs and other video content. They come in various sizes and technologies, such as LCD, LED, OLED, or plasma, and often include additional features like smart capabilities and connectivity options.
- Head-Mounted Displays (HMDs): HMDs are wearable display systems that immerse the user in a virtual or augmented reality environment. They typically consist of a headset or glasses with integrated display screens, sensors, and audio systems. HMDs are used in gaming, simulations, training, and other immersive experiences.
- Digital Signage: Digital signage refers to display systems used for advertising, information dissemination, or wayfinding in public spaces, retail stores, transportation hubs, and other locations. These systems typically consist of large display panels or screens that can present dynamic content, including text, images, videos, and interactive elements.
- Touchscreens: Touchscreen displays combine visual output with interactive input capabilities. They allow users to interact with the displayed content by directly touching the screen. Touchscreens are used in smartphones, tablets, kiosks, interactive displays, and other devices that require user input.
- Wearable Displays: Wearable displays are integrated into wearable devices like smartwatches, fitness trackers, and smart glasses. They provide users with visual feedback, notifications, and information in a compact and portable form factor.

Display systems (e.g., display system 220) may also include additional features such as high-definition (HD) or 4K resolution, high refresh rates for smooth motion, color calibration, adjustable settings, and connectivity options to connect to various devices or networks.

Overall, display systems (e.g., display system 220) are essential components of modern technology, enabling the visual presentation of information and content in various applications, from personal devices to large-scale displays for public viewing.

Information process 10 may provide 114 the plurality of homogenized signals (e.g., data signals 200' and/or data signals 204') to a notification system (e.g., notification system 222).

A notification system (e.g., notification system 222) refers to a set of processes, tools, and technologies used to deliver alerts, messages, or updates to users or recipients. It enables the dissemination of information in a timely manner, ensuring that individuals are promptly notified about important events, changes, or actions that require their attention.

Notification systems (e.g., notification system 222) are commonly used in a wide range of contexts, including communication platforms, mobile applications, web services, enterprise systems, and more. They provide a means to notify users about various types of events, such as new messages, system status updates, reminders, alarms, security alerts, or workflow notifications.

Some key components and features of a notification system may include but are not limited to:

- Trigger: A notification system is triggered by a specific event or condition that requires user awareness or action. Triggers can include incoming messages, updates to a system, time-based events, user interactions, data changes, or predefined rules.
- Delivery Channels: Notification systems utilize various delivery channels to reach users effectively. These channels can include mobile push notifications, email, SMS text messages, in-app messages, pop-up alerts, browser notifications, voice calls, or even physical devices like pagers or smartwatches.
- Personalization and Targeting: Notification systems often allow for personalization and targeting of notifications to specific users or user groups. This ensures that notifications are relevant to the recipient's preferences, interests, or context, increasing their effectiveness and reducing unnecessary noise.
- Prioritization and Urgency: Notifications can be prioritized based on their importance or urgency. Critical alerts may require immediate attention, while less important notifications can be scheduled or displayed in a less intrusive manner.
- Customization and Preferences: Users often have the ability to customize their notification preferences, including the types of events they want to be notified about, the delivery channels they prefer, and the frequency or timing of notifications. Customization options help users tailor the notification system to their specific needs and avoid notification overload.
- Logging and History: Notification systems may maintain a log or history of sent notifications for reference or auditing purposes. This can include details such as the content, delivery time, recipient, and status of each notification.
- Feedback and Interaction: Some notification systems allow users to interact with notifications, providing options to acknowledge, dismiss, or take action directly from the notification itself. This enhances user engagement and facilitates seamless workflows.

Notification systems (e.g., notification system 222) play a crucial role in keeping users informed, engaged, and up-to-date with relevant information. They are utilized in various domains, including messaging apps, social media platforms, customer support systems, IT infrastructure monitoring, task management tools, and more. The effectiveness of a notification system depends on careful design, appropriate targeting, and respect for user preferences and privacy.

Patient Onboarding Process to Establish Patient Norms:

The following discussion concerns the manner in which information process 10 may be utilized to establish norms for a patient while onboarding the patient within a hospital. As is often the case, when a patient is initially connected to e.g., various monitoring devices within a hospital room, it may be initially unclear as to where a patient's vital signs should be (e.g., What is their normal heart rate? What is their normal respiratory rate? What is their normal blood pressure? etc.). Accordingly and as will be discussed below, information process 10 may be configured to streamline such an onboarding process.

Figure 4:
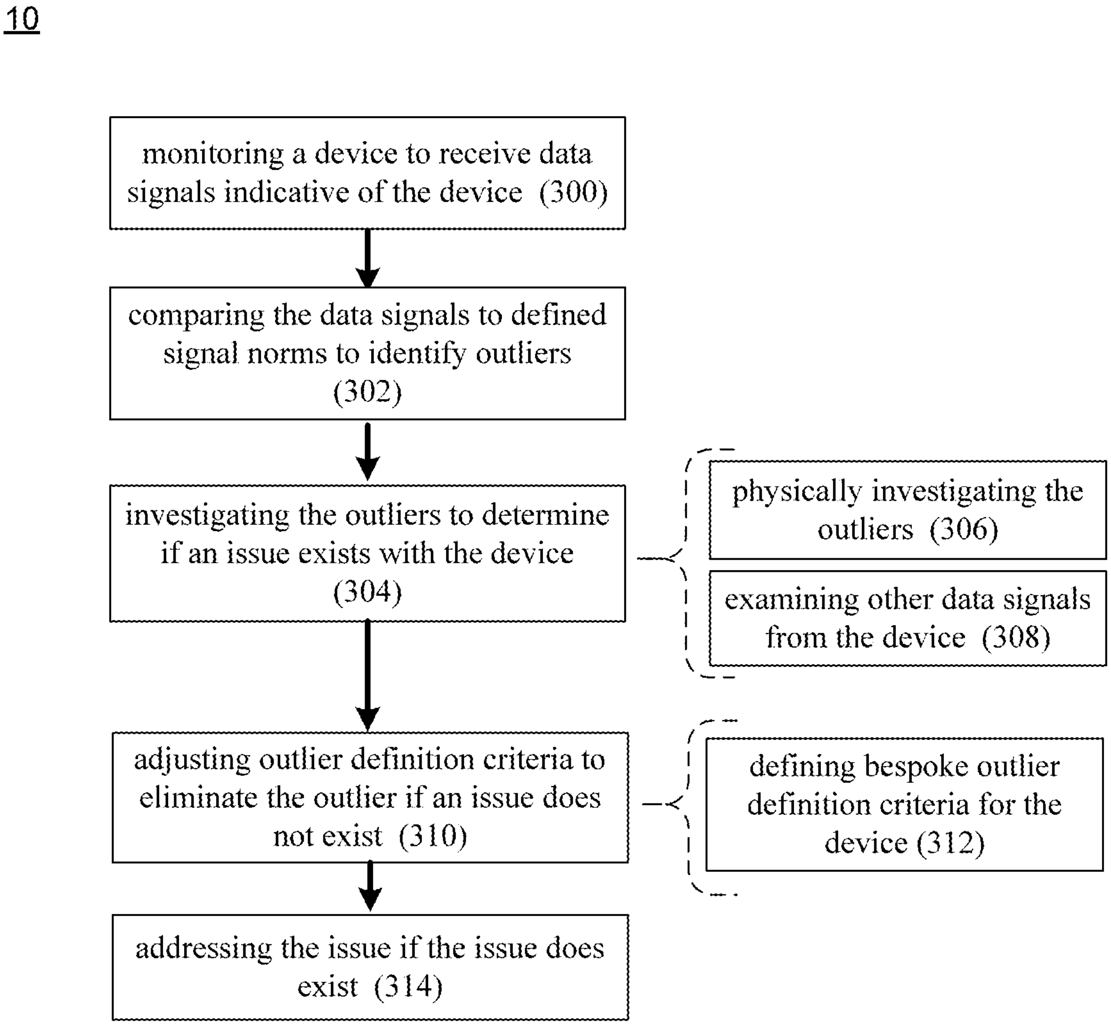
FIG. 4 is another flowchart of the information process of FIG. 1 according to an embodiment of the present disclosure.

Referring also to FIG. 4, information process 10 may monitor 300 a device (e.g., one or more of first vendor devices 202 and/or one or more of second vendor devices 206) to receive data signals (e.g., one or more of data signals 200 and/or one or more of data signals 204) indicative of the device (e.g., one or more of first vendor devices 202 and/or one or more of second vendor devices 206).

The data signals (e.g., one or more of data signals 200 and/or one or more of data signals 204) may concern one or more details of the device (e.g., one or more of first vendor devices 202 and/or one or more of second vendor devices 206) and/or uses of the device (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

As discussed above, the device (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device.

One or more of the devices (e.g., one or more of first vendor devices 202 and/or one or more of second vendor devices 206) may include one or more sub devices (e.g., sub devices 224, 226). Examples of such sub devices (e.g., sub devices 224, 226) may include any subordinate device that depends upon and/or interacts with a superior device. For example, a subordinate wireless blood gas monitor (e.g., sub device 224) and/or a subordinate wireless heart rate monitor (e.g., sub devices 226) may depend upon and/or interact with superior client vital sign monitoring device (e.g., first vendor device 202).

Information process 10 may compare 302 the data signals (e.g., one or more of data signals 200 and/or one or more of data signals 204) to defined signal norms (e.g., defined signal norms 228) to identify outliers (e.g., outliers 230).

In statistics, an outlier (e.g., outliers 230) is an observation or data point that significantly deviates from the other observations in a dataset. It is a value that lies an abnormal distance away from other data points and may be indicative of a rare or unusual occurrence, measurement error, or data entry mistake. Outliers can arise due to various reasons, such as natural variability, measurement errors, data corruption, or extreme events. Outliers can have a disproportionate impact on statistical analyses, leading to skewed results or inaccurate conclusions if not properly handled. Identifying and handling outliers is an important step in data analysis and statistical modeling. Outliers can be detected through various methods, including graphical techniques (e.g., scatter plots, box plots) or statistical tests (e.g., z-scores, modified z-scores, Mahalanobis distance).

For example, assume that the data signals (e.g., one or more of data signals 200 and/or one or more of data signals 204) concern the heart rate and respiratory rate of a patient (e.g., patient 232). Further, assuming that the patient (e.g., patient 232) is a 50-year-old male of average health, the defined signal norms (e.g., defined signal norms 228) would be a heart rate of 60-100 beats per minute and a respiratory rate of 12-20 breaths per minute. Accordingly, an outlier (e.g., outliers 230) may be a data signal (e.g., one or more of data signals 200 and/or one or more of data signals 204) that is above or below these defined signal norms (e.g., defined signal norms 228). So a heart rate of <60 beats per minute or >100 beats per minute may be considered outliers (e.g., outliers 230). Further, a respiratory rate of <12 breaths per minute or >20 breaths per minute may be considered outliers (e.g., outliers 230).

Additionally/alternatively, such defined signal norms (e.g., defined signal norms 228) may be more bespoke and individualized. So while the defined signal norms (e.g., defined signal norms 228) for a heart rate is 60-100 beats per minute and a respiratory rate is 12-20 breaths per minute; if the patient (e.g., patient 232) is a seasoned athlete of exceptional health, their "normal" heartrate may be 50-55 beats per minute and their "normal" respiratory rate may be 9-11 breaths per minute. Accordingly and in such a situation, the individual "norms" of the patient (e.g., patient 232) would consistently be outliers (e.g., outliers 230) if the societal heartrate norms and respiratory rate norms were applied to patient 232.

These defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As is known in the art, a MASSIVE DATASET, also referred to as a large-scale dataset or big dataset, is a collection of data that is exceptionally large in size and complexity. These datasets typically exceed the capacity of traditional data processing and analysis tools, requiring specialized approaches and infrastructure to handle and extract insights from them effectively.

The term "massive" is relative and can vary depending on the context and available resources. The size of a massive dataset can range from terabytes ($10^{12}$ bytes) to petabytes ($10^{15}$ bytes) or even exabytes ($10^{18}$ bytes) and beyond. Massive datasets can arise from various sources and domains, including scientific research, social media, e-commerce, financial transactions, sensor networks, genomics, astronomy, and more. They often contain a high volume of records, measurements, or observations, along with diverse data types such as text, images, videos, time series, graphs, or unstructured data.

Working with massive datasets poses several challenges, including storage, processing, analysis, and scalability. Traditional methods and tools may not be sufficient to handle these datasets efficiently. Specialized technologies and techniques, such as distributed computing, parallel processing, cloud computing, and big data frameworks (e.g., Apache Hadoop, Apache Spark), are often employed to manage and process the data at scale.

The analysis of massive datasets aims to extract meaningful insights, patterns, correlations, or trends from the vast amount of available data. This process involves data preprocessing, cleansing, transformation, statistical analysis, machine learning, data visualization, and other techniques tailored to handle the specific challenges of large-scale data. The insights derived from massive datasets can have significant implications in various domains, including scientific discoveries, business intelligence, personalized recommendations, predictive analytics, fraud detection, and infrastructure optimization. It's worth noting that the term "massive dataset" is often used interchangeably with terms like "big data" or "large-scale data." While there is no strict definition for these terms, they generally refer to datasets that exceed the capabilities of conventional data processing methods and require specialized approaches for storage, management, and analysis.

As is known in the art, MACHINE LEARNING is a subfield of artificial intelligence (AI) that focuses on the development of algorithms and models that enable computers to learn from and make predictions or decisions based on data, without being explicitly programmed. It involves the use of statistical techniques and computational algorithms to identify patterns, extract insights, and make predictions or decisions from the available data.

Machine learning algorithms are designed to automatically learn and improve from experience or examples, allowing them to adapt to new data and make accurate predictions or decisions. These algorithms can be broadly categorized into three main types:

Supervised Learning: In supervised learning, the machine learning algorithm learns from a labeled dataset, where each data instance is associated with a known target or outcome. The algorithm learns to generalize from the labeled examples and make predictions on new, unseen data. Examples of supervised learning algorithms include linear regression, decision trees, support vector machines (SVM), and neural networks.

Unsupervised Learning: In unsupervised learning, the machine learning algorithm explores the underlying structure or patterns in the dataset without explicit labels or targets. It aims to discover hidden patterns, clusters, or associations in the data. Unsupervised learning algorithms include clustering algorithms (e.g., k-means, hierarchical clustering) and dimensionality reduction techniques (e.g., principal component analysis, t-SNE).

Reinforcement Learning: Reinforcement learning involves an agent that learns to interact with an environment and make decisions based on trial and error. The agent learns through feedback in the form of rewards or penalties, guiding it to optimize its actions and maximize its cumulative reward over time. Reinforcement learning algorithms are commonly used in robotics, gaming, and control systems.

Machine learning algorithms and models play a crucial role in processing massive datasets. As datasets grow in size, traditional data processing and analysis methods may become impractical or infeasible. Machine learning offers scalable and automated approaches to handle and extract insights from massive datasets.

Machine learning algorithms can handle large-scale datasets by leveraging distributed computing and parallel processing techniques. Technologies like Apache Spark, Hadoop, and GPU acceleration enable the efficient processing and analysis of massive datasets. Machine learning models can be trained on subsets of the data in parallel or distributed across multiple computing resources to accelerate the learning process. Furthermore, machine learning techniques are designed to identify patterns, relationships, and dependencies in the data, allowing them to capture complex interactions and make predictions or decisions based on the patterns learned from the massive dataset. By learning from the data, machine learning models can handle the high dimensionality, variability, and complexity often present in massive datasets.

Such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

For example and with respect to such factors:

Gender: Biological differences between males and females can lead to variations in health conditions, disease incidence, treatment responses, and outcomes. For example, certain diseases or conditions may predominantly affect one gender more than the other.

Race: Different racial and ethnic groups can exhibit variations in disease prevalence, genetic factors, response to treatments, and healthcare disparities. These differences can contribute to variations in medical statistics among different racial and ethnic populations.

Age: Medical statistics often vary across different age groups. Certain diseases or conditions may be more common or have different manifestations in specific age brackets, such as pediatric or geriatric populations.

Location: Geographical location can impact medical statistics due to differences in environmental factors, access to healthcare, lifestyle choices, genetic variations, and regional disease patterns. For example, certain diseases may be more prevalent in specific regions or countries.

Device Type and Device Class: In medical research and statistics, different types and classes of devices can have varying performance, efficacy, safety profiles, and outcomes. The characteristics and use of specific medical devices can influence medical statistics related to their effectiveness, complications, and patient outcomes.

Seasonality: Some medical conditions or diseases exhibit seasonal patterns. For instance, respiratory illnesses like influenza may be more prevalent during certain seasons. Seasonal variations can affect medical statistics related to disease incidence, hospitalizations, and mortality rates.

Time of Day: Physiological parameters and disease symptoms can vary throughout the day. For example, blood pressure and heart rate can fluctuate depending on circadian rhythms. Time of day can influence medical statistics related to monitoring vital signs or evaluating symptoms at different time points.

Further, this list of factors is not intended to be exhaustive, and there may be other factors specific to certain medical conditions or studies that can contribute to variations in medical statistics. Additionally, there may be a historical component to such defined signal norms (e.g., defined signal norms 228), wherein historical norms across different recent timespans have varying implications (i.e. last 15 mins vs. last 6 hours). For example, the historical norm for a patient admitted for extreme hypertension may have a very high systolic/diastolic pressure readings when the patient is first admitted . . . but may have much lower systolic/diastolic pressure readings the following day or week.

Information process 10 may investigate 304 the outliers (e.g., outliers 230) to determine if an issue exists with the device (e.g., one or more of first vendor devices 202 and/or one or more of second vendor devices 206). For example, information process 10 may investigate 304 the outliers (e.g., outliers 230) to determine if: the outliers (e.g., outliers 230) are inaccurate (e.g., due to a malfunctioning device); the outliers (e.g., outliers 230) are accurate but the patient (e.g., patient 232) is not experiencing an issue (e.g., due to the patients "norms" being outside of societal "norms"); and the outliers (e.g., outliers 230) are accurate and the patient (e.g., patient 232) is experiencing an issue.

For example and when investigating 304 the outliers (e.g., outliers 230) to determine if an issue exists with the device (e.g., one or more of first vendor devices 202 and/or one or more of second vendor devices 206), information process 10 may physically investigate 306 the outliers (e.g., outliers 230). For example, information process 10 may request that e.g., a nurse assigned to patient 232 physically investigate 306 the outliers (e.g., outliers 230) by visiting the room of patient 232 to e.g., confirm the proper operation of the device (e.g., one or more of first vendor devices 202 and/or one or more of second vendor devices 206) and/or to confirm that the patient (e.g., patient 232) is not experiencing a medical issue (e.g., a low/high heart rate and/or a low/high respiratory rate).

Additionally/alternatively and when investigating 304 the outliers (e.g., outliers 230) to determine if an issue exists with the device (e.g., one or more of first vendor devices 202 and/or one or more of second vendor devices 206), information process 10 may examine 308 other data signals from the device (e.g., one or more of first vendor devices 202 and/or one or more of second vendor devices 206). Often times, when a patient is experiencing a medical issue, multiple events may occur. For example, if the patient (e.g., patient 232) is experiencing a respiratory medical issue, a reduced heart rate may be accompanied by an elevated respiratory rate or a reduced blood gas saturation. So in the event that the outlier for patient 232 is a reduced heart rate, information process 10 may examine 308 other data signals (e.g., respiratory rate and/or blood gas saturation) from the device (e.g., one or more of first vendor devices 202 and/or one or more of second vendor devices 206) to determine if an issue exists. Therefore, if the other data signals (e.g., respiratory rate and/or blood gas saturation) from the device are normal, information process 10 may determine that an issue does not exist (e.g., patient 322 is not having a medical issue).

Information process 10 may adjust 310 outlier definition criteria to eliminate the outlier (e.g., outliers 230) if an issue does not exist. As discussed above, if the patient (e.g., patient 232) is a seasoned athlete of exceptional health, their "normal" heartrate may be 50-55 beats per minute and their "normal" respiratory rate may be 9-11 breaths per minute. Accordingly and in such a situation, the individual "norms" of the patient (e.g., patient 232) would consistently be outliers (e.g., outliers 230) if the societal heartrate norms and respiratory rate norms were applied to patient 232. Accordingly, information process 10 may adjust 310 outlier definition criteria to eliminate the outlier (e.g., outliers 230) if an issue does not exist, wherein this outlier definition criteria may include signal thresholds.

As discussed above, while the defined signal norms (e.g., defined signal norms 228) for a heart rate is 60-100 beats per minute and a respiratory rate is 12-20 breaths per minute, information process 10 may adjust 310 outlier definition criteria to eliminate the outlier (e.g., outliers 230) if an issue does not exist.

For example and when adjusting 310 the outlier definition criteria, information process 10 may define 312 bespoke outlier definition criteria for the device (e.g., one or more of first vendor devices 202 and/or one or more of second vendor devices 206). Continuing with the above-stated example, being the "normal" heartrate of patient 232 is 50-55 beats per minute and the "normal" respiratory rate is 9-11 breaths per minute, information process 10 may adjust 310 the lower range of the heart rate to 48 beats per minute and may adjust 310 the lower range of the respiratory rate to 8 breaths per minute . . . thus eliminating the outlier (e.g., outliers 230).

Conversely and if an issue does exist with patient 232, information process 10 may address 314 the issue. Accordingly and if patient 232 is in respiratory distress, information process 10 may e.g., notify a doctor, make an emergency announcement, notify medical staff, etc.

Establishing Norms for a Device:

The following discussion concerns the manner in which information process 10 may be utilized to establish norms for a specific patient over a defined period of time. For example and when onboarding a patient within a hospital, generalized norms (as discussed above) may be utilized. However and as is often the case, societal norms may not be applicable to a specific individual. So while societal norms may be initially utilized, they may prove to be inapplicable over time on an individual basis.

Figure 5:
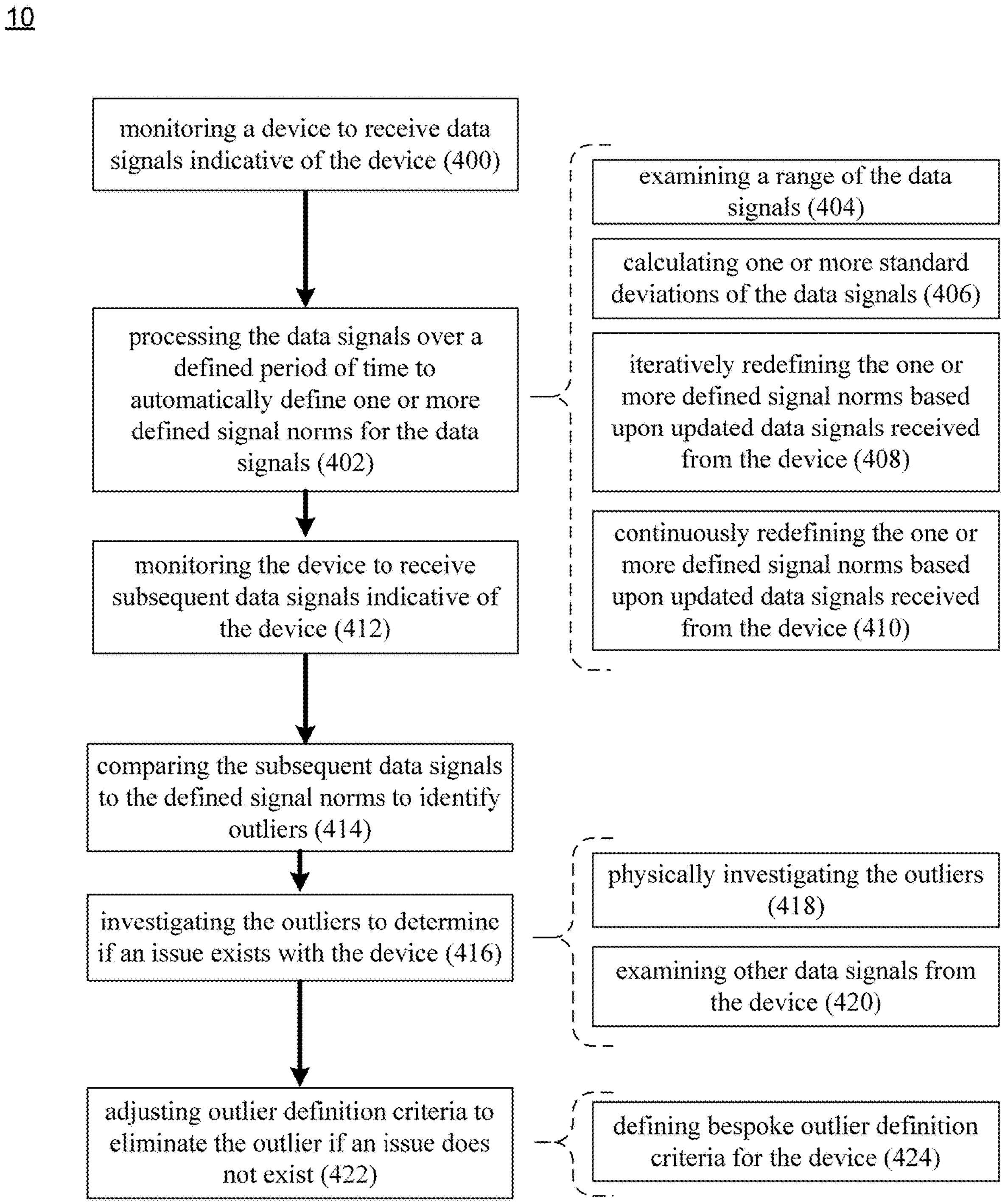
FIG. 5 is another flowchart of the information process of FIG. 1 according to an embodiment of the present disclosure.

Referring also to FIG. 5 and as discussed above, information process 10 may monitor 400 a device (e.g., one or more of first vendor devices 202 and/or one or more of second vendor devices 206) to receive data signals (e.g., one or more of data signals 200 and/or one or more of data signals 204) indicative of the device (e.g., one or more of first vendor devices 202 and/or one or more of second vendor devices 206), wherein the data signals (e.g., one or more of data signals 200 and/or one or more of data signals 204) may concern one or more details of the device (e.g., one or more of first vendor devices 202 and/or one or more of second vendor devices 206) and/or uses of the device (e.g., one or more of first vendor devices 202 and/or one or more of second vendor devices 206).

As discussed above, the device (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further and as discussed above, the device (e.g., one or more of first vendor devices 202 and/or one or more of second vendor devices 206) may include one or more sub devices (e.g., sub devices 224, 226).

Information process 10 may process 402 the data signals (e.g., one or more of data signals 200 and/or one or more of data signals 204) over a defined period of time to automatically define one or more defined signal norms for the data signals (e.g., one or more of data signals 200 and/or one or more of data signals 204). As discussed above, when onboarding a patient (e.g., patient 232) within a hospital, generalized norms (e.g., societal norms) may be utilized. However and as also discussed above, these generalized norms (e.g., societal norms) are often inapplicable with respect specific patients. Accordingly, information process 10 may process 402 these data signals (e.g., one or more of data signals 200 and/or one or more of data signals 204) over a defined period of time (e.g., several minutes, several hours, several days, etc.) so that information process 10 may automatically define one or more defined signal norms (e.g., defined signal norms 228) for the data signals (e.g., one or more of data signals 200 and/or one or more of data signals 204)

When processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may: examine 404 a range of the data signals (e.g., one or more of data signals 200 and/or one or more of data signals 204).

Continuing with the above stated example, assume that the defined signal norms (e.g., defined signal norms 228) for a heart rate is 60-100 beats per minute and a respiratory rate is 12-20 breaths per minute. Accordingly and when onboarding patient 232 into the hospital, such "societal" norms may be used. However, information process 10 may process 402 the data signals (e.g., one or more of data signals 200 and/or one or more of data signals 204) over a defined period of time (e.g., several minutes, several hours, several days, etc.) so that information process 10 may automatically define one or more defined signal norms (e.g., defined signal norms 228) for the data signals (e.g., one or more of data signals 200 and/or one or more of data signals 204).

As discussed above, if the patient (e.g., patient 232) is a seasoned athlete of exceptional health, their "normal" heart-rate may be 50-55 beats per minute and their "normal" respiratory rate may be 9-11 breaths per minute. Accordingly, the use of "societal" norms with respect to the data signals (e.g., one or more of data signals 200 and/or one or more of data signals 204) may result in an abundance of "false" alarms being issued by the device (e.g., one or more of first vendor devices 202 and/or one or more of second vendor devices 206) due to the appearance that patient 232 has a very low heart rate of 50-55 beats per minute (when the "societal" norm is 60-100) and a very low respiratory rate of 9-11 breaths per minute (when the societal norm is 12-20). Accordingly, information process 10 may examine 404 a range of the data signals (e.g., one or more of data signals 200 and/or one or more of data signals 204) and identify that patient 232 has the following data signal ranges: heart rate of 50-55 beats per minute (even though the "societal" norm is 60-100); and a respiratory rate of 9-11 breaths per minute (even though the societal norm is 12-20).

Further and when processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may calculate 406 one or more standard deviations of the data signals (e.g., one or more of data signals 200 and/or one or more of data signals 204).

Standard deviation is a statistical measure that quantifies the amount of variation or dispersion in a dataset. It provides a numerical value that indicates how spread out the data points are from the mean (average) of the dataset. When considering a data range, the standard deviation can provide insights into the variability within that range. It helps assess the extent to which data points deviate from the mean value within the given range.

To calculate the standard deviation within a data range, you would typically follow these steps:

Calculate the mean (average) of the data within the range.

Subtract the mean from each data point within the range.

Square each of the differences obtained in step 2.

Calculate the average (mean) of the squared differences.

Take the square root of the average obtained in step 4.

The resulting value is the standard deviation within the specified data range. It represents the average amount by which data points deviate from the mean within that particular range. A larger standard deviation indicates greater variability or dispersion, meaning the data points within the range are more spread out from the mean. Conversely, a smaller standard deviation suggests less variation and a tighter clustering of data points around the mean within the range.

Additionally and when processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may: iteratively redefine 408 the one or more defined signal norms (e.g., defined signal norms 228) based upon updated data signals (e.g., one or more of data signals 200 and/or one or more of data signals 204) received from the device (e.g., one or more of first vendor devices 202 and/or one or more of second vendor devices 206). For example, information process 10 may iteratively redefine 408 (e.g., every 10 seconds, or every one minute, or every few minutes, etc.) the defined signal norms (e.g., defined signal norms 228) based upon updated data signals (e.g., one or more of data signals 200 and/or one or more of data signals 204) received from the device (e.g., one or more of first vendor devices 202 and/or one or more of second vendor devices 206). In the configuration, the compute requirements of information process 10 may be reduced at the expense of reduced performance.

Further and when processing 402 the data signals (e.g., one or more of data signals 200 and/or one or more of data signals 204) over a defined period of time (e.g., several minutes, several hours, several days, etc.) to automatically define one or more defined signal norms (e.g., defined signal norms 228) for the data signals (e.g., one or more of data signals 200 and/or one or more of data signals 204), information process 10 may: continuously redefine 410 the one or more defined signal norms based upon updated data signals (e.g., one or more of data signals 200 and/or one or more of data signals 204) received from the device (e.g., one or more of first vendor devices 202 and/or one or more of second vendor devices 206). For example, information process 10 may continuously redefine 410 (e.g., every few milliseconds, every time new data is received, etc.) the defined signal norms (e.g., defined signal norms 228) based upon updated data signals (e.g., one or more of data signals 200 and/or one or more of data signals 204) received from the device (e.g., one or more of first vendor devices 202 and/or one or more of second vendor devices 206). In the configuration, the performance of information process 10 may be increased at the expense of increased compute requirements.

Information process 10 may monitor 412 the device (e.g., one or more of first vendor devices 202 and/or one or more of second vendor devices 206) to receive subsequent data signals (e.g., data signals 234) indicative of the device (e.g., one or more of first vendor devices 202 and/or one or more of second vendor devices 206), wherein information process 10 may compare 414 the subsequent data signals (e.g., data signals 234) to the defined signal norms (e.g., defined signal norms 228) to identify outliers (e.g., outliers 230).

As discussed above, information process 10 may investigate 416 the outliers (e.g., outliers 230) to determine if an issue exists with the device (e.g., one or more of first vendor devices 202 and/or one or more of second vendor devices 206), wherein investigating 416 the outliers (e.g., outliers 230) to determine if an issue exists with the device (e.g., one or more of first vendor devices 202 and/or one or more of second vendor devices 206) may include physically investigating 418 the outliers (e.g., outliers 230); and/or examining 420 other data signals from the device (e.g., one or more of first vendor devices 202 and/or one or more of second vendor devices 206).

As discussed above, information process 10 may adjust 422 outlier definition criteria to eliminate the outlier (e.g., outliers 230) if an issue does not exist. For example and when adjusting 422 the outlier definition criteria, information process 10 may define 424 bespoke outlier definition criteria for the device (e.g., one or more of first vendor devices 202 and/or one or more of second vendor devices 206). Conversely and if an issue does exist with patient 232, information process 10 may address by e.g., notifying a doctor, making an emergency announcement, notifying medical staff, etc.

Centralized Threshold Adjustment:

The following discussion concerns the manner in which information process 10 may enable the centralized management of the thresholds, wherein these thresholds may be used by devices (e.g., one or more of first vendor devices 202 and/or one or more of second vendor devices 206) to establish norms for the patient being monitored. As discussed above, oftentimes generalized norms are not applicable to specific patients. And being these norms/thresholds are used to generate alarms, inapplicable norms/thresholds many result in an abundance of "false" alarms being issued by the device (e.g., one or more of first vendor devices 202 and/or one or more of second vendor devices 206). Accordingly, information process 10 may enable the centralized management of such thresholds.

Figure 6:
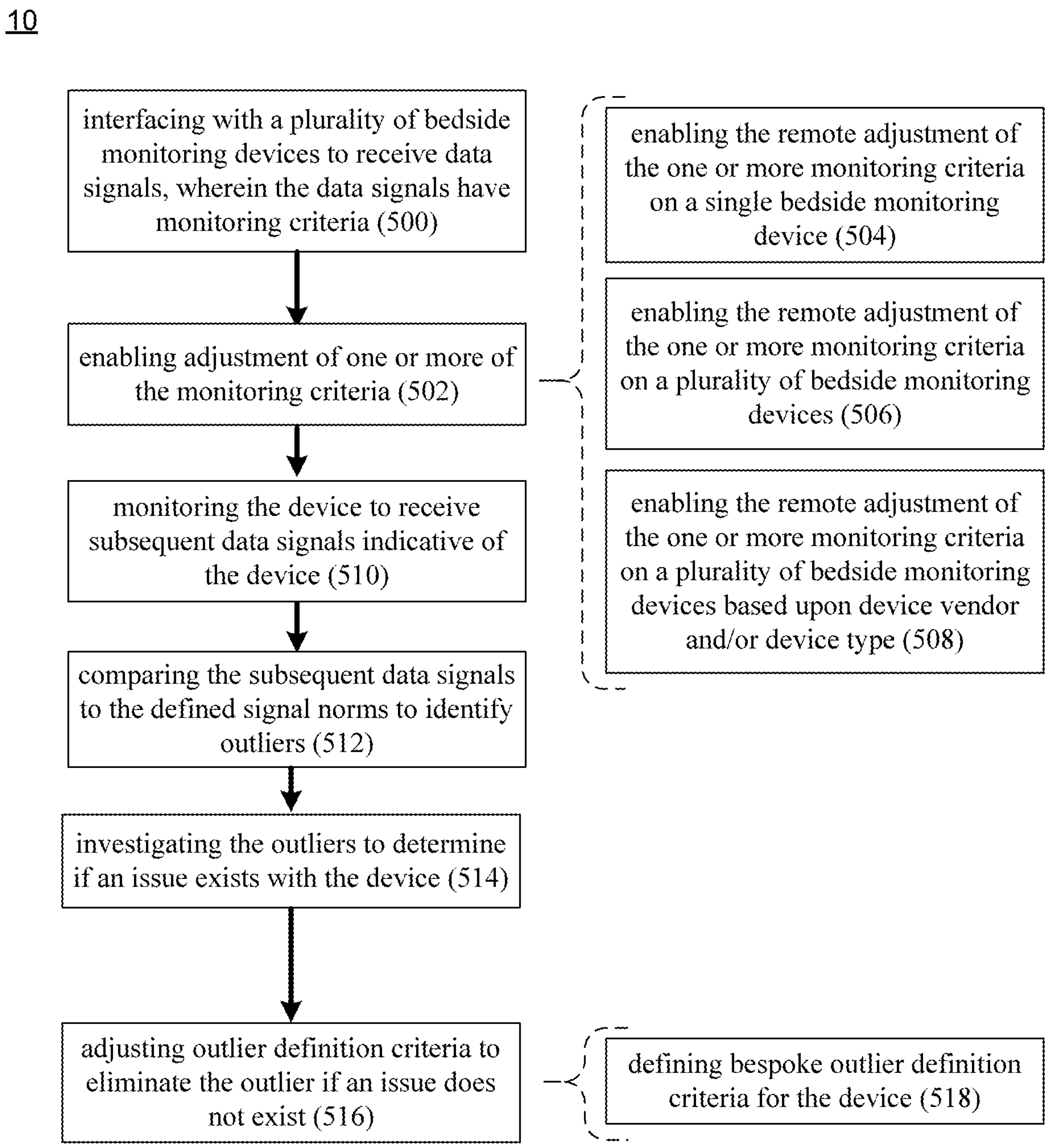
FIG. 6 is another flowchart of the information process of FIG. 1 according to an embodiment of the present disclosure.

Referring also to FIG. 6, information process 10 may interface 500 with a plurality of bedside monitoring devices (e.g., one or more of first vendor devices 202 and/or one or more of second vendor devices 206) to receive data signals (e.g., one or more of data signals 200 and/or one or more of data signals 204). These data signals (e.g., one or more of data signals 200 and/or one or more of data signals 204) may have monitoring criteria, wherein the monitoring criteria may include one or more thresholds.

As discussed above, examples of such monitoring criteria/thresholds may include defined signal norms (e.g., defined signal norms 228). These defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning. Accordingly, such monitoring criteria (e.g., defined signal norms 228), may include user-defined monitoring criteria and/or machine-defined monitoring criteria.

As also discussed above, such monitoring criteria (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

As also discussed above, such data signals (e.g., one or more of data signals 200 and/or one or more of data signals 204) may concern one or more details of the plurality of bedside monitoring devices (e.g., one or more of first vendor devices 202 and/or one or more of second vendor devices 206) and/or uses of the plurality of bedside monitoring devices (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

As also discussed above, the plurality of bedside monitoring devices (e.g., one or more of first vendor devices 202 and/or one or more of second vendor devices 206) may span a plurality of vendors, wherein (as discussed above) information process 10 may enable such multiple-vendor devices to communicate.

Information process 10 may enable 502 adjustment of one or more of the monitoring criteria (e.g., defined signal norms 228). For example, information process 10 may enable 502 adjustment of one or more of the monitoring criteria (e.g., defined signal norms 228) by a user (e.g., user 236) via a computing device (e.g., computing device 238). Examples of user 236 may include but are not limited to a medical professional, such as a nurse, nurse supervisor, medical technician, physician's assistant, physician, etc. Examples of the computing device (e.g., computing device 238) may include but are not limited to a nurse's workstation, a tablet computer, a laptop computer, a desktop computer, a smart phone, etc.

As discussed above, the defined signal norms (e.g., defined signal norms 228) for a heart rate may be 60-100 beats per minute and for a respiratory rate may be 12-20 breaths per minute. Accordingly, information process 10 may enable 502 adjustment of one or more of the monitoring criteria (e.g., namely defined signal norms of 60-100 beats per minute for a heart rate and 12-20 breaths per minute for a respiratory rate) by the user (e.g., user 236) via a computing device (e.g., computing device 238). Additionally/alternatively, information process 10 may enable 502 adjustment of one or more of the monitoring criteria (e.g., namely defined signal norms of 60-100 beats per minute for a heart rate and 12-20 breaths per minute for a respiratory rate) by the user (e.g., user 236) by providing the user (e.g., user 236) with instructions (e.g., graphical and/or text-based) concerning how to manually adjust the one or more of the monitoring criteria (e.g., namely defined signal norms of 60-100 beats per minute for a heart rate and 12-20 breaths per minute for a respiratory rate) via e.g., a user interface (not shown) included within the plurality of bedside monitoring devices (e.g., one or more of first vendor devices 202 and/or one or more of second vendor devices 206).

When enabling 502 the adjustment of one or more of these monitoring criteria (e.g., defined signal norms 228), information process 10 may: enable 504 the remote adjustment of the one or more monitoring criteria (e.g., defined signal norms 228) on a single bedside monitoring device (e.g., one or more of first vendor devices 202 and/or one or more of second vendor devices 206).

As discussed above, "societal" defined signal norms (e.g., defined signal norms 228) may not work for everyone. So while the defined signal norms (e.g., defined signal norms 228) for a heart rate may be 60-100 beats per minute and a respiratory rate may be 12-20 breaths per minute; if a patient (e.g., patient 232) is a seasoned athlete of exceptional health, their "normal" heartrate may be 50-55 beats per minute and their "normal" respiratory rate may be 9-11 breaths per minute. Accordingly, information process 10 may: enable 504 the remote adjustment of the one or more monitoring criteria (e.g., defined signal norms 228) on a single bedside monitoring device (e.g., the single bedside device associated with patient 232) so that the monitoring criteria for the heart rate of patient 232 may be adjusted downward from 60-100 beats per minute to 50-55 beats per minute and the monitoring criteria for the respiratory rate may be adjusted downward from 12-20 breaths per minute to 9-11 breaths per minute, wherein such adjustment may be made by the user (e.g., user 236) via the computing device (e.g., computing device 238).

When enabling 502 the adjustment of one or more of these monitoring criteria (e.g., defined signal norms 228), information process 10 may: enable 506 the remote adjustment of the one or more monitoring criteria (e.g., defined signal norms 228) on a plurality of bedside monitoring devices (e.g., one or more of first vendor devices 202 and/or one or more of second vendor devices 206).

For example, assume that the "societal" defined signal norms (e.g., defined signal norms 228) are not working for the majority of people within e.g., a hospital, a unit, a ward, a clinic, etc. For example, assume that a large portion of the people within the hospital, the unit, the ward, the clinic, etc. have a heart rate that is slightly over 100 (e.g., 101-105 beats per minute), resulting in the generation of a considerable number of false alarms. Accordingly, information process 10 may enable 506 the remote adjustment of the one or more monitoring criteria (e.g., defined signal norms 228) on a plurality of bedside monitoring devices (e.g., some or all of the devices within the hospital, the unit, the ward, the clinic, etc.) so that the monitoring criteria for the heart rate of patients within the hospital, the unit, the ward, the clinic, etc. may be adjusted upward from 60-100 beats per minute to 60-110 beats per minute, wherein such adjustment may be made by the user (e.g., user 236) via the computing device (e.g., computing device 238).

When enabling 502 the adjustment of one or more of these monitoring criteria (e.g., defined signal norms 228), information process 10 may: enable 508 the remote adjustment of the one or more monitoring criteria (e.g., defined signal norms 228) on a plurality of bedside monitoring devices (e.g., one or more of first vendor devices 202 and/or one or more of second vendor devices 206) based upon device vendor and/or device type.

For example, assume that the default defined signal norms (e.g., defined signal norms 228) concerning heart rate are 60-100 beats per minute (for devices made by Company A), while the default defined signal norms (e.g., defined signal norms 228) concerning heart rate are 70-90 beats per minute (for devices made by Company B). Assume that the default defined signal norms (e.g., defined signal norms 228) for Company A (i.e., a heart rate are 60-100 beats per minute) appear to be working properly, as it is not triggering a high level of false alarms. However, the default defined signal norms (e.g., defined signal norms 228) for Company B (i.e., a heart rate are 70-90 beats per minute) appear to not be working properly, as it is triggering a high level of false alarms. Accordingly, information process 10 may enable 508 the remote adjustment of the one or more monitoring criteria (e.g., defined signal norms 228) on a plurality of bedside monitoring devices (e.g., the bedside devices manufactured by Company B) so that the heart rate monitoring criteria for the bedside devices manufactured by Company B may be adjusted from 70-90 beats per minute to 60-100 beats per minute, wherein such adjustment may be made by the user (e.g., user 236) via the computing device (e.g., computing device 238).

Information process 10 may monitor 510 the device (e.g., one or more of first vendor devices 202 and/or one or more of second vendor devices 206) to receive subsequent data signals (e.g., data signals 234) indicative of the device (e.g., one or more of first vendor devices 202 and/or one or more of second vendor devices 206), wherein information process 10 may compare 512 the subsequent data signals (e.g., data signals 234) to the defined signal norms (e.g., defined signal norms 228) to identify outliers (e.g., outliers 230).

As discussed above, information process 10 may investigate 514 the outliers (e.g., outliers 230) to determine if an issue exists with the device (e.g., one or more of first vendor devices 202 and/or one or more of second vendor devices 206), wherein investigating 514 the outliers (e.g., outliers 230) to determine if an issue exists with the device (e.g., one or more of first vendor devices 202 and/or one or more of second vendor devices 206) may include physically investigating the outliers (e.g., outliers 230); and/or examining other data signals from the device (e.g., one or more of first vendor devices 202 and/or one or more of second vendor devices 206).

As discussed above, information process 10 may adjust 516 outlier definition criteria to eliminate the outlier (e.g., outliers 230) if an issue does not exist. For example and when adjusting 516 the outlier definition criteria, information process 10 may define 518 bespoke outlier definition criteria for the device (e.g., one or more of first vendor devices 202 and/or one or more of second vendor devices 206). Conversely and if an issue does exist with patient 232, information process 10 may address by e.g., notifying a doctor, making an emergency announcement, notifying medical staff, etc.

Automated Device Personalization:

The following discussion concerns the manner in which information process 10 may enable the customization of a bedside monitoring device (e.g., one or more of first vendor devices 202 and/or one or more of second vendor devices 206) based upon patient information obtained from a medical record (e.g., an EMR and/or an EHR). As discussed above, oftentimes generalized norms are not applicable to specific patients. And being these norms are used to generate alarms, inapplicable norms many result in an abundance of "false" alarms being issued by the device (e.g., one or more of first vendor devices 202 and/or one or more of second vendor devices 206). Accordingly, information process 10 may enable the setting of such norms based upon patient information to mitigate such false alarms.

Figure 7:
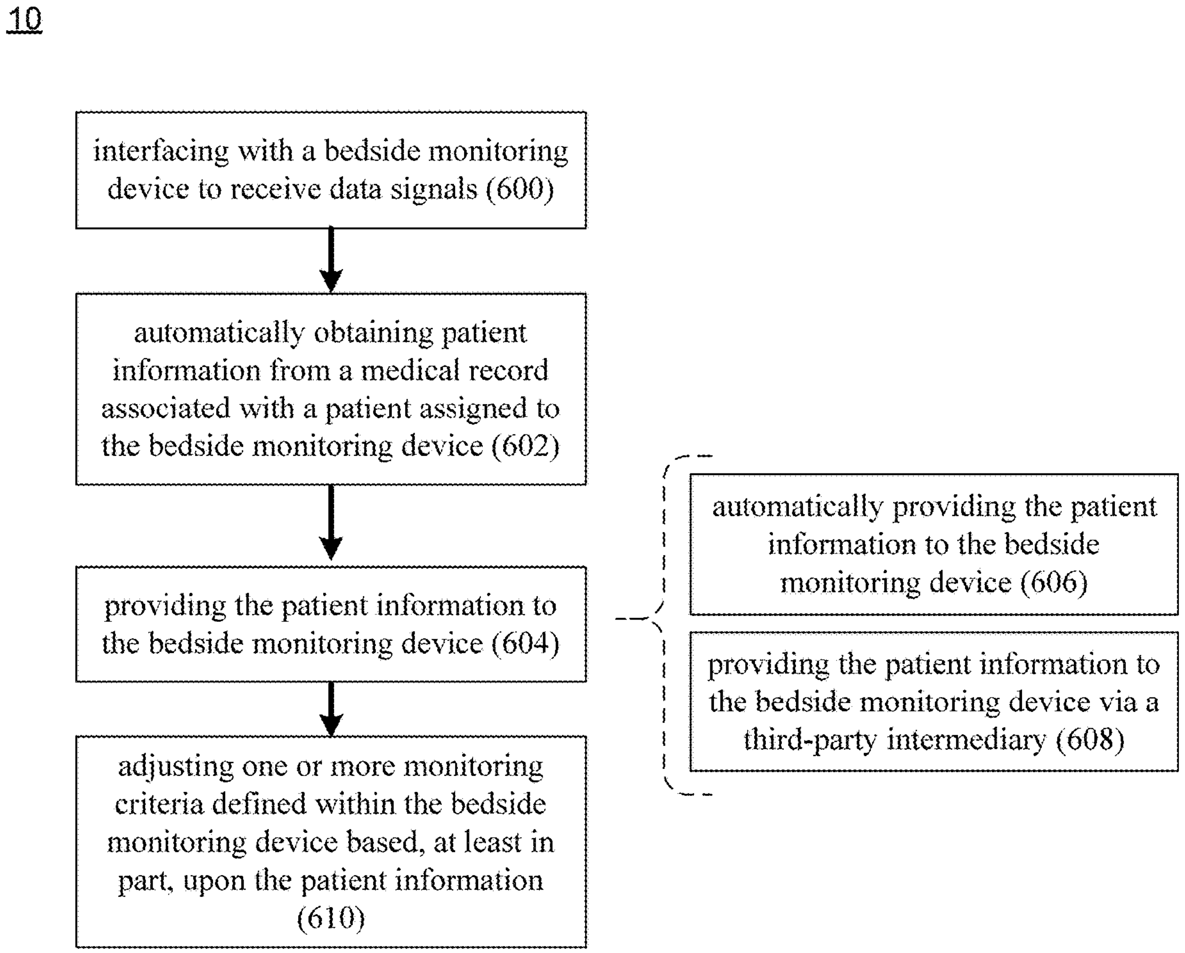
FIG. 7 is another flowchart of the information process of FIG. 1 according to an embodiment of the present disclosure.

Referring also to FIG. 7, information process 10 may interface 600 with a bedside monitoring device (e.g., one or more of first vendor devices 202 and/or one or more of second vendor devices 206) to receive data signals (e.g., one or more of data signals 200 and/or one or more of data signals 204).

As also discussed above, such data signals (e.g., one or more of data signals 200 and/or one or more of data signals 204) may concern one or more details of the bedside monitoring device (e.g., one or more of first vendor devices 202 and/or one or more of second vendor devices 206) and/or uses of the bedside monitoring devices (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

Further and as discussed above, the bedside monitoring device (e.g., one or more of first vendor devices 202 and/or one or more of second vendor devices 206) may include one or more bedside monitoring sub devices (e.g., sub devices 224, 226).

Information process 10 may automatically obtain 602 patient information (e.g., patient information 240) from a medical record (e.g., patient record 242) associated with a patient (e.g., patient 232) assigned to the bedside monitoring device (e.g., one or more of first vendor devices 202 and/or one or more of second vendor devices 206).

The patient information (e.g., patient information 240) may include but is not limited to one or more of: a patient name, a patient demographic (e.g., age, gender, income level, race, employment, location, homeownership, and level of education), a medical history of the patient, a medication history of the patient, caregiver assignment history (e.g., what medical professionals are assigned to the patient) and patient assignment history (e.g., what room is assigned to the patient).

Examples of the medical record (e.g., patient record 242) may include but are not limited to one or more of an EMR and an EHR.

EHR stands for Electronic Health Record. An EHR is a digital version of a patient's paper medical records, containing comprehensive and organized information about an individual's health and medical history. It is designed to be accessible, updated, and shared securely among authorized healthcare providers and organizations.

Key features of an EHR include:

Digital Health Information: EHRs contain a wide range of health-related information, including patient demographics, medical history, diagnoses, medications, allergies, laboratory results, imaging reports, immunization records, and more. These records are stored electronically, making them easily accessible and searchable.

Comprehensive View: EHRs provide a holistic and longitudinal view of a patient's health. They capture information from various healthcare providers and settings, enabling authorized users to access and review a patient's complete medical history, facilitating better care coordination and continuity.

Data Entry and Updates: EHRs allow healthcare providers to enter and update patient information electronically. This includes clinical notes, examination findings, treatment plans, progress notes, and other relevant data. EHR systems often include templates and forms to assist in efficient data entry.

Interoperability: EHRs support the exchange and sharing of health information across different healthcare settings and systems. Interoperability enables seamless communication and collaboration among healthcare providers, facilitating coordinated care, referrals, and transitions between different care settings.

Decision Support: EHRs often include decision support tools, such as clinical guidelines, alerts, reminders, and drug interaction checks. These features assist healthcare providers in making informed decisions, improving patient safety, and adhering to evidence-based practices.

Privacy and Security: EHRs prioritize the security and privacy of patient information. They employ stringent safeguards to protect against unauthorized access, data breaches, and ensure compliance with relevant privacy regulations, such as the Health Insurance Portability and Accountability Act (HIPAA) in the United States.

The adoption of EHRs aims to enhance patient care, improve efficiency, reduce medical errors, support evidence-based practices, and facilitate health information exchange. It allows healthcare providers to access accurate and up-to-date patient information at the point of care, leading to better-informed decisions and improved patient outcomes.

EMR stands for Electronic Medical Record. An EMR is a digital version of a patient's medical records that is maintained within a healthcare provider's own system or network. It is similar to an Electronic Health Record (EHR), but with a narrower scope as it primarily focuses on the medical information specific to a single healthcare organization or practice.

Here are some key aspects of an EMR:

Digital Storage: EMRs store patient health information electronically within a specific healthcare organization's database or network. They replace traditional paper-based medical charts and records, making information more accessible and easily retrievable.

Medical Information: EMRs primarily contain medical and clinical information, including diagnoses, treatments, medications, medical procedures, laboratory and imaging results, progress notes, and other relevant data specific to the healthcare provider's practice.

Organization-Specific: Unlike EHRs, which are designed to be interoperable and shared across different healthcare settings, EMRs are typically limited to a specific healthcare organization or practice. They are customized to fit the workflows and requirements of the particular healthcare provider using them.

Data Entry and Updates: Healthcare providers enter patient information directly into the EMR system using electronic forms, templates, or structured data entry. EMRs support efficient data entry and updates, including capturing patient demographics, medical history, examination findings, and treatment plans.

Clinical Decision Support: EMRs often include clinical decision support features, such as drug interaction checks, alerts for potential contraindications or allergies, reminders for preventive care, and clinical guidelines. These tools assist healthcare providers in making informed decisions and improving patient care.

Privacy and Security: EMRs prioritize the privacy and security of patient information, implementing measures to protect against unauthorized access, data breaches, and compliance with relevant privacy regulations, such as HIPAA in the United States.

EMRs are primarily used within a single healthcare organization or practice to manage patient records, streamline clinical workflows, and support patient care. While they may not have the same level of interoperability as EHRs, efforts are being made to enhance data exchange and integration between different systems to promote better care coordination and continuity across healthcare settings.

Accordingly, assume that patient 232 (i.e., John Smith) is admitted to the hospital and is in Bed A in Room 203. Accordingly and once admitted, information process 10 may automatically obtain 602 patient information 240 from patient record 242 associated with patient 232 (i.e., John Smith) assigned to the bedside monitoring device (e.g., one or more of first vendor devices 202 and/or one or more of second vendor devices 206). As discussed above, this patient information (e.g., patient information 240) may include but is not limited to one or more of: a patient name, a patient demographic (e.g., age, gender, income level, race, employment, location, homeownership, and level of education), a medical history of the patient, a medication history of the patient, caregiver assignment history (e.g., what medical professionals are assigned to the patient) and patient assignment history (e.g., what room is assigned to the patient).

Once obtained 602, information process 10 may provide 604 the patient information (e.g., patient information 240) to the bedside monitoring device (e.g., one or more of first vendor devices 202 and/or one or more of second vendor devices 206). For example, information process 10 may provide 604 patient information 240 to the bedside monitoring device (e.g., one or more of first vendor devices 202 and/or one or more of second vendor devices 206) that identifies the name of patient 232, the nurse assigned to patient 232, the doctor assigned to patient 232, the admission date of patient 232, the anticipated discharge date of patient 232, the average blood pressure of patient 232, the average respiratory rate of patient 232, the average blood gas level of patient 232, etc.

When providing 604 the patient information (e.g., patient information 240) to the bedside monitoring device (e.g., one or more of first vendor devices 202 and/or one or more of second vendor devices 206), information process 10 may: automatically provide 606 the patient information (e.g., patient information 240) to the bedside monitoring device (e.g., one or more of first vendor devices 202 and/or one or more of second vendor devices 206). For example, information process 10 may automatically provide 606 the patient information (e.g., patient information 240) directly to the bedside monitoring device (e.g., one or more of first vendor devices 202 and/or one or more of second vendor devices 206) in an automated fashion without the need for third party assistance/intervention.

When providing 604 the patient information to the bedside monitoring device (e.g., one or more of first vendor devices 202 and/or one or more of second vendor devices 206), information process 10 may: provide 608 the patient information (e.g., patient information 240) to the bedside monitoring device (e.g., one or more of first vendor devices 202 and/or one or more of second vendor devices 206) via a third-party intermediary (e.g., third-party intermediary 244). For example, information process 10 may: provide 608 the patient information (e.g., patient information 240) indirectly to the bedside monitoring device (e.g., one or more of first vendor devices 202 and/or one or more of second vendor devices 206), wherein the patient information 240 is first provided to third-party intermediary 244 (e.g., a hospital administrator or medical device professional) and third-party intermediary 244 subsequently provides the patient information 240 to the bedside monitoring device (e.g., one or more of first vendor devices 202 and/or one or more of second vendor devices 206).

Information process 10 may adjust 610 one or more monitoring criteria defined within the bedside monitoring device (e.g., one or more of first vendor devices 202 and/or one or more of second vendor devices 206) based, at least in part, upon the patient information (e.g., patient information 240).

As discussed above, examples of such monitoring criteria may include defined signal norms (e.g., defined signal norms 228) and/or one or more signal thresholds. Assume that the default defined signal norms (e.g., defined signal norms 228) concerning heart rate is 60-100 beats per minute. Further assume that the patient (e.g., patient 232) is a seasoned athlete of exceptional health and their "normal" heartrate is defined within patient information 240 as 50-55 beats per minute. Accordingly, information process 10 may adjust 610 the monitoring criteria for heart rate (as defined within the bedside monitoring device) downward from 60-100 beats per minute to e.g., 45-60 beats per minute based, at least in part, upon patient information 240.

Environment Baseline Setting:

The following discussion concerns the manner in which information process 10 may help to battle alarm fatigue . . . the detrimental effect of false alarms within medical facilities. False alarms are a significant concern within hospitals, as they can lead to alarm fatigue, decreased patient safety, and increased healthcare provider burden. The prevalence of false alarms can vary depending upon multiple factors, including the specific hospital, the type of medical devices used, and the clinical setting.

Studies have shown that the rate of false alarms in hospitals can be alarmingly high. For example, research conducted in intensive care units (ICUs) has reported false alarm rates ranging from 72% to 99%, indicating that the majority of alarms in these settings are false positives.

Several factors contribute to the occurrence of false alarms in hospitals:

Inadequate Alarm Parameters: Alarm systems may be set with default or suboptimal alarm thresholds, leading to alarms that trigger unnecessarily. This can be due to alarm settings being too sensitive or not properly adjusted to patient-specific conditions.

Device Malfunctions or Technical Issues: Faulty equipment or technical issues with medical devices can result in false alarms. For example, electrode or sensor detachment, poor signal quality, or software glitches can generate false positive alarms.

Lack of Contextual Information: Alarms may lack the necessary contextual information to help healthcare providers accurately interpret their significance. For instance, alarms may not consider the patient's clinical condition, medications, or concurrent therapies, leading to false alarms that do not require immediate action.

Inefficient Alarm Management: Healthcare providers may be overwhelmed by the sheer number of alarms, making it challenging to respond promptly and appropriately. This can lead to alarm fatigue, where healthcare providers become desensitized or ignore alarms due to their frequency, potentially compromising patient safety.

Addressing false alarms is a priority for healthcare organizations and device manufacturers. Efforts are being made to improve alarm management systems, enhance alarm customization options, implement better alarm algorithms, and provide more contextual information to reduce false positives and improve the accuracy and relevance of alarms. Additionally, initiatives focusing on standardization, education, and guidelines are being developed to promote best practices in alarm management and mitigate the impact of false alarms on patient care. Accordingly and as will be discussed below, information process 10 may be configured to monitor a medical environment to determine the prevalence and severity of the alarm situation within the monitored medical environment.

Figure 8:
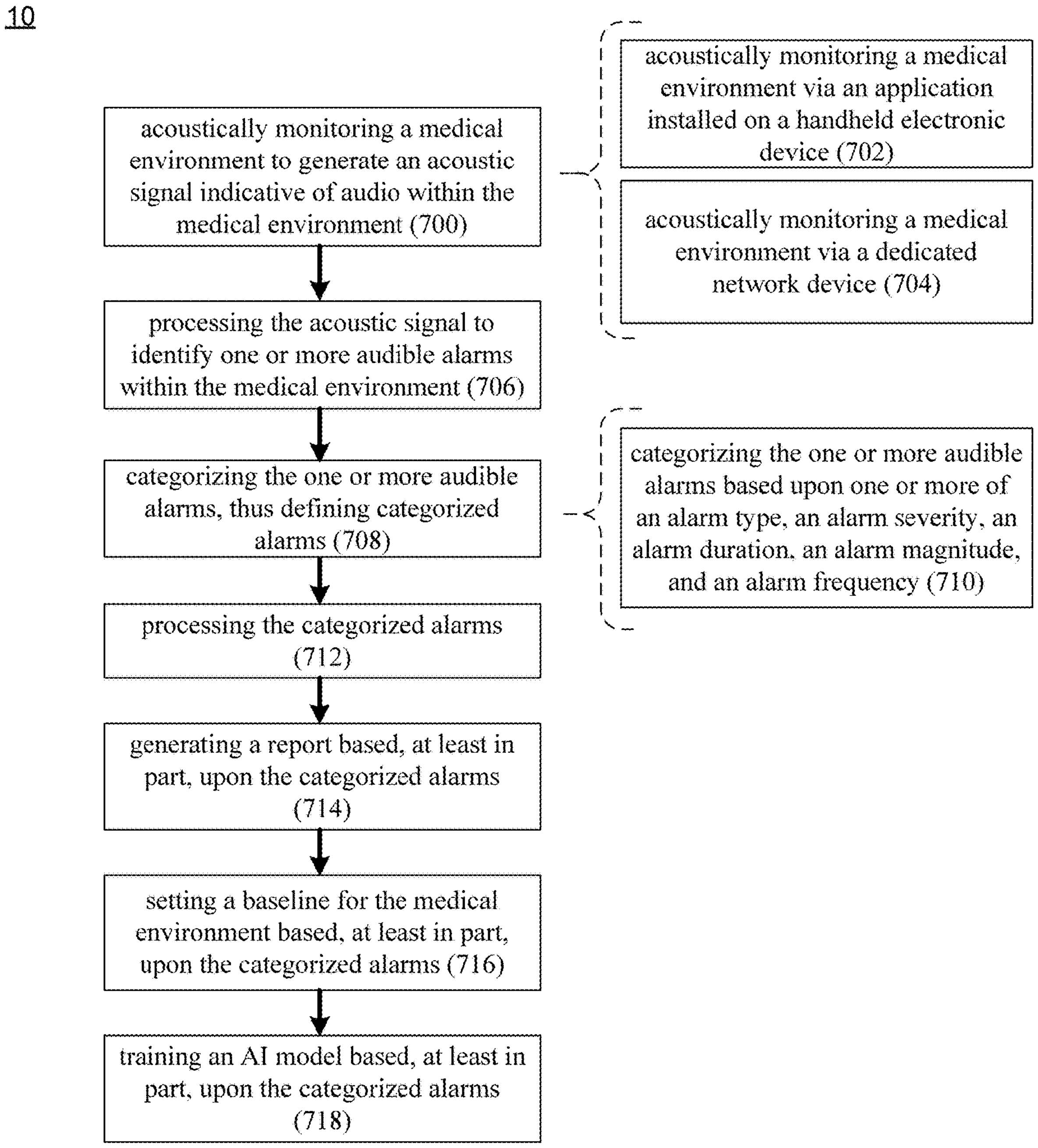
FIG. 8 is another flowchart of the information process of FIG. 1 according to an embodiment of the present disclosure.

Referring also to FIG. 8, information process 10 may acoustically monitor 700 a medical environment (e.g., hospital 246 . . . or a portion thereof) to generate an acoustic signal (e.g., acoustic signal 248) indicative of audio within the medical environment (e.g., hospital 246 . . . or a portion thereof).

When acoustically monitoring 700 a medical environment (e.g., hospital 246 . . . or a portion thereof) to generate an acoustic signal (e.g., acoustic signal 248) indicative of audio within the medical environment (e.g., hospital 246 . . . or a portion thereof), information process 10 may acoustically monitor 702 a medical environment (e.g., hospital 246 . . . or a portion thereof) via an application (e.g., application 250) installed on a handheld electronic device (e.g., handheld electronic device 252), examples of which may include but are not limited to a smart phone, a tablet computer, a wireless dedicated device, etc.).

Additionally/alternatively and when acoustically monitoring 700 a medical environment (e.g., hospital 246 . . . or a portion thereof) to generate an acoustic signal (e.g., acoustic signal 248) indicative of audio within the medical environment (e.g., hospital 246 . . . or a portion thereof), information process 10 may acoustically monitor 704 a medical environment (e.g., hospital 246 . . . or a portion thereof) via a dedicated network device (e.g., dedicated network device 252), an example of which may include but is not limited to a wall-mounted microphone.

Generally speaking, information process 10 acoustically monitors 700 the medical environment (e.g., hospital 246 . . . or a portion thereof) to generate acoustic signal 248 indicative of audio within the medical environment (e.g., hospital 246 . . . or a portion thereof) so that the quantity and quality of the alarms within the medical environment (e.g., hospital 246 . . . or a portion thereof) may be detected and determined. Accordingly, information process 10 may process 706 the acoustic signal (e.g., acoustic signal 248) to identify one or more audible alarms (e.g., audible alarms 256, 258, 260, 262) within the medical environment (e.g., hospital 246 . . . or a portion thereof).

Information process 10 may categorize 708 the one or more audible alarms (e.g., audible alarms 256, 258, 260, 262), thus defining categorized alarms (e.g., categorized alarms 264). For example and when categorizing 708 the one or more audible alarms (e.g., audible alarms 256, 258, 260, 262), information process 10 may: categorize 710 the one or more audible alarms (e.g., audible alarms 256, 258, 260, 262) based upon one or more of an alarm type, an alarm severity, an alarm duration, an alarm magnitude, and an alarm frequency.

Specifically, the alarms generated by the bedside monitoring devices (e.g., one or more of first vendor devices 202 and/or one or more of second vendor devices 206) may vary in volume, frequency, pattern and duration based upon one or more of an alarm type, an alarm severity, an alarm duration, an alarm magnitude, and an alarm frequency. Accordingly, information process 10 may be configured to categorize 710 audible alarms 256, 258, 260, 262 based upon an alarm type, an alarm severity, an alarm duration, an alarm magnitude, and an alarm frequency Information process 10 may process 712 the categorized alarms (e.g., categorized alarms 264) and generate 714 a report (e.g., report 266) based, at least in part, upon the categorized alarms (e.g., categorized alarms 264). For example, report 266 may identify the quantity and quality of audible alarms 256, 258, 260, 262 and present them within report 266 in accordance with one or more of alarm type, an alarm severity, an alarm duration, an alarm magnitude, and an alarm frequency.

Further, information process 10 may set 716 a baseline for the medical environment (e.g., hospital 246 . . . or a portion thereof) based, at least in part, upon the categorized alarms (e.g., categorized alarms 264). For example, the information defined within report 266 for the medical environment (e.g., hospital 246 . . . or a portion thereof) may be compared to other medical environments to determine how the medical environment (e.g., hospital 246 . . . or a portion thereof) compares with these other medical environments so that such a baseline may be established. For example, report 266 may identify the medical environment (e.g., hospital 246 . . . or a portion thereof) as e.g., being:

- XX % worse (or better) than the average medical environment with respect to false alarms;
- YY % worse (or better) than the average medical environment with respect to critical alarms; and
- ZZ % worse (or better) than the average medical environment with respect to total alarms.

Accordingly and through the use of such a report (e.g., report 266), the medical environment (e.g., hospital 246 . . . or a portion thereof) may be able to see what areas they are good in, as well as the areas in which they can improve (thus establishing a baseline). And by addressing the areas that need improvement, staff retention may be improved by e.g., reducing alarm fatigue.

Information process 10 may train 718 an AI model (e.g., AI model 268) based, at least in part, upon the categorized alarms (e.g., categorized alarms 264). For example, data set 270 may be generated and AI model 268 may be trained based upon data set 270. Data set 270 may include e.g., categorized alarms from the medical environment (e.g., hospital 246 . . . or a portion thereof) and from other medical environments (not shown), wherein AI model 268 may be trained by processing data set 270 to extract patterns hidden within data set 270.

Machine learning models extract patterns from a dataset through a process called training. During training, the model learns to recognize patterns and relationships within the data by adjusting its internal parameters or weights. The general steps involved in pattern extraction by a machine learning model are as follows:

Data Preparation: The dataset is preprocessed and prepared to ensure its quality and suitability for training. This may involve tasks such as data cleaning, normalization, feature selection, and splitting the dataset into training and testing subsets.

Model Selection: The appropriate machine learning model is selected based on the nature of the problem and the characteristics of the dataset. Different types of models, such as decision trees, neural networks, support vector machines, or random forests, can be used depending on the problem and the data.

Model Training: The selected model is trained using the training dataset. During this phase, the model iteratively adjusts its internal parameters based on the input data and the desired output. It tries to find the optimal settings that minimize the difference between the predicted output and the actual output in the training data.

Pattern Extraction: As the model iteratively adjusts its parameters, it learns to recognize patterns and relationships present in the data. The model identifies features or combinations of features that are most relevant for predicting the target variable or making accurate classifications. These patterns can be simple or complex and can involve various features or variables within the dataset.

Evaluation and Validation: Once the model is trained, it is evaluated using the testing dataset to assess its performance and generalization ability. The model's ability to extract patterns effectively is measured by evaluating its accuracy, precision, recall, F1 score, or other appropriate metrics based on the specific problem domain.

Application and Prediction: After training and validation, the trained model can be used to make predictions or classify new, unseen data based on the patterns it learned from the training dataset. The model applies the extracted patterns to new input data to generate predictions or classify instances based on the trained relationships.

It's important to note that the success of pattern extraction depends on several factors, such as the quality and representativeness of the training data, the choice of appropriate features, the selection of an appropriate model, and the careful tuning of model parameters. The process of extracting patterns from data is at the core of machine learning, enabling models to learn from examples and make predictions or classifications on new data.

Accordingly, by training 718 AI model 268 based, at least in part, upon categorized alarms 264, various patterns may be extracted concerning e.g., average alarms counts/types and how they relate to patient demographics, hospital locations, staffing levels, staff attrition levels, staff satisfaction levels, etc.

Clustering Alarms to Define an Incident:

The following discussion concerns the manner in which information process 10 may define the occurrence of a group of alarms as the occurrence of an incident. Generally speaking, while the individual occurrence of any of the group of alarms may not be a concern, the occurrence of the entire group of alarms may be indicative of a bigger problem (i.e., hence the occurrence of an incident).

Figure 9:
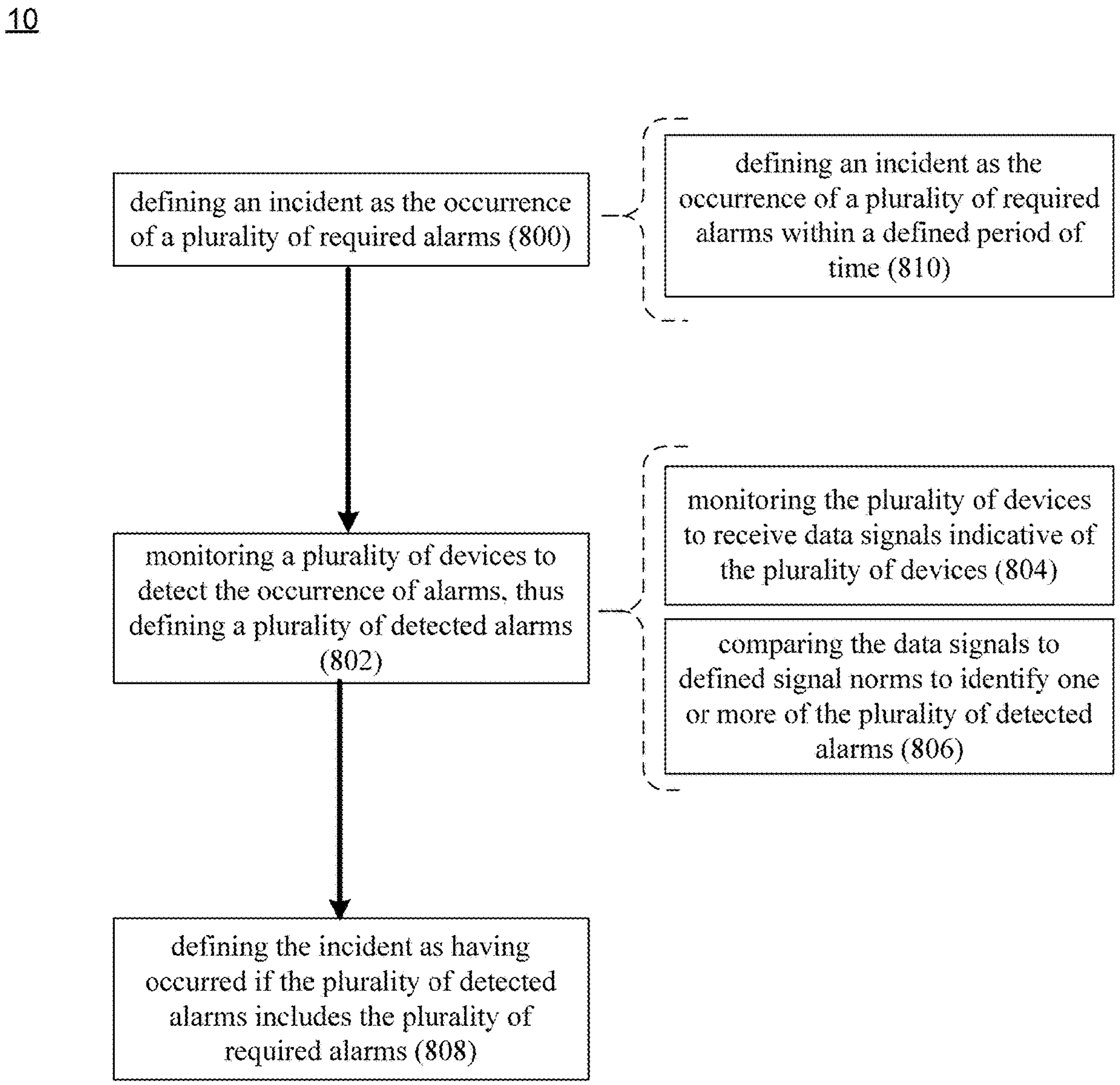
FIG. 9 is another flowchart of the information process of FIG. 1 according to an embodiment of the present disclosure.

Referring also to FIG. 9, information process 10 may define 800 an incident (e.g., incident 272) as the occurrence of a plurality of required alarms. For example, assume that the incident of heart failure may be defined 800 as the occurrence of: low blood pressure, a rapid heart rate, and a low blood oxygen level. While the occurrence of any of these individual alarms may not be indicative of a more serious issue, when a person is experiencing all three of these issues (e.g., low blood pressure, a rapid heart rate, and a low blood oxygen level), that person may be experiencing heart failure. Accordingly, information process 10 may define 800 incident 272 (e.g., heart failure) as the occurrence of low blood pressure, a rapid heart rate, and a low blood oxygen level).

As discussed above, information process 10 may monitor 802 a plurality of devices (e.g., one or more of first vendor devices 202 and/or one or more of second vendor devices 206) to detect the occurrence of alarms. As discussed above, the plurality of devices (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further, the plurality of devices (e.g., one or more of first vendor devices 202 and/or one or more of second vendor devices 206) may be geographically proximate or geographically dispersed. For example, the plurality of devices (e.g., one or more of first vendor devices 202 and/or one or more of second vendor devices 206) may be within one unit of a hospital, spread across an entire hospital, spread across a group of hospitals, spread across a state, or spread across a country.

For this example, assume that the bedside devices (e.g., one or more of first vendor devices 202 and/or one or more of second vendor devices 206) that are monitoring patient 232 generate three alarms (e.g., alarms 274, 276, 278). Being information process 10 is monitoring 802 such devices (e.g., one or more of first vendor devices 202 and/or one or more of second vendor devices 206), information process 10 will detect the occurrence of the alarms, thus defining a plurality of detected alarms (e.g., alarms 274, 276, 278). For this example, assume that:

Detected alarm 274 indicates that patient 232 has low blood pressure;

Detected alarm 276 indicates that patient 232 has a rapid heart rate; and Detected alarm 278 indicates that patient 232 has low oxygen levels in their blood.

When monitoring 802 a plurality of devices (e.g., one or more of first vendor devices 202 and/or one or more of second vendor devices 206) to detect the occurrence of alarms, information process 10 may: monitor 804 the plurality of devices (e.g., one or more of first vendor devices 202 and/or one or more of second vendor devices 206) to receive data signals (e.g., data signals 200 and/or data signals 204) indicative of the plurality of devices (e.g., one or more of first vendor devices 202 and/or one or more of second vendor devices 206).

As also discussed above, such data signals (e.g., one or more of data signals 200 and/or one or more of data signals 204) may concern one or more details of the plurality of devices (e.g., one or more of first vendor devices 202 and/or one or more of second vendor devices 206) and/or uses of the plurality of devices (e.g., one or more of first vendor devices 202 and/or one or more of second vendor devices 206).

Device Details: One or more details of the device (e.g., one or more of first vendor devices 202 and/or one or more of second vendor devices 206) may concern one or more readings, signals and/or alarms that are provided by the device and concern (in the example) the vital signs of a patient.

Device Uses: One or more uses of the device (e.g., one or more of first vendor devices 202 and/or one or more of second vendor devices 206) may concern the manner in which the device is being used (e.g., what is the device doing, what is the device being used for, who is the device assigned/connected to, etc.).

When monitoring 802 a plurality of devices (e.g., one or more of first vendor devices 202 and/or one or more of second vendor devices 206) to detect the occurrence of alarms, information process 10 may: compare 806 the data signals (e.g., data signals 200 and/or data signals 204) to defined signal norms to identify one or more of the plurality of detected alarms (e.g., alarms 274, 276, 278).

As discussed above, examples of such defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As also discussed above, such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

Information process 10 may define 808 the incident (e.g., incident 272) as having occurred if the plurality of detected alarms (e.g., alarms 274, 276, 278) includes the plurality of required alarms (e.g., a low blood pressure alarm, a rapid heart rate alarm, and a low blood oxygen level alarm).

As stated above and for this example:

- Detected alarm 274 indicates that patient 232 has low blood pressure;
- Detected alarm 276 indicates that patient 232 has a rapid heart rate; and
- Detected alarm 278 indicates that patient 232 has low oxygen levels in their blood.

Accordingly, information process 10 may define 808 incident 272 (e.g., a heart failure incident) as having occurred since detected alarm 274 indicates that patient 232 has low blood pressure; detected alarm 276 indicates that patient 232 has a rapid heart rate; and detected alarm 278 indicates that patient 232 has low oxygen levels in their blood.

Oftentimes, the occurrence of a plurality of alarms is only significant if such alarms occurred in a temporarily-proximate fashion. For example, a low blood pressure alarm, followed by a rapid heart rate alarm a week later (when the low blood pressure alarm no longer exists), followed by a low blood oxygen level alarm a week later (when the low blood pressure alarm and the rapid heart rate alarm no longer exist) is probably NOT indicative of incident 272 (e.g., a heart failure incident). Accordingly and when defining 800 an incident (e.g., a heart failure incident) as the occurrence of a plurality of required alarms (e.g., a low blood pressure alarm, a rapid heart rate alarm, and a low blood oxygen level alarm), information process 10 may define 810 the incident (e.g., a heart failure incident) as the occurrence of a plurality of required alarms (e.g., a low blood pressure alarm, a rapid heart rate alarm, and a low blood oxygen level alarm) within a defined period of time.

Predicting an Incident:

As discussed above, information process 10 may define the occurrence of a group of alarms as the occurrence of an incident. The following discussion concerns the manner in which information process 10 may predict the occurrence of an incident when a portion of the group of alarms that defines such an incident has occurred.

Figure 10:
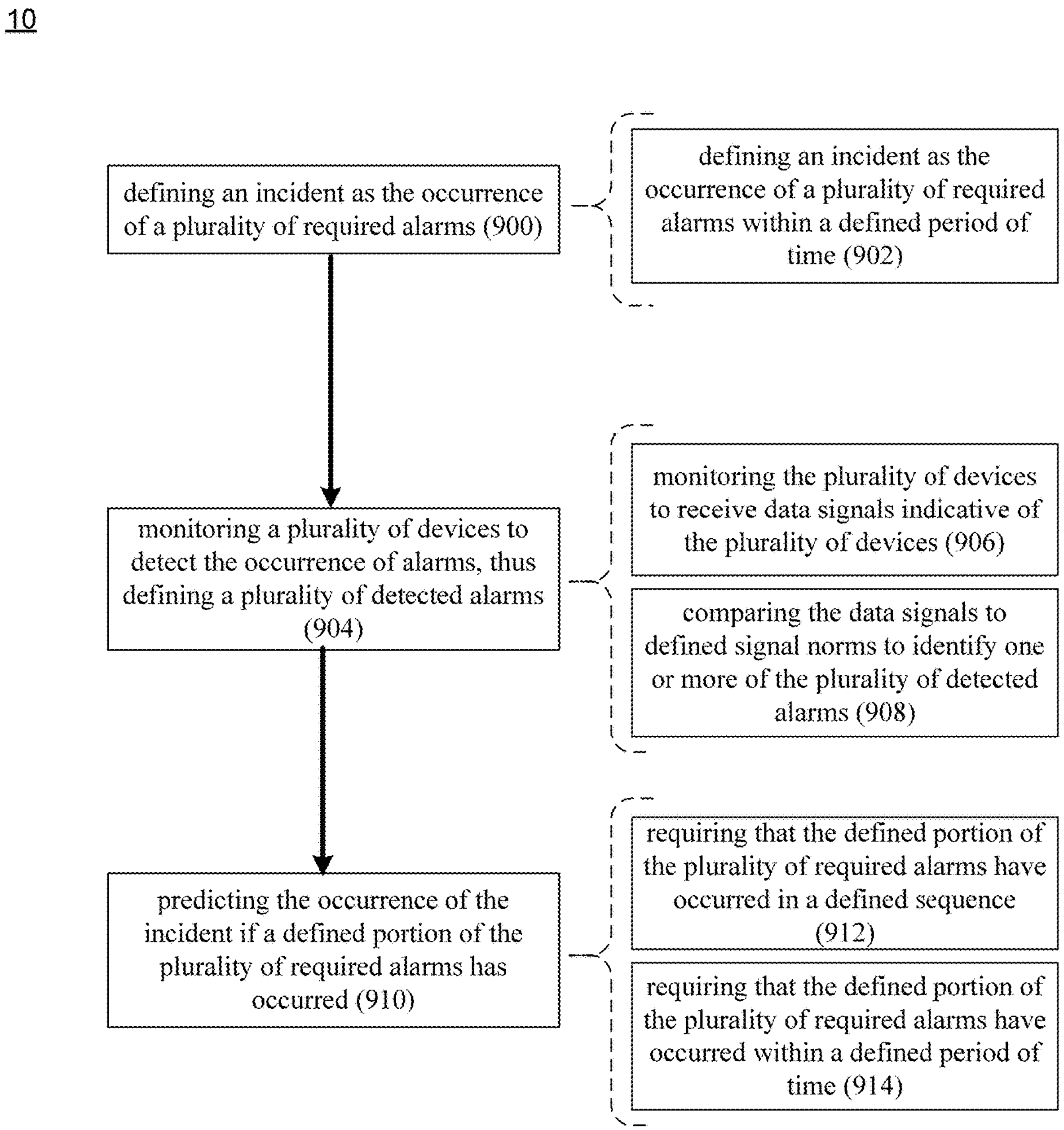
FIG. 10 is another flowchart of the information process of FIG. 1 according to an embodiment of the present disclosure.

Referring also to FIG. 10 and as discussed above, information process 10 may define 900 an incident (e.g., incident 272) as the occurrence of a plurality of required alarms, wherein the incident of heart failure may be defined 900 as the occurrence of: low blood pressure, a rapid heart rate, and a low blood oxygen level. As also discussed above, when defining 900 an incident (e.g., a heart failure incident) as the occurrence of a plurality of required alarms (e.g., a low blood pressure alarm, a rapid heart rate alarm, and a low blood oxygen level alarm), information process 10 may define 902 the incident (e.g., a heart failure incident) as the occurrence of a plurality of required alarms (e.g., a low blood pressure alarm, a rapid heart rate alarm, and a low blood oxygen level alarm) within a defined period of time.

Further and as discussed above, information process 10 may monitor 904 a plurality of devices (e.g., one or more of first vendor devices 202 and/or one or more of second vendor devices 206) to detect the occurrence of alarms. As also discussed above, the plurality of devices (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further and as discussed above, the plurality of devices (e.g., one or more of first vendor devices 202 and/or one or more of second vendor devices 206) may be geographically proximate or geographically dispersed (e.g., within one unit of a hospital, spread across an entire hospital, spread across a group of hospitals, spread across a state, or spread across a country).

As discussed above, when monitoring 904 a plurality of devices (e.g., one or more of first vendor devices 202 and/or one or more of second vendor devices 206) to detect the occurrence of alarms, information process 10 may: monitor 906 the plurality of devices (e.g., one or more of first vendor devices 202 and/or one or more of second vendor devices 206) to receive data signals (e.g., data signals 200 and/or data signals 204) indicative of the plurality of devices (e.g., one or more of first vendor devices 202 and/or one or more of second vendor devices 206).

As also discussed above, such data signals (e.g., one or more of data signals 200 and/or one or more of data signals 204) may concern one or more details of the plurality of devices (e.g., one or more of first vendor devices 202 and/or one or more of second vendor devices 206) and/or uses of the plurality of devices (e.g., one or more of first vendor devices 202 and/or one or more of second vendor devices 206).

As also discussed above, when monitoring 904 a plurality of devices (e.g., one or more of first vendor devices 202 and/or one or more of second vendor devices 206) to detect the occurrence of alarms, information process 10 may: compare 908 the data signals (e.g., data signals 200 and/or data signals 204) to defined signal norms to identify one or more of the plurality of detected alarms (e.g., alarms 274, 276, 278).

As discussed above, examples of such defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As also discussed above, such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

Information process 10 may predict 910 the occurrence of the incident (e.g., incident 272) if a defined portion of the plurality of required alarms (e.g., a low blood pressure alarm, a rapid heart rate alarm, and a low blood oxygen level alarm) has occurred. For example, if a patient is experiencing e.g., low blood pressure and a rapid heart rate, information process 10 may predict 910 the occurrence of incident 272 (e.g., heart failure), as a defined portion (e.g., ⅔$^{rds}$) of the plurality of required alarms (e.g., a low blood pressure alarm, a rapid heart rate alarm, and a low blood oxygen level alarm) have occurred (and information process 10 is anticipating that the patient will soon be experiencing low blood oxygen levels).

For example and when predicting 910 the occurrence of the incident (e.g., incident 272) if a defined portion (e.g., ⅔$^{rds}$) of the plurality of required alarms (e.g., a low blood pressure alarm, a rapid heart rate alarm, and a low blood oxygen level alarm) has occurred, information process 10 may: require 912 that the defined portion (e.g., ⅔$^{rds}$) of the plurality of required alarms (e.g., a low blood pressure alarm, a rapid heart rate alarm, and a low blood oxygen level alarm) have occurred in a defined sequence.

As discussed above, low blood pressure, a rapid heart rate, and a low blood oxygen level are the three events that define the occurrence of heart failure (e.g., incident 272). However, the sequence in which these events occur may be important to making a prediction of heart failure. For example, history may show that low blood pressure and a rapid heart rate will likely result in a low blood oxygen level shortly thereafter; thus enabling information process 10 to predict 910 the occurrence of incident 272 (e.g., heart failure), anticipating that the patient will soon be experiencing low blood oxygen levels. However, history may show that a low blood oxygen level and low blood pressure may not result in a rapid heart rate shortly thereafter; thus preventing information process 10 from predicting 910 the occurrence of incident 272 (e.g., heart failure), anticipating that the patient will not soon be experiencing a rapid heart rate.

Further and when predicting 910 the occurrence of the incident (e.g., incident 272) if a defined portion (e.g., ⅔$^{rds}$) of the plurality of required alarms (e.g., a low blood pressure alarm, a rapid heart rate alarm, and a low blood oxygen level alarm) has occurred, information process 10 may: require 914 that the defined portion (e.g., ⅔$^{rds}$) of the plurality of required alarms (e.g., a low blood pressure alarm, a rapid heart rate alarm, and a low blood oxygen level alarm) have occurred within a defined period of time. As discussed above, the occurrence of a plurality of alarms is only significant if such alarms occurred in a temporarily-proximate fashion. For example, a low blood pressure alarm, followed by a rapid heart rate alarm a week later (when the low blood pressure alarm no longer exists), followed by a low blood oxygen level alarm a week later (when the low blood pressure alarm and the rapid heart rate alarm no longer exist) is probably NOT indicative of incident 272 (e.g., a heart failure incident). Accordingly and when predicting 910 the occurrence of the incident (e.g., incident 272) if a defined portion (e.g., ⅔$^{rds}$) of the plurality of required alarms (e.g., a low blood pressure alarm, a rapid heart rate alarm, and a low blood oxygen level alarm) has occurred, information process 10 may: require 914 that the defined portion (e.g., ⅔$^{rds}$) of the plurality of required alarms (e.g., a low blood pressure alarm, a rapid heart rate alarm, and a low blood oxygen level alarm) have occurred within a defined period of time.

The defined portion (e.g., ⅔$^{rds}$) of the plurality of required alarms (e.g., a low blood pressure alarm, a rapid heart rate alarm, and a low blood oxygen level alarm) may be defined via massive data sets that are processed by machine learning. As discussed above, information process 10 may train an AI model (e.g., AI model 268) based, at least in part, upon the categorized alarms (e.g., categorized alarms 264). For example, data set 270 may be generated and AI model 268 may be trained based upon data set 270. Data set 270 may include e.g., categorized alarms from the medical environment (e.g., hospital 246 . . . or a portion thereof) and from other medical environments (not shown), wherein AI model 268 may be trained by processing data set 270 to extract patterns hidden within data set 270.

Machine learning models extract patterns from a dataset through a process called training. During training, the model learns to recognize patterns and relationships within the data by adjusting its internal parameters or weights. Accordingly, by training AI model 268 based, at least in part, upon categorized alarms 264, various patterns may be extracted concerning e.g., average alarms counts/types and how they relate to patient demographics, hospital locations, staffing levels, staff attrition levels, staff satisfaction levels, etc.

Clustering Incidents to Define an Event:

As discussed above, information process 10 may define the occurrence of a group of alarms as the occurrence of an incident. Generally speaking, while the individual occurrence of any of the group of alarms may not be a concern, the occurrence of the entire group of alarms may be indicative of a bigger problem (i.e., hence the occurrence of an incident). Further and as will be discussed below, information process 10 may define the occurrence of a group of incidents as the occurrence of an event. Generally speaking, while the individual occurrence of any of the group of incidents may not be a concern, the occurrence of the entire group of incidents may be indicative of a bigger problem (i.e., hence the occurrence of an event).

Figure 11:
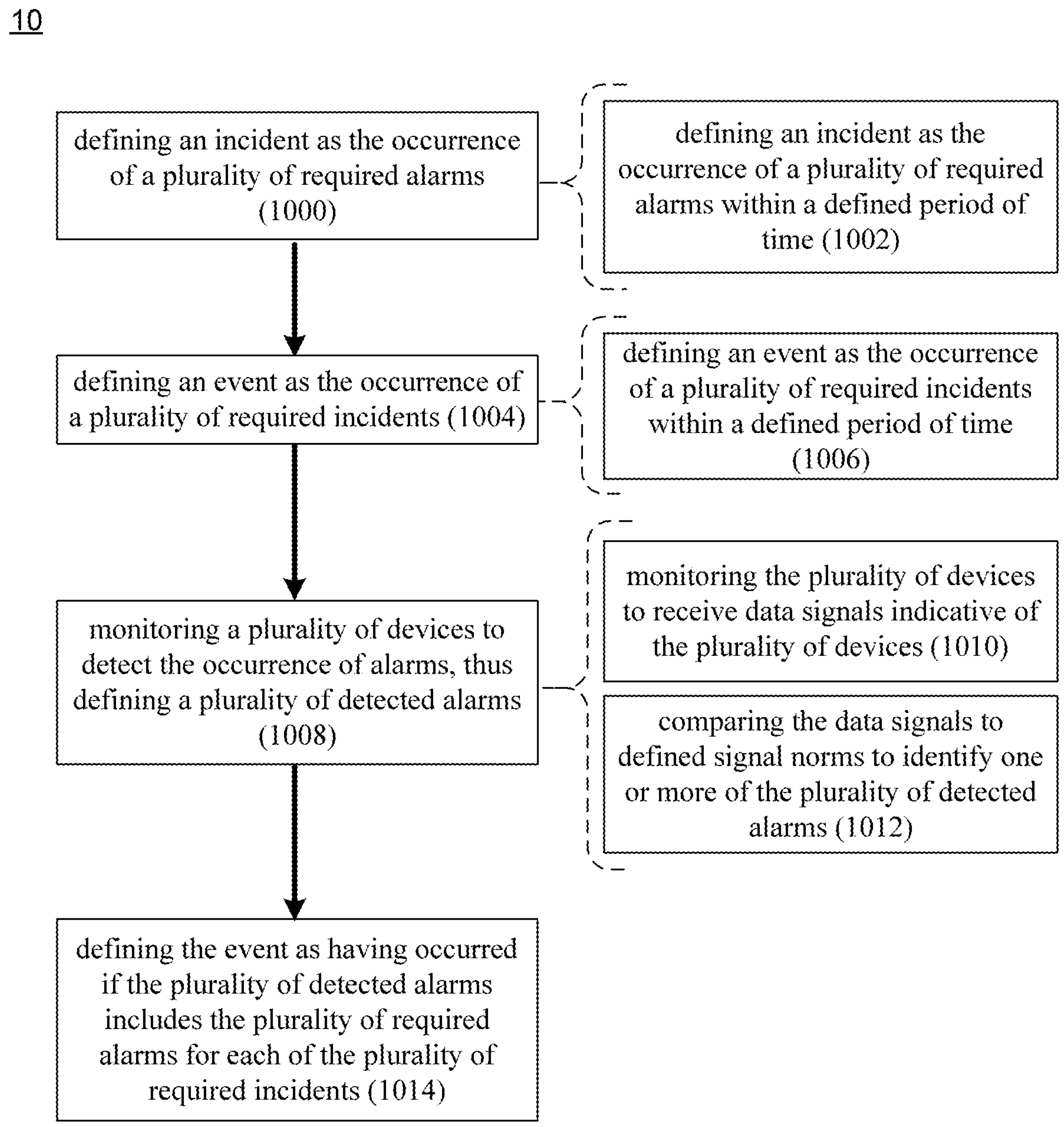
FIG. 11 is another flowchart of the information process of FIG. 1 according to an embodiment of the present disclosure.

Referring also to FIG. 11 and as discussed above, information process 10 may define 1000 an incident (e.g., incident 272) as the occurrence of a plurality of required alarms, wherein the incident of heart failure may be defined 1000 as the occurrence of: low blood pressure, a rapid heart rate, and a low blood oxygen level. As also discussed above, when defining 1000 an incident (e.g., a heart failure incident) as the occurrence of a plurality of required alarms (e.g., a low blood pressure alarm, a rapid heart rate alarm, and a low blood oxygen level alarm), information process 10 may define 1002 the incident (e.g., a heart failure incident) as the occurrence of a plurality of required alarms (e.g., a low blood pressure alarm, a rapid heart rate alarm, and a low blood oxygen level alarm) within a defined period of time.

Information process 10 may define 1004 an event (e.g., event 280) as the occurrence of a plurality of required incidents. For example, the occurrence of incidents 272, 282, 284 may be indicative of the occurrence of an event (e.g., event 280). For example, incident 272 is deemed to have occurred if three alarms (e.g., alarms 274, 276, 278) have occurred. And similarly, information process 10 may deem incidents 282, 284 to have occurred if a plurality of alarms (not shown) associated with each of incidents 282, 284 have occurred. Assume for this example that the plurality of alarms (not shown) associated with incident 282 concern the functioning of the kidneys and, therefore, incident 282 may indicate renal failure. Further assume for this example that the plurality of alarms (not shown) associated with incident 284 concern the functioning of the respiratory system and, therefore, incident 284 may indicate respiratory failure. Accordingly, when incidents 272, 282, 284 (namely heart failure, renal failure and respiratory failure) have occurred, information process 10 may deem the occurrence of such incidents to be indicative of the occurrence of event 280 (namely systemic organ failure).

Further, while incidents 272, 282, 284 are described above as being different incidents that result in event 280, this is for illustrative purposes only, as other configurations are possible and are considered to be within the scope of this disclosure. For example, assume that each of incidents 272, 282, 284 is the same (e.g., ricin poisoning). Accordingly, if three ricin incidents occur, event 280 may be a terrorist attack.

When defining 1004 an event (e.g., event 280) as the occurrence of a plurality of required incidents (e.g., incidents 272, 282, 284), information process 10 may: define 1006 an event (e.g., event 280) as the occurrence of a plurality of required incidents (e.g., incidents 272, 282, 284) within a defined period of time.

Oftentimes, the occurrence of a plurality of incidents is only significant if such incidents occurred in a temporarily-proximate fashion. For example, a heart failure incident, followed by a renal failure incident a week later (when the heart failure incident no longer exists), followed by a respiratory failure incident a week later (when the heart failure incident and the renal failure incident no longer exist) is probably NOT indicative of event 280 (e.g., a systemic organ failure event). Accordingly and when defining 1004 an event (e.g., event 280) as the occurrence of a plurality of required incidents (e.g., a heart failure incident, a renal failure incident and a respiratory failure incident), information process 10 may: define 1006 the event (e.g., a systemic organ failure event) as the occurrence of a plurality of required incidents (e.g., a heart failure incident, a renal failure incident and a respiratory failure incident) within a defined period of time As discussed above, information process 10 may monitor 1008 a plurality of devices (e.g., one or more of first vendor devices 202 and/or one or more of second vendor devices 206) to detect the occurrence of alarms. As discussed above, the plurality of devices (e.g., one or more of first vendor devices 202 and/or one or more of second vendor devices 206) may include one or more of: a medical device, a process control device, a networking device, a computing device, a manufacturing device, an agricultural device, an energy/refining device, an aerospace device, a forestry device, and a defense device. Further, the plurality of devices (e.g., one or more of first vendor devices 202 and/or one or more of second vendor devices 206) may be geographically proximate or geographically dispersed. For example, the plurality of devices (e.g., one or more of first vendor devices 202 and/or one or more of second vendor devices 206) may be within one unit of a hospital, spread across an entire hospital, spread across a group of hospitals, spread across a state, or spread across a country.

When monitoring 1008 a plurality of devices (e.g., one or more of first vendor devices 202 and/or one or more of second vendor devices 206) to detect the occurrence of alarms, information process 10 may: monitor 1010 the plurality of devices (e.g., one or more of first vendor devices 202 and/or one or more of second vendor devices 206) to receive data signals (e.g., data signals 200 and/or data signals 204) indicative of the plurality of devices (e.g., one or more of first vendor devices 202 and/or one or more of second vendor devices 206).

As also discussed above, such data signals (e.g., one or more of data signals 200 and/or one or more of data signals 204) may concern one or more details of the plurality of devices (e.g., one or more of first vendor devices 202 and/or one or more of second vendor devices 206) and/or uses of the plurality of devices (e.g., one or more of first vendor devices 202 and/or one or more of second vendor devices 206).

When monitoring 1008 a plurality of devices (e.g., one or more of first vendor devices 202 and/or one or more of second vendor devices 206) to detect the occurrence of alarms, information process 10 may: compare 1012 the data signals (e.g., data signals 200 and/or data signals 204) to defined signal norms to identify one or more of the plurality of detected alarms (e.g., alarms 274, 276, 278).

As discussed above, examples of such defined signal norms (e.g., defined signal norms 228) may include user-defined signal norms and/or machine-defined signal norms. For example and with respect to user-defined signal norms, such user-defined signal norms may be the result of (in this example) medical studies, medical books, insurance charts, medical records, etc. Further and with respect to machine-defined signal norms, such machine-defined signal norms may be defined via massive data sets that are processed by machine learning.

As also discussed above, such defined signal norms (e.g., defined signal norms 228) may be compartmentalized by e.g., gender, race, age, location, device type, device class, seasonality, time of day, etc. Specifically, medical statistics may vary depending upon various factors (including gender, race, age, location, device type, device class, seasonality, and time of day), wherein these factors can influence health outcomes, disease prevalence, treatment response, and other medical parameters.

As discussed above, information process 10 may define 1004 an event (e.g., event 280) as the occurrence of a plurality of required incidents. Assume for this example that the plurality of alarms (not shown) associated with incident 282 concern the functioning of the kidneys and, therefore, incident 282 may indicate renal failure. Further assume for this example that the plurality of alarms (not shown) associated with incident 284 concern the functioning of the respiratory system and, therefore, incident 284 may indicate respiratory failure. Accordingly, when incidents 272, 282, 284 (namely heart failure, renal failure and respiratory failure) have occurred, information process 10 may deem the occurrence of such incidents to be indicative of the occurrence of event 280 (namely systemic organ failure).

Accordingly, information process 10 may define 1014 the event (e.g., event 280) as having occurred if the plurality of detected alarms (which were detected while monitoring 1008 the plurality of devices) includes the plurality of required alarms for each of the plurality of required incidents (e.g., incidents 272, 282, 284). So if each of incidents 272, 282, 284 requires a plurality of alarms to have occurred . . . and if the plurality of detected alarms includes the sum of the plurality of required alarms associated with each of incidents 272, 282, 284, information process 10 may define 1014 the event (e.g., event 280) as having occurred.

Threshold Management:

The following discussion concerns the manner in which information process 10 may help to battle alarm fatigue by processing detected alarms to determine their authenticity and making the necessary adjustments (e.g., to monitoring criteria) to reduce the quantity of inauthentic alarms.

Figure 12:
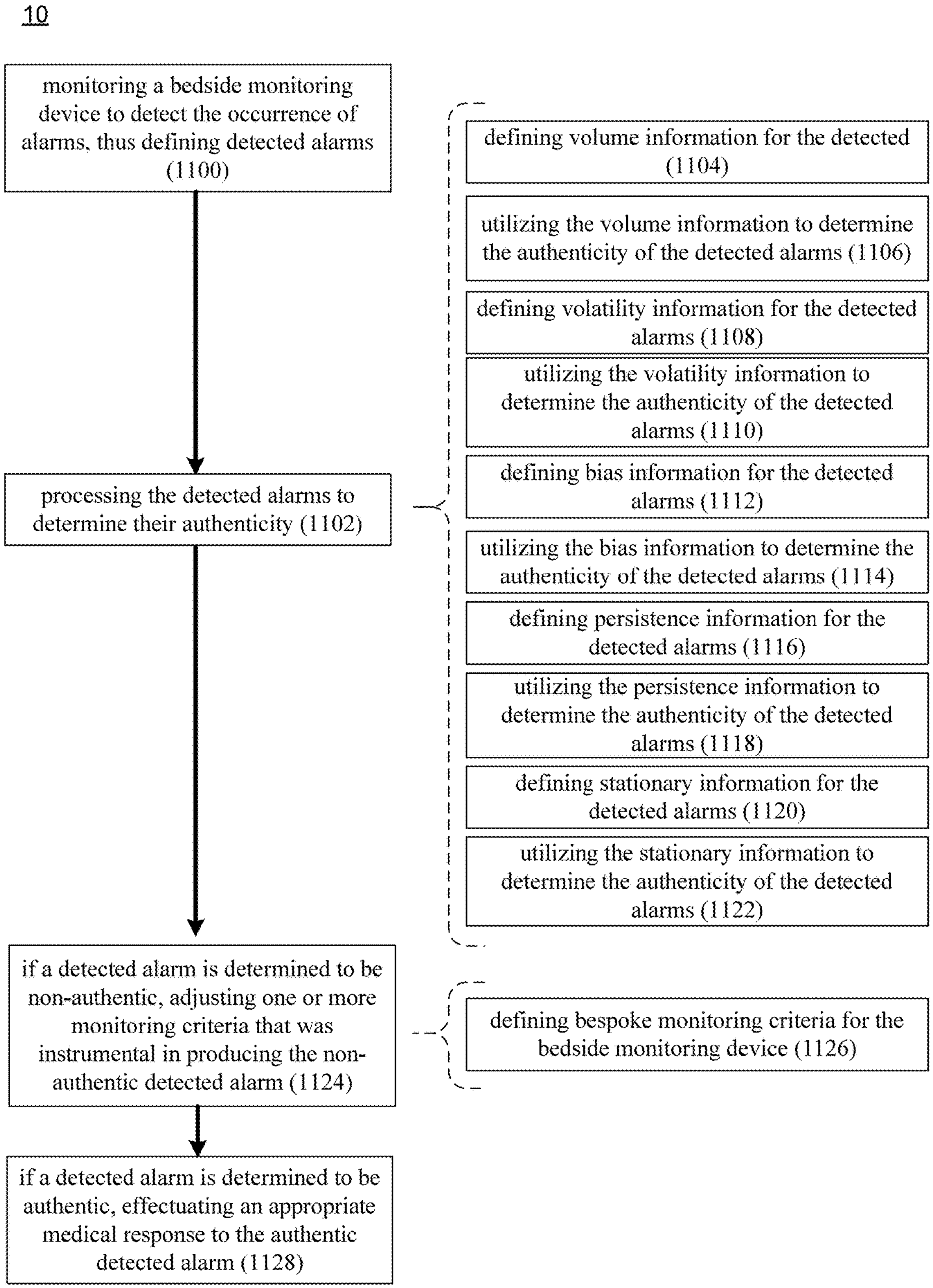
FIG. 12 is another flowchart of the information process of FIG. 1 according to an embodiment of the present disclosure.

Referring also to FIG. 12 and as discussed above, information process 10 may monitor 1100 a bedside monitoring device (e.g., one or more of first vendor devices 202 and/or one or more of second vendor devices 206) to detect the occurrence of alarms (e.g., alarms 274, 276, 278). As discussed above, the device (e.g., one or more of first vendor devices 202 and/or one or more of second vendor devices 206) may include one or more sub devices (e.g., sub devices 224, 226).

As discussed above, studies have shown that the rate of false alarms in hospitals can be alarmingly high. For example, research conducted in intensive care units (ICUs) has reported false alarm rates ranging from 72% to 99%, indicating that the majority of alarms in these settings are false positives. Several factors contribute to the occurrence of false alarms in hospitals:

- Inadequate Alarm Parameters: Alarm systems may be set with default or suboptimal alarm thresholds, leading to alarms that trigger unnecessarily. This can be due to alarm settings being too sensitive or not properly adjusted to patient-specific conditions.
- Device Malfunctions or Technical Issues: Faulty equipment or technical issues with medical devices can result in false alarms. For example, electrode or sensor detachment, poor signal quality, or software glitches can generate false positive alarms.
- Lack of Contextual Information: Alarms may lack the necessary contextual information to help healthcare providers accurately interpret their significance. For instance, alarms may not consider the patient's clinical condition, medications, or concurrent therapies, leading to false alarms that do not require immediate action.
- Inefficient Alarm Management: Healthcare providers may be overwhelmed by the sheer number of alarms, making it challenging to respond promptly and appropriately. This can lead to alarm fatigue, where healthcare providers become desensitized or ignore alarms due to their frequency, potentially compromising patient safety.

As alarms are detected during the above-described monitoring 1100 operation, information process 10 may process 1102 the detected alarms (e.g., alarms 274, 276, 278) to determine their authenticity.

For example and when processing 1102 the detected alarms (e.g., alarms 274, 276, 278) to determine their authenticity, information process 10 may: define 1104 volume information for the detected alarms (e.g., alarms 274, 276, 278); and/or utilize 1106 the volume information to determine the authenticity of the detected alarms (e.g., alarms 274, 276, 278).

- Volume: This signal measure indicates the amount of vital sign sample measurements with respect to the thresholds, e.g., the percentage of samples across the last 30 minutes and 240 minutes where vital measure level is within 90% of the threshold level. When the volume metric is high, i.e., greater than 0.8 across a 30-minute look-back and 0.5 across a 240-minute look-back, it means a high volume of measures in recent history as compared to a longer span of recent history are near the threshold and the condition is met for updating a threshold in the non-conservative direction (i.e., increasing the upper or decreasing the lower). When the volume metric is low, it means a low sample count of measures in recent history and satisfies the condition to update a threshold in the conservative direction (i.e., decreasing the upper threshold or increasing the lower).

Additionally and when processing 1102 the detected alarms (e.g., alarms 274, 276, 278) to determine their authenticity, information process 10 may: define 1108 volatility information for the detected alarms (e.g., alarms 274, 276, 278); and/or utilize 1110 the volatility information to determine the authenticity of the detected alarms (e.g., alarms 274, 276, 278).

- Volatility: The next signal measure involves the level of erratic or volatile behavior. By comparing the variance of the signal over the most recent short history, e.g., last 30 minutes, to the variance of the signal over the most recent history over a longer span of time, e.g., last 240 minutes, we can deduce whether the signal is volatile or non-volatile. When the variance over the last 30 minutes, for example, exceeds that of the last 240 minutes then we can deduce the signal is too volatile for threshold adjustment. Conversely, when the opposite is true the signal is stable and this second condition is met for threshold adjustment.

Further and when processing 1102 the detected alarms (e.g., alarms 274, 276, 278) to determine their authenticity, information process 10 may: define 1112 bias information for the detected alarms (e.g., alarms 274, 276, 278); and/or utilize 1114 the bias information to determine the authenticity of the detected alarms (e.g., alarms 274, 276, 278).

- Bias: This next measure involves understanding the shifting behavior of the signal, or time-varying bias. By measuring the instantaneous first derivative of the signal with respect to time, aka the time rate of change of the signal, aka the signal "velocity", we can understand when the signal is shifting and which direction. For example, when a high percentage of samples across the most recent history, e.g., last 30 or 60 minutes, with non-zero instantaneous velocity, we can deduce the signal is likely to be biased. When not found to be biased, this third condition is met for threshold adjustment.

Additionally and when processing 1102 the detected alarms (e.g., alarms 274, 276, 278) to determine their authenticity, information process 10 may: define 1116 persistence information for the detected alarms (e.g., alarms 274, 276, 278); and/or utilize 1118 the persistence information to determine the authenticity of the detected alarms (e.g., alarms 274, 276, 278).

- Persistence: To understand whether the signal is persistent or non-persistent (i.e., shifting), we compute the integral (i.e., area under the curve) of the difference between the average velocity (or slope) of the signal across the most recent 30 minutes and the average velocity (or slope) of the signal across the most recent 240 minutes. When the 30-minute slope exceeds the 240 minute slope (i.e., the integral is positive), then the signal is said to be persistent (i.e., not shifting overall) and appropriate for threshold update.

Further and when processing 1102 the detected alarms (e.g., alarms 274, 276, 278) to determine their authenticity, information process 10 may: define 1120 stationary information for the detected alarms (e.g., alarms 274, 276, 278);

and/or utilize 1122 the stationary information to determine the authenticity of the detected alarms (e.g., alarms 274, 276, 278).

Stationary: Lastly, measuring whether the signal is unchanged over a timespan is important for understanding whether statistics are changing or not. The signal needs to show stationarity across recent history, e.g., the Augmented Dickey-Fuller test is satisfied across a high percentage of samples in recent history.

While the above discussion concerns volume information, volatility information, bias information, persistence information, and stationary information, this is for illustrative purposes only and is not intended to be a limitation, as other configurations are possible and are considered to be within the scope of this disclosure, examples of which may include but are not limited to: pulse pressure (systolic blood pressure-diastolic), mean arterial pressure, shock index (HR/systolic blood pressure), and external interventions that are perturbations to effect the condition and behavior of the device (e.g., one or more of first vendor devices 202 and/or one or more of second vendor devices 206), such as e.g. medications (the time since, the rate, the total amount) are important to consider here when deciding whether an adjustment to the threshold can be safely performed. If a detected alarms (e.g., one or more of alarms 274, 276, 278) is determined to be non-authentic (in any of the fashions discussed above), information process 10 may adjust 1124 one or more monitoring criteria that was instrumental in producing the non-authentic detected alarms (e.g., one or more of alarms 274, 276, 278).

As discussed above, examples of such monitoring criteria may include defined signal norms (e.g., defined signal norms 228) and/or one or more signal thresholds. Assume as discussed above that the defined signal norms (e.g., defined signal norms 228) concerning heart rate is 60-100 beats per minute. Accordingly, the defined signal norm for heart rate has a lower threshold of 60 and an upper threshold of 100.

Accordingly and when adjusting 1124 one or more monitoring criteria that was instrumental in producing the non-authentic detected alarms (e.g., one or more of alarms 274, 276, 278), information process 10 may: define 1126 bespoke monitoring criteria for the bedside monitoring device (e.g., one or more of first vendor devices 202 and/or one or more of second vendor devices 206). As discussed above, while the defined signal norms (e.g., defined signal norms 228) for a heart rate is 60-100 beats per minute; if the patient (e.g., patient 232) is a seasoned athlete of exceptional health, their "normal" heartrate may be 50-55 beats per minute. Accordingly and in such a situation, information process 10 may: define 1126 bespoke monitoring criteria (e.g., 50-55 beats per minute) for the bedside monitoring device (e.g., one or more of first vendor devices 202 and/or one or more of second vendor devices 206) that is monitoring patient 232.

If a detected alarms (e.g., one or more of alarms 274, 276, 278) is determined to be authentic, information process 10 may effectuate 1128 an appropriate medical response (e.g., notify a doctor, make an emergency announcement, notify medical staff, etc.). to the authentic detected alarms (e.g., one or more of alarms 274, 276, 278).

Operations Health UX:

The following discussion concerns the manner in which information process 10 may render an Operations Health user experience that enables a user to visually monitor the operations within one or more medical institutions.

UX stands for User Experience. It refers to the overall experience and satisfaction that a user has when interacting with a product, system, or service. UX encompasses various elements, including usability, accessibility, ease of use, efficiency, and overall user satisfaction. UX design involves understanding the users' needs, preferences, and goals and designing the product or system in a way that optimizes their experience. It aims to create intuitive, user-friendly, and enjoyable interactions that meet the users' expectations and enhance their overall satisfaction.

Some key aspects of UX design include:

User Research: Gathering insights about the target users through methods such as interviews, surveys, and observations to understand their behaviors, needs, and pain points.

Information Architecture: Organizing and structuring the information within a product or system to facilitate easy navigation and findability. This involves designing menus, categories, and hierarchies to ensure users can locate information or perform tasks efficiently.

Interaction Design: Designing the interactive elements and user interfaces of a product or system. This involves creating intuitive interfaces, designing clear and meaningful feedback for user actions, and considering the overall flow and sequence of user interactions.

Visual Design: Enhancing the visual appeal of the product or system by considering color schemes, typography, iconography, and other visual elements. Visual design aims to create a visually pleasing and cohesive user interface that supports the overall user experience.

Usability Testing: Conducting user testing sessions to evaluate the usability and effectiveness of a product or system. Usability testing helps identify areas of improvement and ensures that the design aligns with the users' expectations and needs.

The goal of UX design is to create products or systems that are intuitive, efficient, and enjoyable for users to interact with. It involves considering the users' needs, goals, and context of use to provide meaningful and satisfying experiences. By prioritizing user experience, organizations can enhance customer satisfaction, increase engagement, and build long-term user loyalty.

Referring also to FIGS. 13A-13D, information process 10 may gather 1200 information from a datasource (e.g., datasource 54, FIG. 1) concerning one or more medical professionals (e.g., user 236) within one or more medical institutions (e.g., hospital 246 . . . or a portion thereof), thus defining gathered information (e.g., gathered information 56).

As discussed above, examples of such medical professionals (e.g., user 236) may include but are not limited to any people (e.g., a nurse, nurse supervisor, medical technician, physician's assistant, physician, etc.) that work for and/or are employed by the one or more medical institutions (e.g., hospital 246 . . . or a portion thereof).

Datasource 54 may include any device that is capable of storing information concerning the one or more medical professionals (e.g., user 236) of the one or more medical institutions (e.g., hospital 246 . . . or a portion thereof), examples of which may include but are not limited to an employment database, a spreadsheet, a storage device, etc.

Generally speaking, gathered information 56 may concern, at least in part, the wellbeing of one or more medical staff (e.g., nurses, nurse supervisors, medical technicians, physician's assistants, physicians, etc.) of the one or more medical institutions (e.g., hospital 246 . . . or a portion thereof).

The wellbeing of one or more medical staff (e.g., nurses, nurse supervisors, medical technicians, physician's assistants, physicians, etc.) may concerns one or more of:

the attrition potential of the one or more medical staff (e.g., nurses, nurse supervisors, medical technicians, physician's assistants, physicians, etc.), namely what is the likelihood of a particular staff member leaving the one or more medical institutions (e.g., hospital 246 . . . or a portion thereof);

the fatigue level of the one or more medical staff (e.g., nurses, nurse supervisors, medical technicians, physician's assistants, physicians, etc.), namely how fatigued (generally) or how alarm fatigued (specifically) is a particular staff member of the one or more medical institutions (e.g., hospital 246 . . . or a portion thereof);

the patient-loading of the one or more medical staff (e.g., nurses, nurse supervisors, medical technicians, physician's assistants, physicians, etc.), namely what is the level of patient loading of a particular staff member of the one or more medical institutions (e.g., hospital 246 . . . or a portion thereof); and the alarm-loading of the one or more medical staff (e.g., nurses, nurse supervisors, medical technicians, physician's assistants, physicians, etc.), namely what is the level of alarm loading of a particular staff member of the one or more medical institutions (e.g., hospital 246 . . . or a portion thereof).

The wellbeing of the one or more medical staff (e.g., nurses, nurse supervisors, medical technicians, physician's assistants, physicians, etc.) may be based, at least in part, upon the quantity and/or authenticity of the alarms (e.g., one or more of alarms 274, 276, 278) to which the one or more medical staff (e.g., nurses, nurse supervisors, medical technicians, physician's assistants, physicians, etc.) were subjected. As discussed above, as alarms are detected during the above-described monitoring operation, information process 10 may process the detected alarms (e.g., alarms 274, 276, 278) to determine their authenticity, wherein such authenticity may be determined by examining e.g., volume information, volatility information, bias information, persistence information, and stationary information Information process 10 may enable 1202 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

Macro Level Viewing Lens 288: a lens that displays a portion of gathered information 56 that concerns the wellbeing of the medical staff (e.g., a nurse, a nurse supervisor, a medical technician, a physician's assistant, a physician, etc.) at any facility within the one or more medical institutions (e.g., hospital 246 . . . or a portion thereof).

Figure 13A:
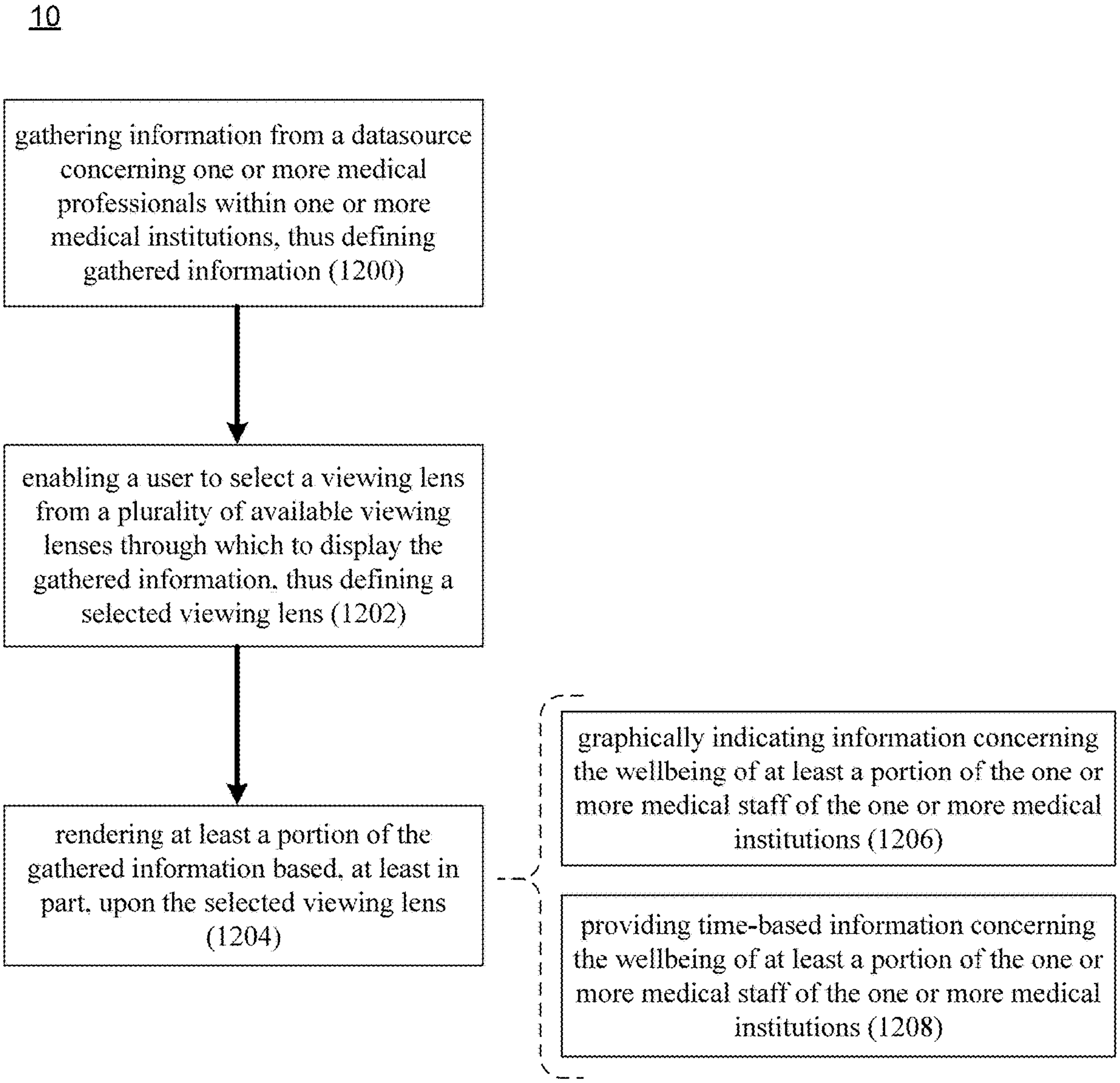
FIG. 13A is another flowchart of the information process of FIG. 1 according to an embodiment of the present disclosure.
Figure 13B:
FIGS. 13B-13D are diagrammatic views of a portion of an Operations Health UX rendered by the information process of FIG. 1 according to an embodiment of the present disclosure.

Facility Level Viewing Lens 290: a lens that displays a portion of gathered information 56 that concerns the wellbeing of the medical staff (e.g., a nurse, a nurse supervisor, a medical technician, a physician's assistant, a physician, etc.) at a particular facility within the one or more medical institutions (e.g., hospital 246 . . . or a portion thereof), as illustrated in FIG. 13B.

Figure 13C:

Unit Level Viewing Lens 292: a lens that displays a portion of gathered information 56 that concerns the wellbeing of the medical staff (e.g., a nurse, a nurse supervisor, a medical technician, a physician's assistant, a physician, etc.) at a particular unit of the one or more medical institutions (e.g., hospital 246 . . . or a portion thereof), as illustrated in FIG. 13C.

Cohort Level Viewing Lens 294: a lens that displays a portion of gathered information 56 that concerns the wellbeing of a selected group of medical staff (e.g., a nurse, a nurse supervisor, a medical technician, a physician's assistant, a physician, etc.) at the one or more medical institutions (e.g., hospital 246 . . . or a portion thereof).

Figure 13D:

Individual Level Viewing Lens 296: a lens that displays a portion of gathered information 56 that concerns the wellbeing of a particular medical staff (e.g., a nurse, a nurse supervisor, a medical technician, a physician's assistant, a physician, etc.) within the one or more medical institutions (e.g., hospital 246 . . . or a portion thereof), as illustrated in FIG. 13D.

Information process 10 may render 1204 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1204 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically indicate 1206 information concerning the wellbeing of at least a portion of the one or more medical staff (e.g., nurses, nurse supervisors, medical technicians, physician's assistants, physicians, etc.) of the one or more medical institutions (e.g., hospital 246 . . . or a portion thereof).

When rendering 1204 at least a portion of the gathered information (e.g., gathered information 56) based, at least in part, upon the selected viewing lens, information process 10 may: provide 1208 time-based information concerning the wellbeing of at least a portion of the one or more medical staff (e.g., nurses, nurse supervisors, medical technicians, physician's assistants, physicians, etc.) of the one or more medical institutions (e.g., hospital 246 . . . or a portion thereof).

Incident Patterns UX:

The following discussion concerns the manner in which information process 10 may render an Incident Patterns user experience that enables a user to visually monitor the operations within one or more medical institutions.

Referring also to FIGS. 14A-14D, information process 10 may gather 1300 information from a datasource (e.g., datasource 54, FIG. 1) concerning one or more incidents (e.g., incident 272) within one or more medical institutions (e.g., hospital 246 . . . or a portion thereof), thus defining gathered information (e.g., gathered information 56).

As discussed above, such incidents (e.g., incident 272) may be defined, at least in part, by one or more alarms (e.g., one or more of alarms 274, 276, 278) occurring within the one or more medical institutions (e.g., hospital 246 . . . or a portion thereof).

As discussed above, one or more alarms (e.g., one or more of alarms 274, 276, 278) may be originated, at least in part, on one or more devices (e.g., one or more of first vendor devices 202 and/or one or more of second vendor devices 206) within the one or more medical institutions (e.g., hospital 246 . . . or a portion thereof).

As discussed above, the one or more alarms (e.g., one or more of alarms 274, 276, 278) may be based, at least in part, upon one or more thresholds (e.g., a lower threshold of 60 and an upper threshold of 100 for the defined signal norm for a heart rate) of the one or more devices (e.g., one or more of first vendor devices 202 and/or one or more of second vendor devices 206) within the one or more medical institutions (e.g., hospital 246 . . . or a portion thereof).

Datasource 54 may include any device that is capable of storing information concerning such incidents (e.g., incident 272), examples of which may include but are not limited to an incident database, a spreadsheet, a storage device, etc.

Generally speaking, gathered information 56 may concern, at least in part, one or more incidents (e.g., incident 272) that occurred within the one or more medical institutions (e.g., hospital 246 . . . or a portion thereof).

Figure 14A:
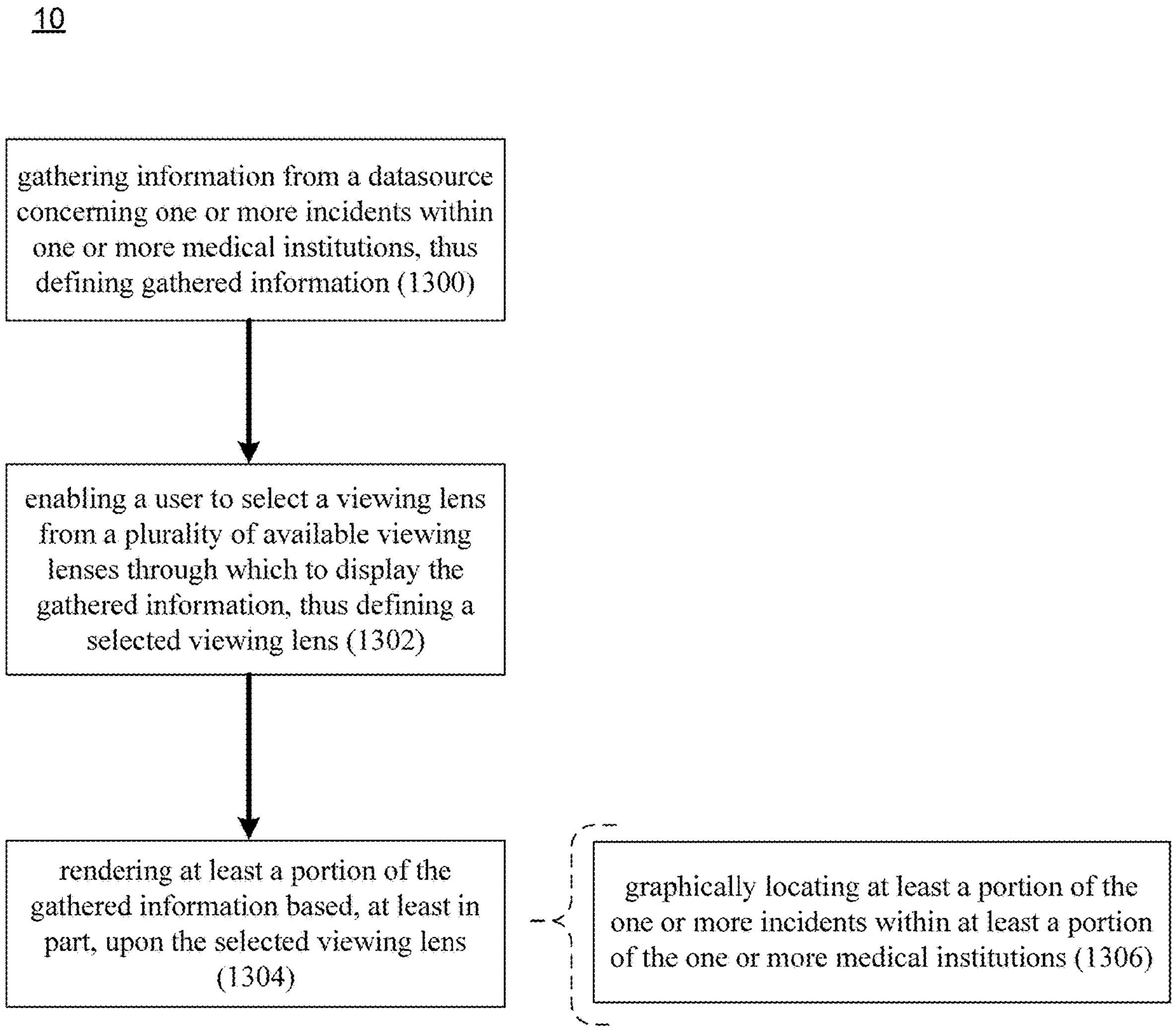
FIG. 14A is another flowchart of the information process of FIG. 1 according to an embodiment of the present disclosure.
Figure 14B:
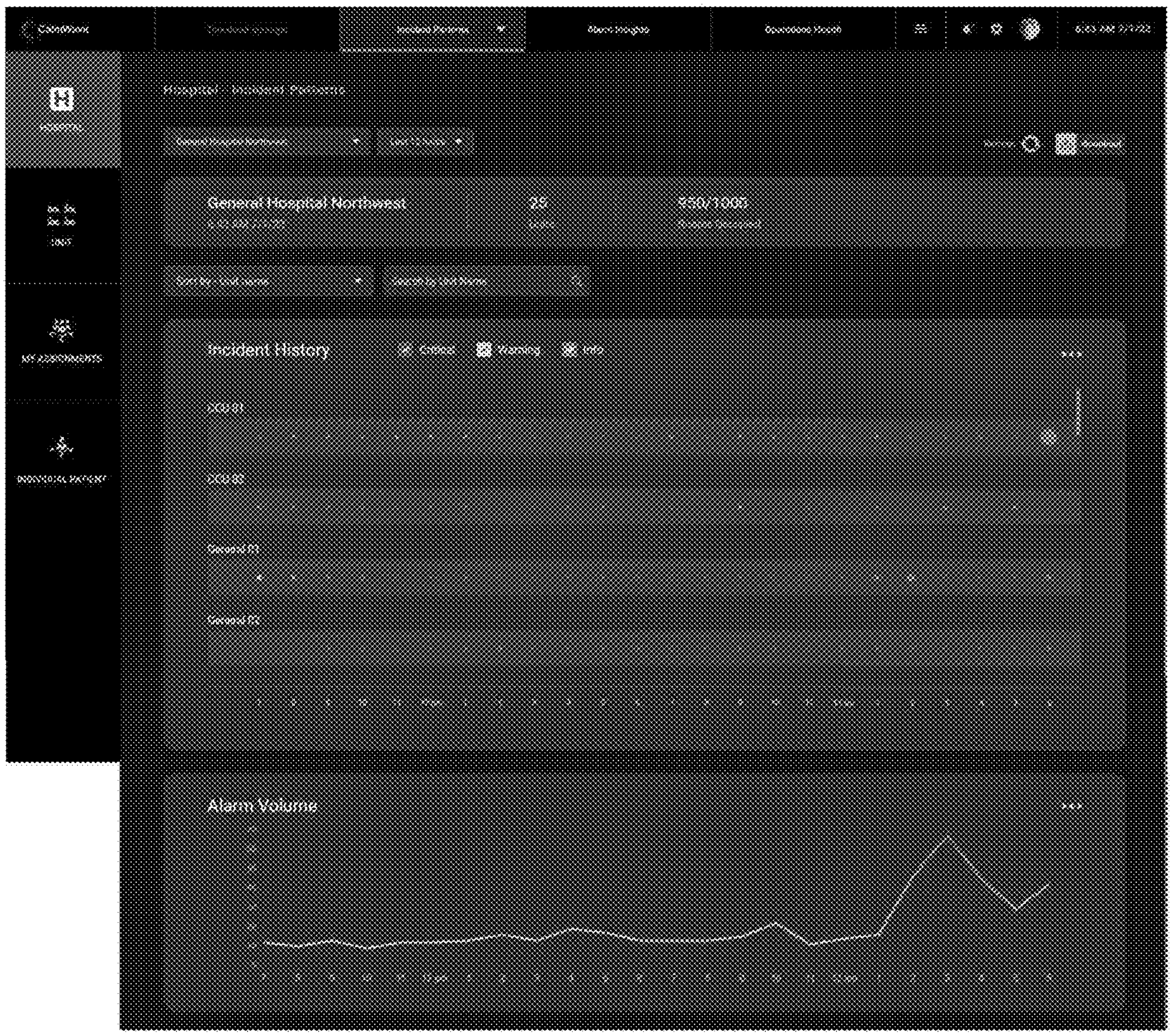
FIGS. 14B-14D are diagrammatic views of a portion of an Incident Patterns UX rendered by the information process of FIG. 1 according to an embodiment of the present disclosure.
Figure 14C:
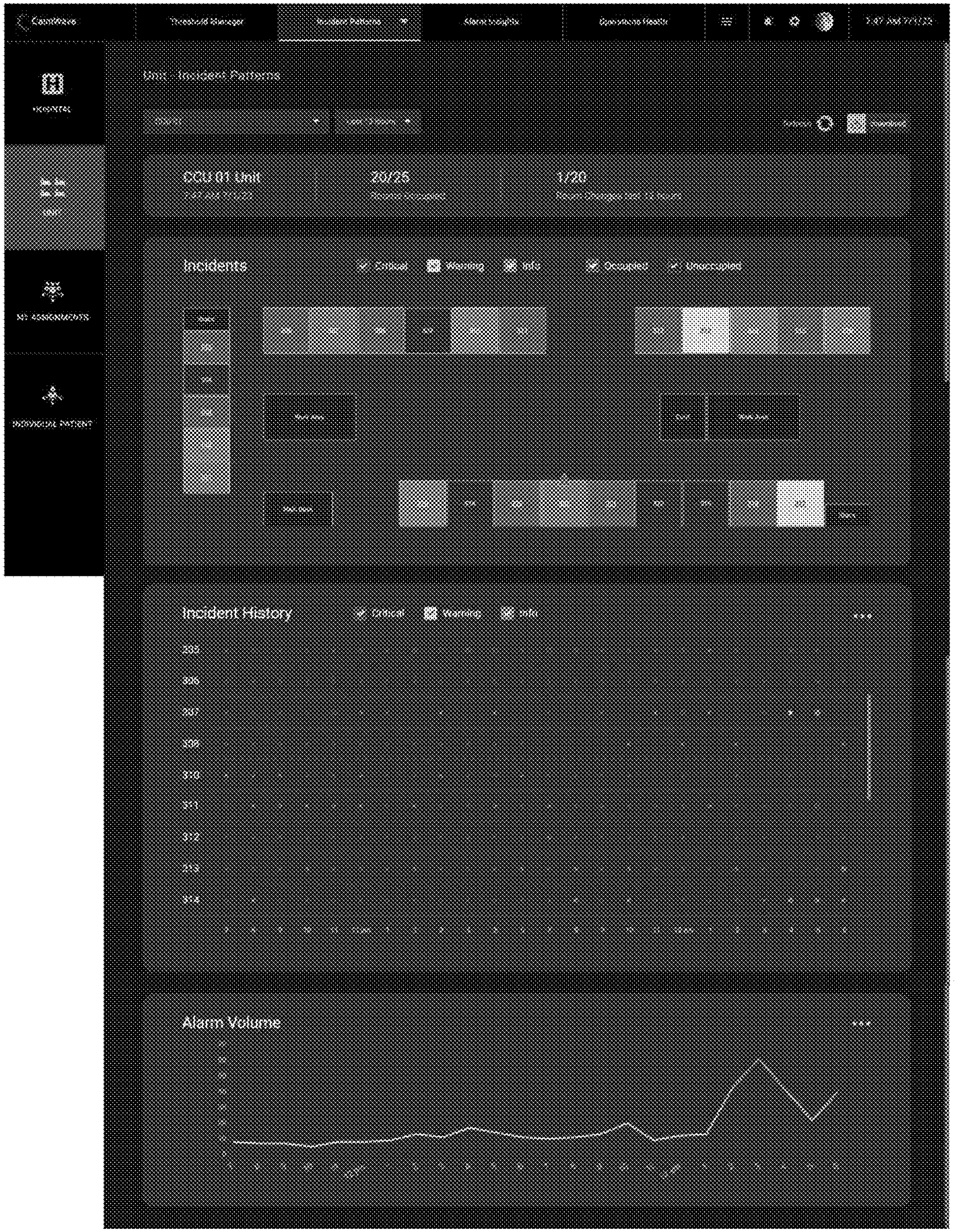
Figure 14D:
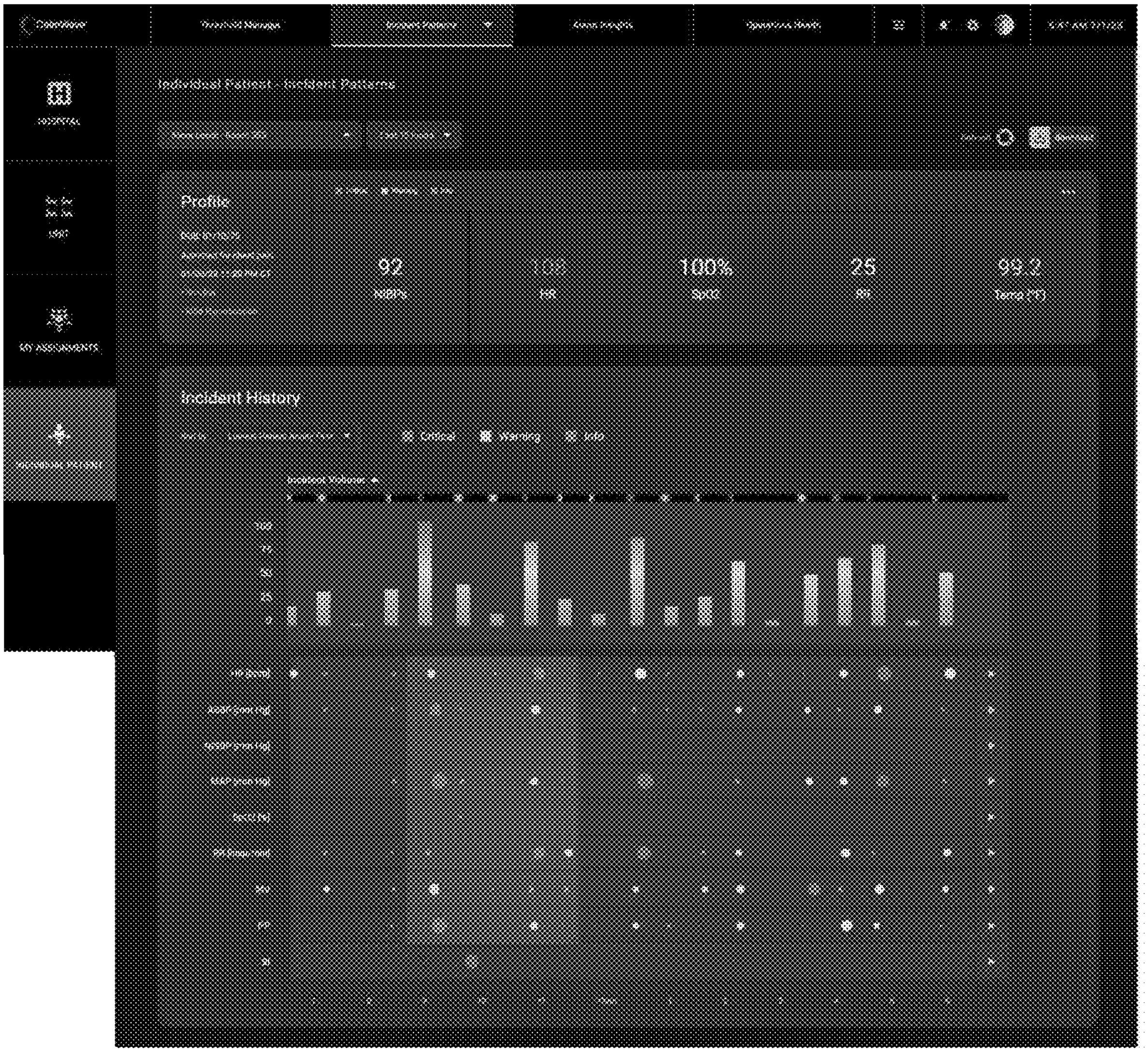

Information process 10 may enable 1302 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

- Macro Level Viewing Lens 288: a lens that displays a portion of gathered information 56 that concerns the incidents at any facility within the one or more medical institutions (e.g., hospital 246 . . . or a portion thereof).
- Facility Level Viewing Lens 290: a lens that displays a portion of gathered information 56 that concerns the incidents at a particular facility within the one or more medical institutions (e.g., hospital 246 . . . or a portion thereof), as illustrated in FIG. 14B.
- Unit Level Viewing Lens 292: a lens that displays a portion of gathered information 56 that concerns the incidents at a particular unit of the one or more medical institutions (e.g., hospital 246 . . . or a portion thereof), as illustrated in FIG. 14C.
- Cohort Level Viewing Lens 294: a lens that displays a portion of gathered information 56 that concerns the incidents of a selected group of patients at the one or more medical institutions (e.g., hospital 246 . . . or a portion thereof).
- Individual Level Viewing Lens 296: a lens that displays a portion of gathered information 56 that concerns the incidents of a particular patient within the one or more medical institutions (e.g., hospital 246 . . . or a portion thereof), as illustrated in FIG. 14D.

Information process 10 may render 1304 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1304 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically locate 1306 at least a portion of the one or more incidents (e.g., incident 272) within at least a portion of the one or more medical institutions (e.g., hospital 246 . . . or a portion thereof).

Information process 10 may enable 1308 a user (e.g., user 236) to adjust the one or more thresholds (e.g., a lower threshold of 60 and an upper threshold of 100 for the defined signal norm for a heart rate) of the one or more devices (e.g., one or more of first vendor devices 202 and/or one or more of second vendor devices 206) within the one or more medical institutions (e.g., hospital 246 . . . or a portion thereof).

Threshold Manager UX:

The following discussion concerns the manner in which information process 10 may render a Threshold Manager user experience that enables a user to visually monitor the operations within one or more medical institutions.

Referring also to FIGS. 15A-15D, information process 10 may gather 1400 information from a datasource (e.g., datasource 54, FIG. 1) concerning one or more thresholds (e.g., a lower threshold of 60 and an upper threshold of 100 for the defined signal norm for a heart rate) within one or more medical institutions (e.g., hospital 246 . . . or a portion thereof), thus defining gathered information (e.g., gathered information 56).

As discussed above, such thresholds (e.g., a lower threshold of 60 and an upper threshold of 100 for the defined signal norm for a heart rate) may be defined, at least in part, within the one or more devices (e.g., one or more of first vendor devices 202 and/or one or more of second vendor devices 206) within the one or more medical institutions (e.g., hospital 246 . . . or a portion thereof).

Datasource 54 may include any device that is capable of storing information concerning such thresholds (e.g., a lower threshold of 60 and an upper threshold of 100 for the defined signal norm for a heart rate), examples of which may include but are not limited to an incident database, a spreadsheet, a storage device, etc.

Generally speaking, gathered information 56 may concern, at least in part, one or more thresholds of one or more devices within the one or more medical institutions.

Figure 15A:
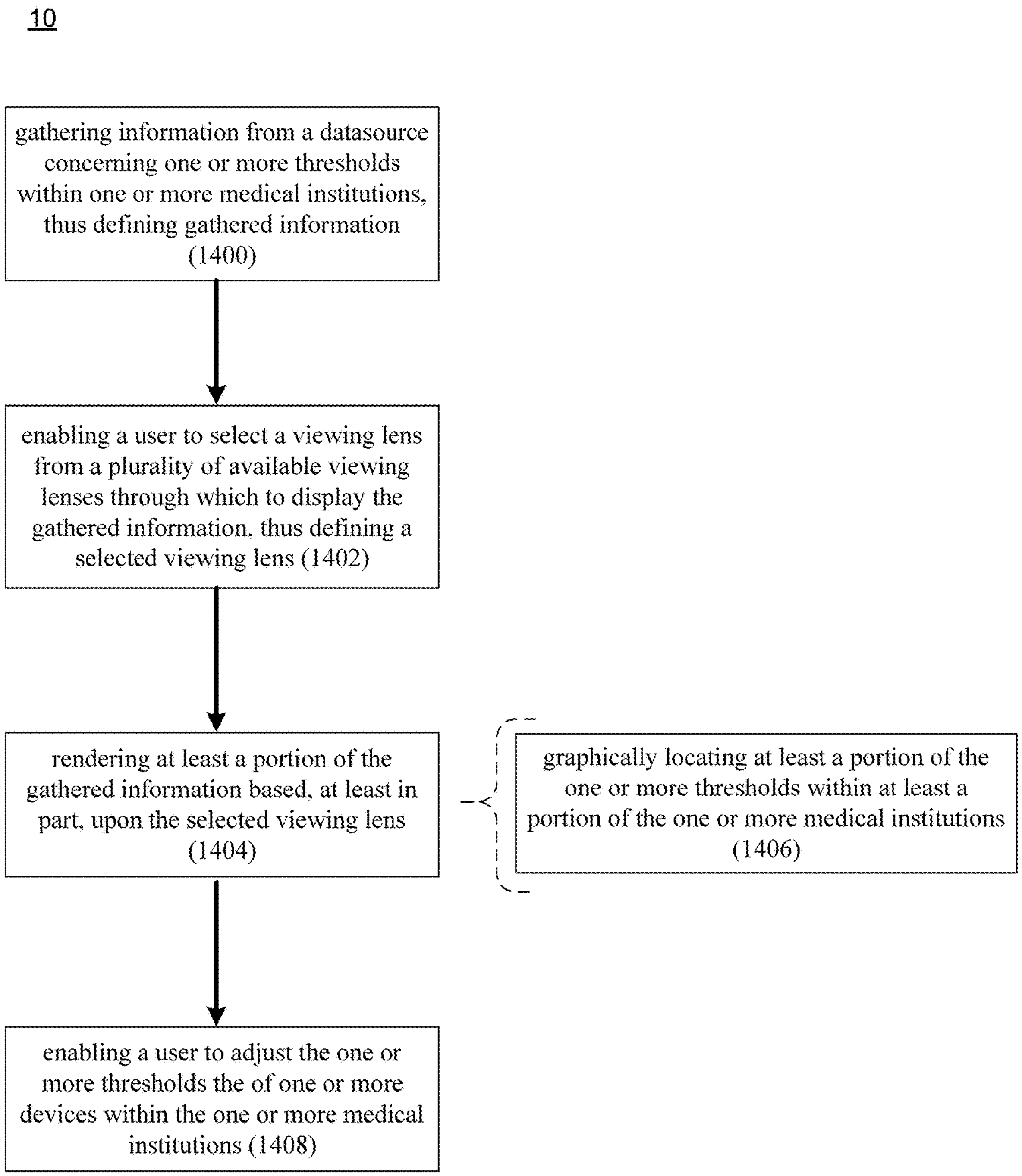
FIG. 15A is another flowchart of the information process of FIG. 1 according to an embodiment of the present disclosure.
Figure 15B:
FIGS. 15B-15D are diagrammatic views of a portion of a Threshold Manager UX rendered by the information process of FIG. 1 according to an embodiment of the present disclosure.
Figure 15C:
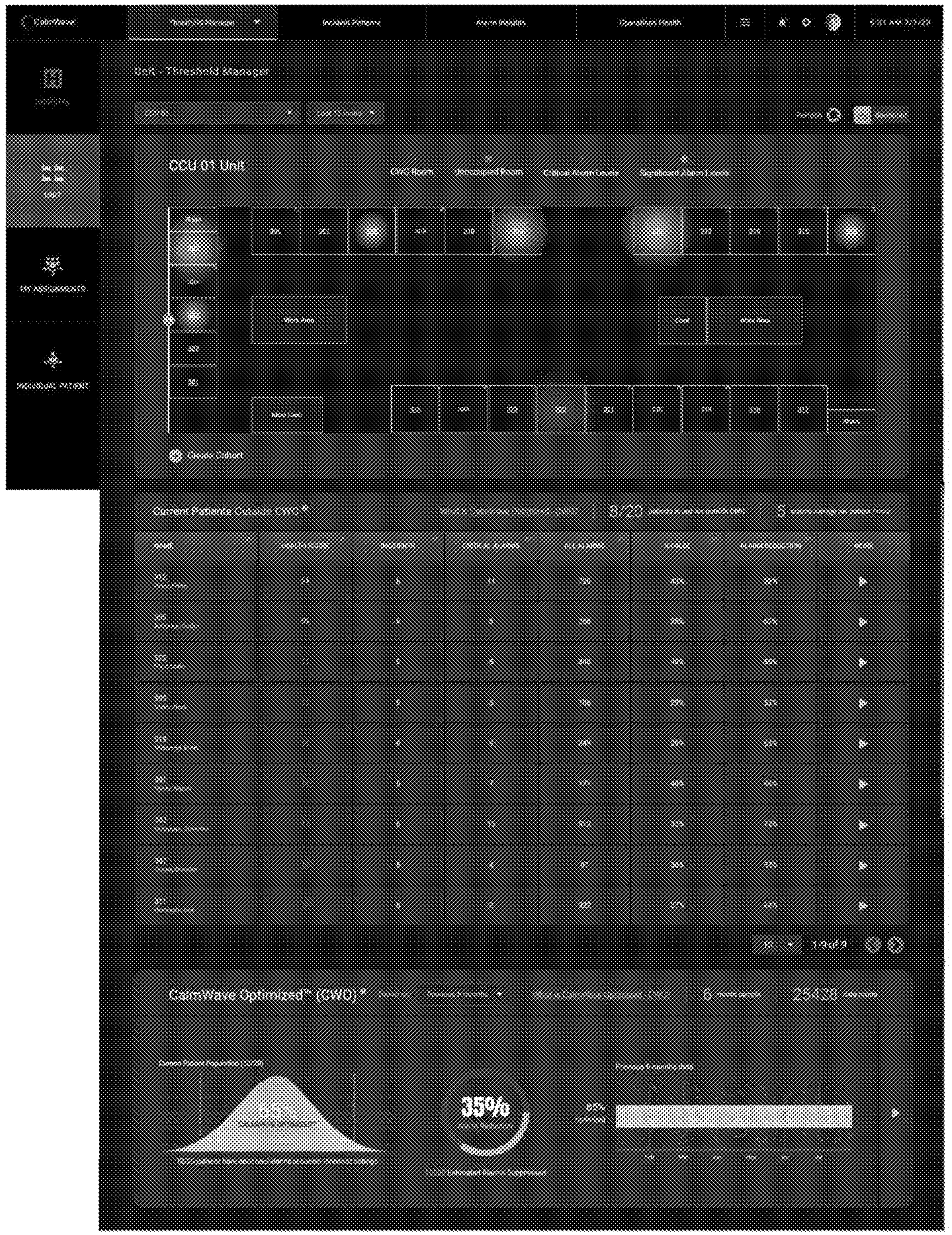
Figure 15D:
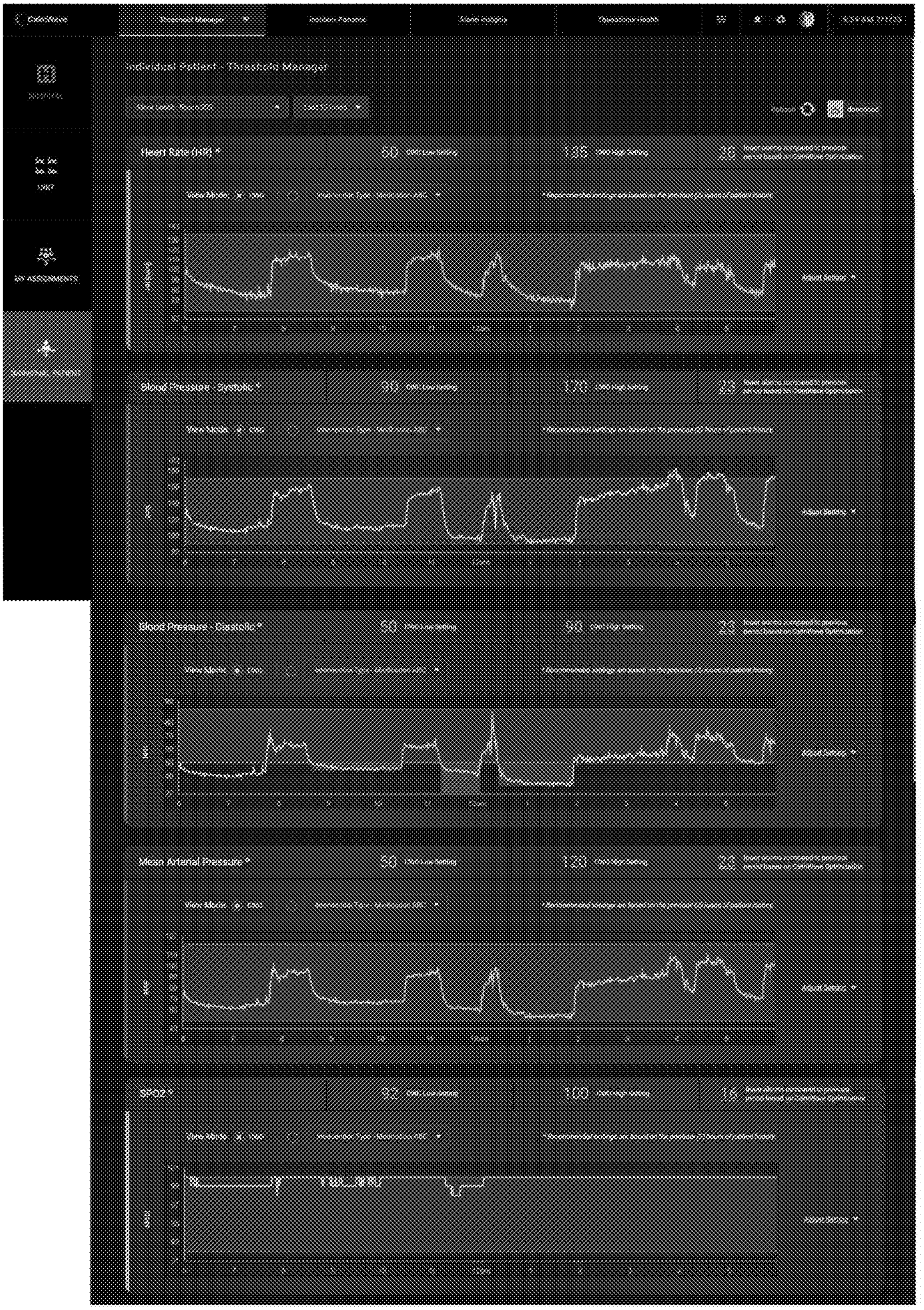

Information process 10 may enable 1402 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

- Macro Level Viewing Lens 288: a lens that displays a portion of gathered information 56 that concerns the thresholds at any facility within the one or more medical institutions (e.g., hospital 246 . . . or a portion thereof).
- Facility Level Viewing Lens 290: a lens that displays a portion of gathered information 56 that concerns the thresholds at a particular facility within the one or more medical institutions (e.g., hospital 246 . . . or a portion thereof).
- Unit Level Viewing Lens 292: a lens that displays a portion of gathered information 56 that concerns the thresholds at a particular unit of the one or more medical institutions (e.g., hospital 246 . . . or a portion thereof), as illustrated in FIGS. 15B-15C.
- Cohort Level Viewing Lens 294: a lens that displays a portion of gathered information 56 that concerns the thresholds of a selected group of patients at the one or more medical institutions (e.g., hospital 246 . . . or a portion thereof).
- Individual Level Viewing Lens 296: a lens that displays a portion of gathered information 56 that concerns the thresholds of a particular patient within the one or more medical institutions (e.g., hospital 246 . . . or a portion thereof), as illustrated in FIG. 15D.

Information process 10 may render 1404 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1404 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically locate 1406 at least a portion of the one or more thresholds within at least a portion of the one or more medical institutions (e.g., hospital 246 . . . or a portion thereof).

Information process 10 may enable 1408 a (e.g., user 236) to adjust the one or more thresholds (e.g., a lower threshold of 60 and an upper threshold of 100 for the defined signal norm for a heart rate) of the one or more devices (e.g., one or more of first vendor devices 202 and/or one or more of second vendor devices 206) within the one or more medical institutions (e.g., hospital 246 . . . or a portion thereof).

Of particular interest is FIGS. 15B-15C, which show two representations of the same information. Specifically, FIG. 15B shows the thresholds and the level at which these thresholds are currently being exceeded (i.e., bigger and/or darker indicators are indicative of more serious alarms) within the medical facility. FIG. 15C shows the same area within the medical facility but illustrates what the levels would be like if information process 10 was utilized to adjust the thresholds to a level that would reduce false alarms.

Alarm Insights UX:

The following discussion concerns the manner in which information process 10 may render an Alarm Insights user experience that enables a user to visually monitor the operations within one or more medical institutions.

Figure 16A:
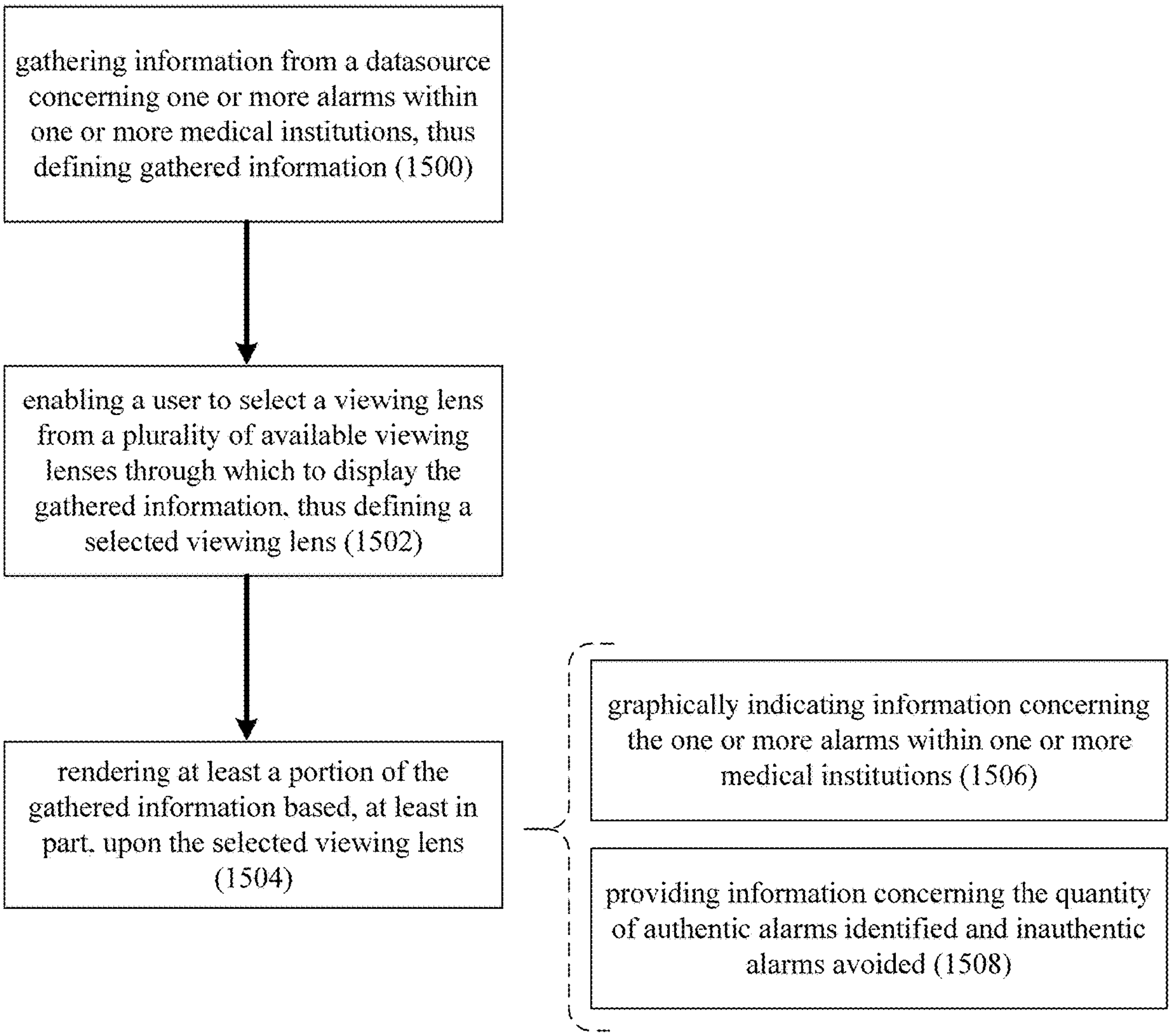
FIG. 16A is another flowchart of the information process of FIG. 1 according to an embodiment of the present disclosure.
Figure 16B:
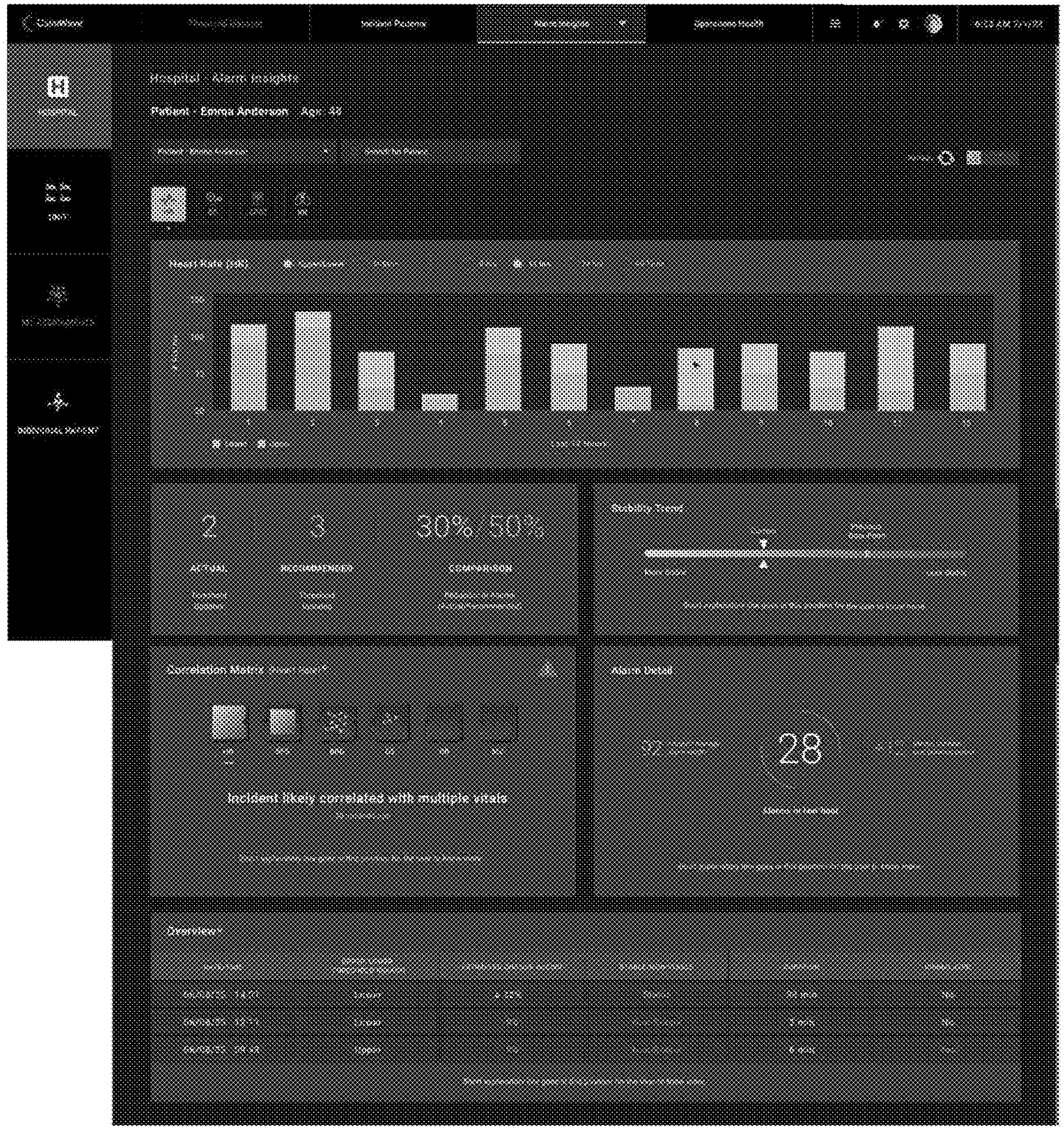
FIG. 16B is a diagrammatic view of a portion of an Alarm Insights UX rendered by the information process of FIG. 1 according to an embodiment of the present disclosure.

Referring also to FIGS. 16A-16B, information process 10 may gather 1500 information from a datasource (e.g., datasource 54, FIG. 1) concerning one or more alarms (e.g., alarms 274, 276, 278) within one or more medical institutions (e.g., hospital 246 . . . or a portion thereof), thus defining gathered information (e.g., gathered information 56).

As discussed above, such alarms (e.g., alarms 274, 276, 278) may be based, at least in part, upon one or more thresholds (e.g., a lower threshold of 60 and an upper threshold of 100 for the defined signal norm for a heart rate) and originated, at least in part, on the one or more devices (e.g., one or more of first vendor devices 202 and/or one or more of second vendor devices 206) within the one or more medical institutions (e.g., hospital 246 . . . or a portion thereof).

Datasource 54 may include any device that is capable of storing information concerning such alarms (e.g., alarms 274, 276, 278), examples of which may include but are not limited to an incident database, a spreadsheet, a storage device, etc.

Generally speaking, gathered information 56 may concern, at least in part, one or more alarms (e.g., one or more of alarms 274, 276, 278) that occurred within the one or more medical institutions (e.g., hospital 246 . . . or a portion thereof).

Information process 10 may enable 1502 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

- Macro Level Viewing Lens 288: a lens that displays a portion of gathered information 56 that concerns the alarms at any facility within the one or more medical institutions (e.g., hospital 246 . . . or a portion thereof).
- Facility Level Viewing Lens 290: a lens that displays a portion of gathered information 56 that concerns the alarms at a particular facility within the one or more medical institutions (e.g., hospital 246 . . . or a portion thereof), as illustrated in FIG. 16B.
- Unit Level Viewing Lens 292: a lens that displays a portion of gathered information 56 that concerns the alarms at a particular unit of the one or more medical institutions (e.g., hospital 246 . . . or a portion thereof).
- Cohort Level Viewing Lens 294: a lens that displays a portion of gathered information 56 that concerns a selected group of alarms at the one or more medical institutions (e.g., hospital 246 . . . or a portion thereof).
- Individual Level Viewing Lens 296: a lens that displays a portion of gathered information 56 that concerns a single alarm within the one or more medical institutions (e.g., hospital 246 . . . or a portion thereof).

Information process 10 may render 1504 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

When rendering 1504 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: graphically indicate 1506 information concerning the one or more alarms (e.g., one or more of alarms 274, 276, 278) within one or more medical institutions (e.g., hospital 246 . . . or a portion thereof).

When rendering 1504 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296), information process 10 may: provide 1508 information concerning the quantity of authentic alarms identified and inauthentic alarms avoided.

Multi-Lens UX:

The following discussion concerns the manner in which information process 10 may allow a user to gather and view information is a UX from any type of organization (e.g., a medical organization, a process control organization, a networking organization, a computing organization, a manufacturing organization, an agricultural organization, an energy/refining organization, an aerospace organization, a forestry organization, and a defense organization).

Figure 17:
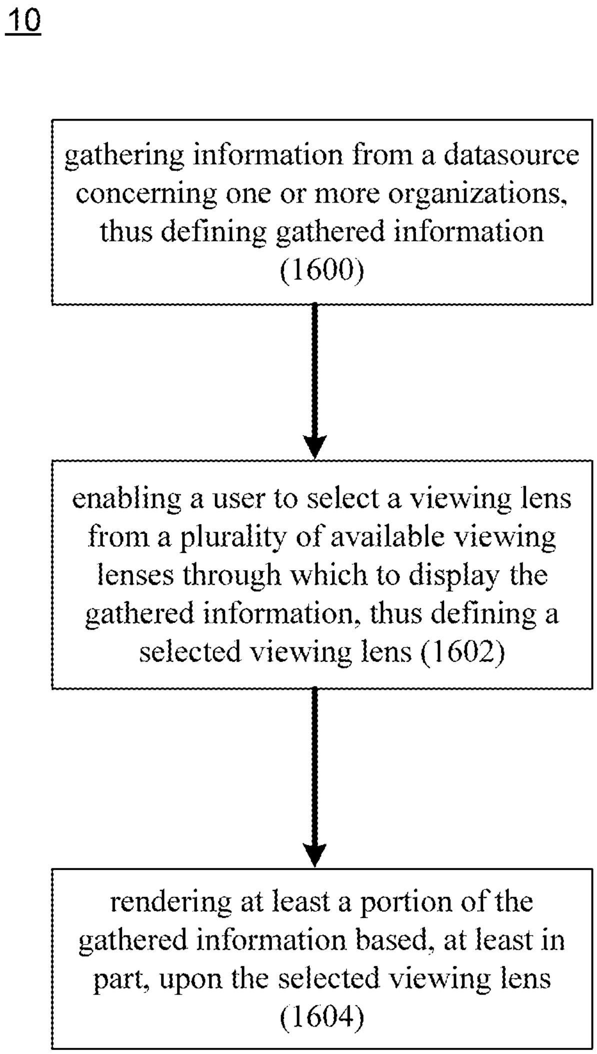
FIG. 17 is another flowchart of the information process of FIG. 1 according to an embodiment of the present disclosure.

Accordingly and referring also to FIG. 17, information process 10 may gather 1600 information from a datasource (e.g., datasource 54, FIG. 1) concerning one or more organizations, thus defining gathered information (e.g., gathered information 56). Datasource 54 may include any device that is capable of storing gathered information 56, examples of which may include but are not limited to an incident database, a spreadsheet, a storage device, etc.

The information (e.g., gathered information 56) may concern, at least in part, the wellbeing of one or more staff of the one or more organizations; one or more incidents that occurred within the one or more organizations; one or more thresholds of one or more devices within the one or more organizations; and one or more alarms that occurred within the one or more organizations.

Generally speaking, gathered information 56 may concern, at least in part, any information about the one or more organizations, examples of which may include but are not limited to:

- Corporate/Company Information: Information concerning the corporate structure of the organization.
- Employment Information: Information concerning the employment practices and employment structure of the organization.
- Employee/Staff Information: Information concerning the employees/staff of the organization, such as number of employees, types of employees, and benefits provided to employees.
- Shareholder Information: Information concerning the shareholders, equity structure, and equity type of the organization.
- Owner Information: Information concerning the owners/majority shareholders of the organization.
- Event Information: Information concerning events within the organization, such as turnover events, attrition events, advertising campaigns, legal events, active lawsuits and historical lawsuits.
- Tax Information: Information concerning the tax structure, tax status, tax filings of the organization.
- Product/Service Information: Information concerning the products and/or services offered by the organization.
- Production Information: Information concerning the production levels/production targets of the organization.
- Sales Information: Information concerning the sales levels/sale targets of the organization.
- Historical Information: Information concerning the history of the organization.
- Location Information: Information concerning the domestic locations and foreign locations of the organization.

Information process 10 may enable 1602 a user (e.g., user 236) to select a viewing lens from a plurality of available viewing lenses (e.g., plurality of lens 286) through which to display the gathered information (e.g., gathered information 56), thus defining a selected viewing lens. The plurality of available viewing lenses (e.g., plurality of lens 286) may include one or more of:

- Macro Level Viewing Lens 288: a lens that displays a portion of gathered information 56 that concerns information at any facility within the one or more organizations.
- Facility Level Viewing Lens 290: a lens that displays a portion of gathered information 56 that concerns information at a particular facility within the one or more organizations.
- Unit Level Viewing Lens 292: a lens that displays a portion of gathered information 56 that concerns information at a particular portion (unit/subsidiary/entity) of the one or more organizations).
- Cohort Level Viewing Lens 294: a lens that displays a portion of gathered information 56 that concerns information for selected group/sub-portion at the one or more organizations.
- Individual Level Viewing Lens 296: a lens that displays a portion of gathered information 56 that concerns a small item of information concerning a single employee, a single corporate event, a single tax filing, a sales of a single product within a single region, etc.

Information process 10 may render 1604 at least a portion of the gathered information (e.g., gathered information 56) based, at least in part, upon the selected viewing lens (e.g., chosen from macro level viewing lens 288, facility level viewing lens 290, unit level viewing lens 292, cohort level viewing lens 294, individual level viewing lens 296).

General

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms “a”, “an” and “the” are intended to include the plural forms as well, unless the context clearly indicates otherwise. It will be further understood that the terms “comprises” and/or “comprising” when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:

gathering information from a datasource concerning one or more thresholds within one or more medical institutions, thus defining gathered information, wherein the gathered information concerns, at least in part, one or more thresholds of one or more devices within the one or more medical institutions;

enabling a user to select a viewing lens from a plurality of available viewing lenses through which to display the gathered information, thus defining a selected viewing lens;

rendering at least a portion of the gathered information based, at least in part, upon the selected viewing lens;

enabling the user to adjust the one or more thresholds of the one or more devices within the one or more medical institutions from one or more current thresholds to one or more adjusted thresholds; and generating a simulation comparing a level at which the one or more current thresholds are being exceeded and a level at which the one or more adjusted thresholds would be exceeded.

2. The computer-implemented method of claim 1 wherein the plurality of available viewing lenses includes one or more of:

a macro level viewing lens;

a facility level viewing lens;

a unit level viewing lens;

a cohort level viewing lens; and an individual level viewing lens.

3. The computer-implemented method of claim 1 wherein rendering at least a portion of the gathered information based, at least in part, upon the selected viewing lens includes:

graphically locating at least a portion of the one or more thresholds within at least a portion of the one or more medical institutions.

4. The computer-implemented method of claim 1 wherein the one or more thresholds are defined, at least in part, within the one or more devices within the one or more medical institutions.

5. The computer-implemented method of claim 1 wherein the thresholds of a particular patient within the one or more medical institutions is reviewable via an individual level viewing lens.

6. A computer program product residing on a computer readable medium having a plurality of instructions stored thereon which, when executed by a processor, cause the processor to perform operations comprising:

gathering information from a datasource concerning one or more thresholds within one or more medical institutions, thus defining gathered information, wherein the gathered information concerns, at least in part, one or more thresholds of one or more devices within the one or more medical institutions;

enabling a user to select a viewing lens from a plurality of available viewing lenses through which to display the gathered information, thus defining a selected viewing lens;

rendering at least a portion of the gathered information based, at least in part, upon the selected viewing lens;

enabling the user to adjust the one or more thresholds of the one or more devices within the one or more medical institutions from one or more current thresholds to one or more adjusted thresholds; and generating a simulation comparing a level at which the one or more current thresholds are being exceeded and a level at which the one or more adjusted thresholds would be exceeded.

7. The computer program product of claim 6 wherein the plurality of available viewing lenses includes one or more of:

a macro level viewing lens;
a facility level viewing lens;
a unit level viewing lens;
a cohort level viewing lens; and
an individual level viewing lens.

8. The computer program product of claim 6 wherein rendering at least a portion of the gathered information based, at least in part, upon the selected viewing lens includes:

graphically locating at least a portion of the one or more thresholds within at least a portion of the one or more medical institutions.

9. The computer program product of claim 6 wherein the one or more thresholds are defined, at least in part, within the one or more devices within the one or more medical institutions.

10. The computer program product of claim 6 wherein the thresholds of a particular patient within the one or more medical institutions is reviewable via an individual level viewing lens.

11. A computing system including a processor and memory configured to perform operations comprising:

gathering information from a datasource concerning one or more thresholds within one or more medical institutions, thus defining gathered information, wherein the gathered information concerns, at least in part, one or more thresholds of one or more devices within the one or more medical institutions;

enabling a user to select a viewing lens from a plurality of available viewing lenses through which to display the gathered information, thus defining a selected viewing lens;

rendering at least a portion of the gathered information based, at least in part, upon the selected viewing lens;

enabling the user to adjust the one or more thresholds of the one or more devices within the one or more medical institutions from one or more current thresholds to one or more adjusted thresholds; and generating a simulation comparing a level at which the one or more current thresholds are being exceeded and a level at which the one or more adjusted thresholds would be exceeded.

12. The computing system of claim 11 wherein the plurality of available viewing lenses includes one or more of:

a macro level viewing lens;
a facility level viewing lens;
a unit level viewing lens;
a cohort level viewing lens; and
an individual level viewing lens.

13. The computing system of claim 11 wherein rendering at least a portion of the gathered information based, at least in part, upon the selected viewing lens includes:

graphically locating at least a portion of the one or more thresholds within at least a portion of the one or more medical institutions.

14. The computing system of claim 11 wherein the one or more thresholds are defined, at least in part, within the one or more devices within the one or more medical institutions.

15. The computing system of claim 11 wherein the thresholds of a particular patient within the one or more medical institutions is reviewable via an individual level viewing lens.

* * * * *